United States Patent
Cox et al.

(10) Patent No.: US 10,407,738 B2
(45) Date of Patent: *Sep. 10, 2019

(54) MARKERS FOR BREAST CANCER

(71) Applicant: Cambridge Enterprise Limited, Cambridge (GB)

(72) Inventors: David Cox, Belmont, CA (US); Dennis Ballinger, Menlo Park, CA (US); Bruce Ponder, Cambridge (GB); Doug Easton, Herts (GB)

(73) Assignee: Cambridge Enterprise Limited, Cambridge (GB)

( * ) Notice: Subject to any disclaimer, the term of this patent is extended or adjusted under 35 U.S.C. 154(b) by 141 days.

This patent is subject to a terminal disclaimer.

(21) Appl. No.: 15/616,679

(22) Filed: Jun. 7, 2017

(65) Prior Publication Data

US 2017/0275707 A1    Sep. 28, 2017

Related U.S. Application Data

(60) Continuation of application No. 14/738,639, filed on Jun. 12, 2015, now Pat. No. 9,702,011, which is a continuation of application No. 12/370,972, filed on Feb. 13, 2009, now Pat. No. 9,068,229, which is a division of application No. 11/606,634, filed on Nov. 29, 2006, now abandoned.

(60) Provisional application No. 60/740,971, filed on Nov. 29, 2005, provisional application No. 60/781,483, filed on Mar. 10, 2006.

(51) Int. Cl.
C12Q 1/6886        (2018.01)

(52) U.S. Cl.
CPC ..... *C12Q 1/6886* (2013.01); *C12Q 2600/106* (2013.01); *C12Q 2600/136* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,812,339 | B1 | 11/2004 | Venter et al. |
| 7,127,355 | B2 | 10/2006 | Cox |
| 7,529,685 | B2 | 5/2009 | Davies |
| 9,051,617 | B2 | 6/2015 | Cox et al. |
| 2002/0123095 | A1 | 9/2002 | Kalush |
| 2003/0092019 | A1 | 5/2003 | Meyer et al. |
| 2003/0099964 | A1 | 5/2003 | Patil |
| 2003/0108910 | A1 | 6/2003 | Toland et al. |
| 2003/0157488 | A1 | 8/2003 | Cox et al. |
| 2004/0002071 | A1 | 1/2004 | Ralph et al. |
| 2004/0023237 | A1 | 2/2004 | Patil et al. |
| 2004/0210400 | A1 | 10/2004 | Konvicka |
| 2004/0229224 | A1 | 11/2004 | Frazer et al. |
| 2004/0241657 | A1 | 12/2004 | Patil et al. |
| 2005/0003410 | A1 | 1/2005 | Frazer et al. |
| 2005/0019787 | A1 | 1/2005 | Berno et al. |
| 2005/0084849 | A1 | 4/2005 | Moskowitz |
| 2005/0196770 | A1 | 9/2005 | Cox et al. |
| 2007/0037198 | A1 | 2/2007 | Cox |
| 2007/0166738 | A1 | 7/2007 | Cox |
| 2008/0131887 | A1 | 6/2008 | Dietrich |
| 2009/0087854 | A1 | 4/2009 | Cox |
| 2009/0208962 | A1 | 8/2009 | Cox |
| 2009/0239226 | A1 | 9/2009 | Cox |
| 2009/0239763 | A1 | 9/2009 | Cox |
| 2011/0015081 | A1 | 1/2011 | Stacey |
| 2011/0015092 | A1 | 1/2011 | Cox et al. |
| 2011/0200588 | A1 | 8/2011 | Cox |
| 2011/0294681 | A1 | 12/2011 | Hinds et al. |
| 2016/0222469 | A1 | 8/2016 | Allman |
| 2018/0080089 | A1 | 3/2018 | Hinds |
| 2018/0305764 | A1 | 10/2018 | Allman |

FOREIGN PATENT DOCUMENTS

| | | |
|---|---|---|
| WO | WO 95/011995 | 5/1995 |
| WO | WO 1998/20167 | 5/1998 |
| WO | WO 00/33161 | 6/2000 |
| WO | WO 2003/025141 | 3/2003 |
| WO | WO 2005/014846 | 2/2005 |
| WO | WO 2005/024067 | 3/2005 |
| WO | WO 2005/086770 A3 | 9/2005 |
| WO | WO 2007/064776 | 6/2007 |
| WO | WO 2007/150044 | 12/2007 |
| WO | WO 2008/117314 | 10/2008 |
| WO | WO 2008/146309 | 12/2008 |
| WO | WO 2009/009752 | 1/2009 |

(Continued)

OTHER PUBLICATIONS

Ponder et al. Polygenic Inherited Predisposition to Breast Cancer. Cold Spring Harbor Symposia on Quantitative Biology, 2005. vol. 70. 35-41.*
Bonnen et al. Haplotype and Linkage Disequilibrium Architecture for Human Cancer-Associated Genes. Genome Research, 2002.*
Pharoah et al. Association Studies For Finding Cancer-Susceptibility Genetic Variants. Nature, 2004. 4:850-860.*
Jun. 7, 2016 Office Action, issued in connection with U.S. Appl. No. 14/738,639.
Nov. 16, 2016 Response, filed in connection with U.S. Appl. No. 14/738,639.
Dec. 1, 2016 Interview Summary, issued in connection with U.S. Appl. No. 14/738,639.
Feb. 28, 2017 Summary of Examiner Interview and Communication Forwarding Terminal Disclaimer, filed in connection with U.S. Appl. No. 14/738,639.
Mar. 7, 2017 Notice of Allowance, issued in connection with U.S. Appl. No. 14/738,639.

(Continued)

*Primary Examiner* — Christopher M Babic
*Assistant Examiner* — Kimberly A. Aron
(74) *Attorney, Agent, or Firm* — Gary J. Gershik; Cooper Dunham LLP

(57) ABSTRACT

Correlations between polymorphisms and breast cancer are provided. Methods of diagnosing, prognosing, and treating breast cancer are provided. Systems and kits for diagnosis, prognosis and treatment of breast cancer are provided. Methods of identifying breast cancer modulators are also described.

9 Claims, 24 Drawing Sheets

(56) References Cited

FOREIGN PATENT DOCUMENTS

| WO | WO 2009/097270 | 8/2009 |
|---|---|---|
| WO | WO 2010/017520 | 2/2010 |
| WO | WO 2010/030929 | 3/2010 |
| WO | WO 2010/139006 | 9/2010 |
| WO | WO 2013/151413 | 10/2013 |

OTHER PUBLICATIONS

Jun. 7, 2010 Office Action, issued in connection with U.S. Appl. No. 12/370,972.
Dec. 6, 2010 Response, filed in connection with U.S. Appl. No. 12/370,972.
Feb. 2, 2011 Final Office Action, issued in connection with U.S. Appl. No. 12/370,972.
Jul. 5, 2011 Notice of Appeal, filed in connection with U.S. Appl. No. 12/370,972.
Nov. 7, 2011 Response, filed in connection with U.S. Appl. No. 12/370,972.
Jul. 18, 2013 Response, filed in connection with U.S. Appl. No. 12/370,972.
Nov. 25, 2013 Office Action, issued in connection with U.S. Appl. No. 12/370,972.
Feb. 21, 2014 Response, filed in connection with U.S. Appl. No. 12/370,972.
Oct. 17, 2014 Office Action, issued in connection with U.S. Appl. No. 12/370,972.
Dec. 8, 2014 Interview Summary, issued in connection with U.S. Appl. No. 12/370,972.
Jan. 12, 2015 Response, filed in connection with U.S. Appl. No. 12/370,972.
Apr. 10, 2015 Notice of Allowance, issued in connection with U.S. Appl. No. 12/370,972.
English language translation of Israeli Office Action dated Jul. 14, 2010 in connection with Israeli Patent Application No. 191566.
Response filed to Israeli Office Action filed Nov. 9, 2010 in connection with Israeli Patent Application No. 191566, including English language translation of transmittal letter.
Israeli Office Action dated Jun. 1, 2011 in connection with Israeli Patent Application No. 191566.
Response filed to Israeli Office Action filed Oct. 2, 2011 in connection with Israeli Patent Application No. 191566.
English language translation of Israeli Office Action dated Feb. 29, 2012 in connection with Israeli Patent Application No. 191566.
English language translation of Response filed to Israeli Office Action dated Jun. 20, 2012 in connection with Israeli Patent Application No. 191566.
European Search Opinion dated Oct. 13, 2008 in connection with European Patent Application No. 06838661.4.
Response to Examination report dated Feb. 12, 2010 in connection with European Patent Application No. 06838661.4.
Response filed to European Examination Report filed Aug. 23, 2010 in connection with European Patent Application No. 06838661.4.
Examination Report dated Feb. 17, 2012 in connection with European Patent Application No. 06838661.4.
Response filed to European Examination Report dated Feb. 22, 2012 in connection with European Patent Application No. 06838661.4.
Australian Examiner's Report dated Jun. 29, 2011 in connection with Australian Application No. 2006320559.
Response filed to Australian Examiner's Report filed on Oct. 18, 2011 in connection with Australian Application No. 2006320559.
Second Australian Examiner's Report dated Nov. 17, 2011 in connection with Australian Application No. 2006320559.
Response filed to Second Australian Examiner's Report filed Dec. 7, 2011 in connection with Australian Application No. 2006320559.
English language translation of Notice from Chinese Patent Office dated Jun. 1, 2011 in connection with Chinese Patent Application No. 200680051710.0.
Response filed to Chinese Notice on Jul. 25, 2011 in connection with Chinese Patent Application No. 200680051710.0, including English Language claims.
English language translation of First Chinese Office Action dated Oct. 13, 2011 in connection with Chinese Patent Application No. 200680051710.0.
Response filed to First Chinese Office Action dated Feb. 9, 2012 in connection with Chinese Patent Application No. 200680051710.0, including English Language claims.
English language translation of Second Chinese Office Action in connection with Chinese Patent Application No. 200680051710.0.
Japanese Office Action dated Feb. 22, 2012 in connection with Japanese Patent Application No. 2008-543446, including English language translation.
Japanese Patent Application Publication No. JP 2005/532780, published Nov. 4, 2005 (Ralph et al.), corresponding to PCT International Publication No. WO 2003/025141.
Japanese Patent Application Publication No. JP 2001/503276, published Mar. 13, 2001 (Jupe et al.) corresponding to PCT International Publication No. WO 1998/20167.
Jun. 14, 2005 Response, filed in connection with U.S. Appl. No. 10/631,415.
U.S. Appl. No. 10/970,761, filed Oct. 20, 2004, Frazer et al.
U.S. Appl. No. 60/566,302, filed Apr. 28, 2004, Cox et al.
U.S. Appl. No. 60/590,534, filed Jul. 22, 2004, Cox et al.
Adami, et al. (1998) "Towards an understanding of breast cancer etiology" Cancer Biology 8:255-262.
Adnane, et al. (1991) "BEK and FLG, two receptors to members of the FGF family, are amplified in subsets of human breast cancers" Onogene 6(4):659-663.
Agami (2002) "RNAi and related mechanisms and their potential use for therapy" Curr Opin Chem Biol 6:829-834.
Agundez et al. (2004) "Cytochrome P450 Gene Polymorphism and Cancer" Current Drug Metabolism 5:211-224.
AFD Eur panel-North America perlegen (www.ncbi.nlm.nih.gov/projects/SNP/snp_viewTable.cgi?pop=1371).
Amarzguioui et al. (2003) "Tolerance for mutations and chemical modifications in a siRNA" Nucl. Acids Res. 31:589-595.
The Anglian breast cancer study group, (2000) "Prevalence and penetrance of BRCA1 and BRCA2 mutations in a population-based series of breast cancer cases" British Journal of Cancer 83(10):1301-1308.
Antoniou, et al. (2003) "Average risks of breast and ovarian cancer associated with BRCA1 or BRCA2 mutations detected in case Series unselected for family history: a combined analysis of 22 studies" American Journal of Human Genetics 72:1117-1130.
Antoniou, et al. (2003) "Polygenic inheritance of breast cancer: Implications for design of association studies" Genetic Epidemiology 25:190-202.
Antoniou, et al. (2001) "Evidence for further breast cancer susceptibility genes in addition to BRCA1 and BRCA2 in a population-based study" Genetic Epidemiology 21:1-18.
Antoniou, et al. (2002) "A comprehensive model for familial breast cancer incorporating BRCA1, BRCA2 and other genes" British Journal of Cancer 86:76-83.
Antoniou, et al. (2008) "Common Breast Cancer-Predisposition Alleles are Associated with Breast Cancer Risk in BRCA1 and BRCA2 Mutation Carriers" American Journal of Human Genetics 82:937-948.
Armstrong et al. (2000) "Assessing the Risk of Breast Cancer" The New England Journal of Medicine 342(8) 564-571.
Barringer et al. (1990) "Blunt-end and single-strand ligations by *Escherichia coli* ligase: influence on an in vitro amplificationscheme" Gene 89, 117.
Bartel and Bartel (2003) "MicroRNAs: At the Root of Plant Development?" Plant Physiology 132:709-717.
Beaucage and Caruthers (1981) "Deoxynucleoside phosphoramidites—a new class of key intermediates for deoxypolynucleotide synthesis" Tetrahedron Letts., 22(20):1859-1862.
Beaucage and Iyer (1993) "The Synthesis of Modified Oligonucleotides by the Phosphoramidite Approach and Their Applications" Tetrahedron 49:6123.

(56) References Cited

OTHER PUBLICATIONS

Becker et al. (1995) "Combined mapping of AFLP and RFLP markers in barley" Mol Gen Genet 249:65.
Bird (1988) "Single-Chain Antigen-Binding Proteins" Science 242:423-426.
Blok and Kramer (1997) "Amplifiable hybridization probes containing a molecular switch" Mol Cell Probes 11:187-194.
Bonnet et al. (1999) "Thermodynamic basis of the enhanced specificity of structured DNA probes" Proc. Natl. Acad. Sci. U.S.A. 96:6171-6176.
Breast Cancer. American Cancer Society (2013) pp. 1-134. Downloaded from Cancer.org on Oct. 17, 2013.
Breast Cancer Association Consortium (2006) "Commonly Studied Single-Nucleotide Polymorphisms and Breast Cancer: Results from the Breast Cancer Association Consortium" Journal of National Cancer Institute 98:1382-1896.
Caplen et al. (2001) "Specific inhibition of gene expression by small double-stranded RNAs in invertebrate and vertebrate systems" Proc. Natl. Acad. Sci. USA 98:9742-9747.
Campbell et al. (2003) "Prohibitin 3' Untranslated Region Polymorphism and Breast Cancer Risk" Cancer Epidemiology, Biomarkers & Prevention 12:1273-1274.
Canzian, F., et al. (2006) "Polymorphisms of genes coding for insulin-like growth factor 1 and its major binding proteins, circulating levels of IGF-1 and IGFBP-3 and breast cancer risk: results from EPIC study" British Journal of Cancer 94:299-307.
Carlson, et al. (2004) "Selecting a maximally informative set of single-nucleotide polymorphisms for association analyses using linkage disequilibrium" American Journal of Human Genetics 74:106-120.
Chapman, et al. (2003) "Detecting disease associations due to linkage disequilibrium using haplotype tags: a class of tests and the determinants of statistical power" Human Heredity 56:18-31.
Chee et al. (1996) "Accessing Genetic Information with High-Density DNA Arrays" Science 274:610-614.
CHEK 2 Breast Cancer consortium (2002) "Low-penetrance susceptibility to breast cancer due to CHEK2(*)1100delC in noncarriers of BRCA1 or BRCA2 mutations" Nature Genetics 31: 55-59.
Cheng et al. (1994) "Long PCR" Nature 369:684.
Chlebowski, R., et al. (2002) "American Society of Clinical Oncology Technology Assessment of Pharmacologic Interventions for Breast Cancer Risk Reduction Including Tamoxifen, Raloxifene, and Aromatase Inhibition" Journal of Clinical Oncology 20(15):3328-3343.
Collaborative Group in Hormonal Factors in Breast Cancer (2001) "Familial breast cancer: collaborative reanalysis of individual data from 52 epidemiological studies including 58,209 women with breast cancer and 101,986 women without the disease" The Lancet 358:1389-1399.
Cote et al. (1983) "Specific inhibition of gene expression by small double-stranded RNAs in invertebrate and vertebrate systems" Proc. Natl. Acad. Sci. USA 80:2026-2030.
Cox, A., et al. (2007) "A common coding variant in CASP8 is associated with breast cancer risk" Nature Genetics 39(3):352-358.
Cui, et al. (2001) "After BRCA1 and BRCA2—what next? Multifactorial segregation analyses of three-generation, population-based Australian families affected by female breast cancer" American Journal of Human Jenetics 68:420-431.
Czauderna et al. (2003) "Structural variations and stabilising modifications of synthetic siRNAs in mammalian cells" Nucl Acids Res 31:2705-2716.
Day, et al. (1999) "EPIC-Norfolk: study design and characteristics of the cohort" British Journal of Cancer 80(1):95-103.
Db SNP ss No. 23605537 (http://www.ncbi.blm.bih.gov/projects/SNP/snp_ss.cgi?subsnp_id=23605537) Aug. 20, 2004.
Db SNP ss No. 23575498 (http://www.ncbi.nlm.nih.gov/SNP/snp_ss.cgi?subsnp_id=23575498) Aug. 20, 2004 .
Db SNP ss No. 24561224 (http://www.ncbi.nlm.nih.gov/SNP/snp_ref.cgi?rs=r83817198) Aug. 20, 2004.
Db SNP ss No. 227777675(http://www.ncbi.nlm.nih.gov/SNP/subsnp_id=22777675) Mar. 21, 2004.
Deloukas et al. (2004) "The DNA sequence and comparative analysis of human chromosome 10" Nature, 429: 375-381.
Devlin, et al. (1995) "A Comparison of Linkage Disequilibrium Measures for Fine-Scale Mapping" Genomics 29:311-322.
Doench and Sharp (2004) "Specificity of microRNA target selection in translational repression" Genes & Dev. 18:504-511.
Doench et al. (2003) "siRNAs can function as miRNAs" Genes & Dev. 17:438-442.
Dunning, et al. (1999) "A systematic review of genetic polymorphisms and breast cancer risk" Cancer Epidemiology Biomarkers & Prevention 8:843-854.
Dunning, et al. (2003) "A Transforming Growth Factor 1 Signal Peptide Variant Increases Secretion inVitro and Is Associated with Increased Incidence of Invasive Breast Cancer" Cancer Research 63:2610-2615.
Dunning, et al. (2004) "Polymorphisms Associated With Circulating Sex Hormone Levels in Postmenopausal Women" Journal of National Cancer Institute 96(12):936-945.
Dykxhoorn et al. (2003) "Killing The Messenger: Short RNAs that Silence Gene Expression" Nature Reviews Molec. and Cell Biol. 4:457-467.
Easton (1999) "How many more breast cancer predisposition genes are there?" Cancer Research 1:1-4.
Easton, D.F., (2007) "Genome-wide association study identifies novel breast cancer susceptibility loci" Nature 447:1087-1093.
Elbashir et al. (2001) "Duplexes of 21-nucleotide RNAs mediate RNA interference in cultured mammalian cells" Nature 411:494-498.
Elbashir et al. (2002) "Analysis of gene function in somatic mammalian cells using small interfering RNAs" Methods 26:199-213.
Fang et al. (1999) "Designing a Novel Molecular ,Beacon for Surface-Immobilized DNA Hybridization Studies" J. Am. Chem. Soc. 121:2921-2922.
Finnegan et al. (1996) "Reduced DNA methylation in *Arabidopsis thaliana* results in abnormal plant development". Proc Natl Acad Sci USA 93:8449-8454.
Fibroblast growth factor receptor 2, bacteria-expressed kinase, keratino dysostosis 1, crouzon syndrome, Pfeiffer syndrome, www.genecards.org/cgi-din/carddisp.pl?gene=FGFR@&search gene card for FGFR2, GC10M122473, pp. 1-17, as accessed Oct. 7, 2007.
Fodor (1997) "Massively Parallel Genomics" Science 277:393-395.
Ford, et al. (1998) "Genetic Heterogeneity and Penetrance Analysis of the BRCA1 and BRCA2 Genes in Breast Cancer Families" American Journal of Human Genetics 62:676-689.
Gail, M., et al. (1989) "Projecting individualized probabilities of developing breast cancer for white females who are being examined annually" Journal of the National Cancer Institute 81(24):1879-1886.
Gene card for FGFR2 (GC10M122473, pp. 1-17).
Goode, et al. (2001)Genetic Epidemiology 126: p. 155.
Goodchild (1990) "Conjugates of Oligonucleotides and Modified Oligonucleotides: A Review of Their Synthesis and Properties" Bioconjugate Chem. 1:165.
Guatelli et al. (1990) "Isothermal, in vitro amplification of nucleic acids by a multienzyme reaction modeled after retroviral replication" Proc Natl Acad Sci USA 87:1874.
Hannon (2002) "RNA interference" Nature 418:244 30:251.
Healey, et al. (2000) "A common variant in BRCA2 is associated with both breast cancer risk and prenatal viability" Nature Genetics 26:362-364.
Heiskanen, et al. (2001) "CGH, cDNA and tissue microarray analyses implicate FGFR2 amplification in a small subset of breast tumors" Analytical Cellular Pathology 22:229-234.
Hinds, et al. (2005) "Whole-genome patterns of common DNA variation in three human populations" Science 307:1072-1079.
Holen et al. (2003) "Similar behaviour of single-strand and double-strand siRNAs suggests they act through a common RNAi pathway" Nucl. Acids Res. 31:2401-2407.
Hirschhorn et al. (2002) "A comprehensive review of genetic association studies." Genetics in Medicine 4(2): 45-61.

(56) References Cited

OTHER PUBLICATIONS

Hsuih et al. (1997) "Novel, ligation-dependent PCR assay for detection of hepatitis C in serum" J Clin Microbiol 34:501-507.
Hunter et al. (2007) "A genome-wide association study identifies alleles in FGFR2 associated with risk of sporadic postmenopausal breast cancer" Nature Genetics (2007) 39(6):870-874.
Huse et al. (1989) "Generation of a Large Combinatorial Library of the Immunoglobulin Repertoire in Phage Lambda" Science 246:1275-1281.
Huston et al. (1988) "Protein engineering of antibody binding sites: Recovery of specific activity in an anti-digoxin single-chain Fv analogue produced in *Escherichia coli*" Proc. Natl. Acad. Sci. USA 85:5879-5883.
Hutvagner and Zamore (2002) "RNAi: nature abhors a double-strand" Curr Opin Genet & Dev 200:225-232.
Huusko, et al. (2004) "Genome-wide scanning for linkage in Finnish breast cancer families" European Journal of Human Genetics 12: 98-104.
Ioannidis (2001) "Replication validity of genetic association studies" Nature Genetics 29:306-309.
Ishibe eet al (1998) Cancer Research 58: 667-671.
Issaq et al. (2003) "SELDI-TOF MS for Diagnostic Proteomics" Analytical Chemistry 75:149A-155A.
Jang, et al. (2001) "Mutations in Fibroblast growth factor receptor 2 and fibroblast growth factor receptor 3 genes associated with human gastric and colorectal cancers" Cancer Research 61: 3541-3543.
Jorde (2000) "Linkage Disequilibrium and the Search for Complex Disease Genes" Genome Research 10:1435-1444.
Kamali-Sarvestani, et al. (2005) "Polymorphism in genes of alpha and beta tumor necrosis factors (TNF-α and TNG-β) and gamma interferon (IFN-γ) among Iranian women and breast cancer" Cancer Letters 223(1): 113-119.
Kalemi, et al. (2005) "The association of p53 mutations and p53 codon 72, Her 2 codon 655 and MTHFR C677T polymorphisms with breast cancer in Northern Greece" Cancer Letters 222(1): 57-65.
Katoh & Katoh, (2003) "FGFR2 and WDR11 are neighboring oncogene and tumor suppressor gene on human chromosome 10q26" International Journal of Oncology 22:1155-2737.
Kawasaki and Taira (2004) "Induction of DNA methylation and gene silencing by short interfering RNAs in human cells" Nature 431:211-217.
Kim et al. (2005) "Synthetic dsRNA Dicer substrates enhance RNAi potency and efficacy" Nature Biotechnology 23:222-226.
Kohler and Milstein (1975) "Continuous cultures of fused cells secreting antibody of predefined specificity" Nature 256:495-497.
Kosbor et al. (1983) "The production of monoclonal antibodies from human lymphocytes" Immunology Today 4:72.
Kriege, et al. (2003) Proceedings of the American Society of Clinical Oncology 22:A5.
Kuschel, et al. (2002) "Variants in DNA double-strand break repair genes and breast cancer susceptibility" Human Molecular Genetics 11(12):1399-1407.
Kwoh et al. (1989) "Transcription-based amplification system and detection of amplified human immunodeficiency virus type 1 with a bead-based sandwich hybridization format" Proc. Natl. Acad. Sci. USA 86:1173-1177.
Landegren et al. (1988) "A Ligase-Mediated Gene Detection Technique" Science 241: 1077-1080.
Lee, et al. (2005) "Genetic polymorphisms of ataxia telangiectasia mutated and breast cancer risk" Cancer Epidemiology, Biomarkers & Prevention 14(4):821-825.
Lean et al. (1997) Nature Genetics 17:435-438.
Leone et al. (1995) "Molecular beacon probes combined with amplification by NASBA enable homogeneous, real-time detection of RNA" Nucleic Acids Res. 26:2150-2155.
Lesueur et al. (2005) "Allelic association of the human homologue of the mouse modifier Ptprj with breast cancer" Human Molecular Genetics 14:2349.

Lichtenstein, et al. (2000) "Environmental and Heritable Factors in the Causation of Cancer—Analyses of Cohorts of Twins from Sweden, Denmark, and Finland" New England Journal of Medicine 343(2):78-85.
Listgarten et al. (2004) "Predictive Models for Breast Cancer Susceptibility from Multiple Single Nucleotide Polymorphisms" Clinical Cancer Research 10(8):2725-2737.
Liu et al. (2006) "The role of Self-Defined Race/Ethnicity in Population Structure Control" Annals of Human Genetics 70:496-505.
Lockhart (1998) "Mutant yeast on drugs" Nature Medicine 4:1235-1236.
Marras et al. (1999) "Multiplex detection of single-nucleotide variations using molecular beacons" Genet. Anal. Biomol. Eng. 14:151-156.
Martinez et al. (2002) "Single-Stranded Antisense siRNAs Guide Target RNA Cleavage in RNAi" Cell 110:563-574.
Mattick and Makunin (2005) "Small regulatory RNAs in mammals" Hum. Mol. Genet. 14:R121-R132.
McManus (2003) "MicroRNAs and cancer" Semin Cancer Biol. 13:253-288.
McManus and Sharp (2002) "Gene Silencing in Mammals by Small Interfering RNAs" Nature Reviews Genetics 3:737-747.
Meister et al. (2004) "Sequence-specific inhibition of microRNA and siRNA-induced RNA silencing" RNA 10:544-550.
Meksem et al. (1995) "A high-resolution map of the vicinity of the R1 locus on chromosome V of potato based on RFLP and AFLP markers" Mol Gen Genet 249:74.
Moffa, et al. (2'004) "Transforming potential of alternatively spliced variants of fibroblast growth factor receptor 2 in human mammary epithelial cells" Molecular Cancer Research 2(11): 643-652.
Morris et al. (2004) "Small Interfering RNA-Induced Transcriptional Gene Silencing in Human Cells" Science 305:1289-1292.
Morrison et al. (1984) "Chimeric human antibody molecules: Mouse antigen-binding domains with human constant region domains" Proc. Natl. Acad. Sci. USA 81:6851-6855.
NCBI SNP Database, Jun. 29, 2003 ref. SNP. ID: rd2981582.
Needham-VanDevanter et al. (1984) "Characterization of an adduct between CC-1065 and a defined oligodeoxynucleotide duplex" Nucleic Acids Res. 12:6159-6168.
Nelson et al. (2003) "The microRNA world: small is mighty" Trends Biochem. Sci. 28:534-540.
Neuberger et al. (1984) "Recombinant antibodies possessing novel effector functions" Nature 312:604-608.
Nishikura (2001) "A Short Primer on RNAi: RNA-Directed RNA Polymerase Acts as a Key Catalyst" Cell 107:415-418.
Patil, et al. "Blocks of Limited Haplotype Diversity Revealed by High-Resolution Scanning of Human Chromosome 21" (2001) Science 294(5547):1719-1723.
Perlegen database Nov. 24, 2008, 1-2.
Peto, et al. (1999) "Prevalence of BRCA1 and BRCA2 Gene Mutations in Patients With Early-Onset Breast Cancer" Journal of the National Cancer Institute 91(11):943-949.
Peto, et al. (2000) "High constant incidence in twins and other relatives of women with breast cancer" Nature Genetics 26:411-414.
Pharoah, et al. (2002) "Polygenic susceptibility to breast cancer and implications for prevention" Nature Genetics 31:33-36.
Pritchard, et al. (2001) "Linkage disequilibrium in humans: models and data" American Journal of Human Genetics 69:1-14.
Rehmsmeier et al. (2004) "Fast, and effective prediction of microRNA/ target duplexes" RNA 10:1507-1517.
Robins et al. (2005) "Incorporating structure to predict microRNA targets" Proc. Natl. Acad. Sci. 102:4006-4009.
Rodi et al., (2002) "A Strategy for the Rapid Discovery of Disease marker Using the MassARRAYTM System" Biotechniques 32:S62-S69.
Sapolsky et al. (1999) "High-throughput polymorphism screening and genotyping with high-density oligonucleotide arrays" Genetic Analysis: Biomolecular Engineering 14:187-192.
Sasieni (1997) "From genotypes to genes: doubling the sample size" Biometrics 53(4):1253-1261.

(56) References Cited

OTHER PUBLICATIONS

Satagopan, et al., (2002) "Two-stage designs for gene-disease association studies" Biometrics 58:163-170.
Scacheri et al. (2004) "Short interfering RNAs can induce unexpected and divergent changes in the levels of untargeted proteins in mammalian cells" Proc. Natl. Acad. Sci. USA 101:1892-1897.
Schmith et al. (2003) "Pharmacogenetics and disease genetics of complex diseases" CMLS Cell. Mol. Life Sci. 60:1636-1646).
Schramke and Allshire (2003) "Hairpin RNAs and Retrotransposon LTRs Effect, RNAi and Chromatin-Based Gene Silencing" Science 301:1069-1074.
Schwarz and Zamore (2002) "Why do miRNAs live in the miRNP?" Genes & Dev. 16:1025-1031.
Schwarz et al. (2002) "Evidence that siRNAs Function as Guides, Not Primers, in the *Drosophila* and Human RNAi Pathways" Mol. Cell 10:537-548.
Sempere et al. (2004) "Expression profiling of mammalian microRNAs uncovers a subset of brain-expressed microRNAs with possible roles in murine and human neuronal differentiation" Genome Biology 5:R13.
Service (1998) "Microchip arrays Put DNA on the Spot" Science 282:396-399.
Siolas et al. (2005) "Synthetic shRNAs as potent RNAi Triggers" Nature Biotechnology 23:227-231.
Sokol et al. (1998) "Real time detection of DNA-RNA hybridization in living cells" Proc. Natl. Acad. Sci. U.S.A. 95:11538-11543.
Sooknanan and Malek (1995) "NASBA" Biotechnology 13: 563-564.
Sprecher Institute "Breast Cancer in Women from Different Racial/Ethnic Groups Fact Sheet #47" Apr. 2003 envirocancer.cornell.edu/Factsheet/general/fs47.ethnicity.cfm.
Spurdle et al. "Prohibitin 3' untranslated region polymorphism and breast cancer risk in Australian women" Lancet (2002) 360:925-26.
Stacey, S., et al. (2008) "Common variants on chromosome 5p12 confer susceptibility to estrogen receptor-positive breast cancer" Nature Genetics 40(6):703-706.
Stacey, S., et al. (2007) "Common variants on chromosomes 2q35 and 16q12 confer susceptibility to estrogen receptor-positive breast cancer" Nature Genetics 39(7):865-869.
Stankovic, et al. (1998) "ATM mutations and phenotypes in ataxia-telangiectasia families in the British Isles: expression of mutant ATM and the risk of leukemia, lymphoma, and breast cancer" American Journal of Human Genetics 62:334-345.
Stark et al. (2003) "Identification of *Drosophila* MicroRNA Targets" PLoS Biol. 1:E60.
Stephens, et al. (2005) "A screen of the complete protein kinase gene family identifies diverse patterns of somatic mutations in human breast cancer" Nature Genetics 37:590-592 and supplemental information.
Takashi et al. (2001) "3. Byouti Kaiseki to SNP 1 Gan (Pathologic Analysis and SNP, 1 Cancer)", Ketsueki/Meneki/Shuyou, 6(4):353-359.
Takeda et al. (1985) "Construction of chimaeric processed immunoglobulin genes containing mouse variable and human constant region sequences" Nature 314:452-454.
Tang et al. (2003) "A biochemical framework for RNA silencing in plants" Genes & Dev. 17:49-63.
Tang et al. (2005) "Genetic structure, self-identified race. Ethnicity and confounding in case-control association studies" Am. J. Hum. Genet. 76(2):268-275.
Tannheimer, et al. (2000) "Characterization of fibroblast growth factor receptor 2 overexpression in the human breast cancer cell line SUM-52PE" Breast Cancer Research 2:311-320.
Thompson, et al. (2002) "Evaluation of linkage of breast cancer to the putative BRCA3 locus on chromosome 13q21 in 128 multiple case families from the Breast Cancer Linkage Consortium" Proceedings of the National Academy of Sciences USA 99(2):827-831.
Tischkoff, et al. (2004) "Implications of biogeography of human populations for 'race' and medicine" Nature Genetics 36:s21-s27.

Titus-Ernstoff, et al. (1998) "Menstrual factors in relation to breast cancer risk" Cancer Epidemiology, Biomarkers & Prevention 7:783-789.
Tuschl and Borkhardt (2002) "Small Interfering RNAs: A revolutionary Tool for the Analysis of Gene Function and Gene Function and Gene Therapy" Molecular Interventions 2:158-167.
Tyagi and Kramer (1996) "Molecular Beacons: Probes that Fluoresce upon Hybridization" Nature Biotechnology 14:303-308.
Tyagi et al. (1998) "Multicolor molecular beacons for allele discrimination" Nature Biotechnology 16:49-53.
Uhlmann and Peyman (1990) "Antisense Oligonucleotides: A New Therapeutic Principle" Chem. Rev. 90:543.
Van't Veer et al. (2002) "Gene expression profiling predicts clinical outcome of breast cancer" Nature: International Weekly Journal of Science 415(6871):530-536.
Van de Vijver et al. (2002) "A Gene-expression signature as a predictor of survival in breast cancer" New England Journal of Medicine 347(25): 1999-2009.
Vet et al. (1999) "Multiplex detection of four pathogenic retroviruses using molecular beacons" Proc. Natl. Acad. Sci. U.S.A. 96:6394-6399.
Vos et al. (1995) "AFLP: a new technique for DNA fingerprinting" Nucl Acids Res 23:4407.
Wang et al. (2004) Cancer Research 64:64-71.
Ward et al. (1989) "Binding activities of repertoire of single immunoglobulin variable domains secreted from *Echerichia coli*" Nature 334:544-546.
Wall, et al. (2003) "Haplotype blocks and linkage disequilibrium in the human genome" Nature Reviews Genetics 4:587-597.
Wu and Wallace (1989) "The Ligation Amplification Reaction (LAR)-Amplification for Specific DNA Sequences Using Sequential Rounds of Template-Dependent Ligation" Gene 4: 560.
Zamore (2001) "RNA interference: listening to the sound of silence" Nature Structural Biology 8:746-750.
Zeng et al. (2003) "MicroRNAs and small interfering RNAs can inhibit mRNA expression by similar mechanisms" Proc. Natl. Acad. Sci. USA 100:9779-9784.
Zhang et al. (1999) "Automated and Integrated System for High-Throughput DNA Genotyping Directly from Blood" Anal. Chem. 71:1138-1145.
Zhang, et al. (2002) "A dynamic programming algorithm for haplotype block partitioning" Proceedings of the National Academy of Sciences USA 99(11):7335-7339.
www.hhs.gov/myhealthcare/glossray/glossary.html p. 1 Jul. 11, 2008.
Advani and Morena-Aspitia (2014) Breast Cancer: Targets & Therapy; 6: 59-71 (Exhibit 1).
Ahmed et al., "Newly discovered breast cancer susceptibility loci on 3p24 and 17q23.2" Nature Genetics (2009) 41(5):585-590 (Exhibit 2).
American Cancer Society: (2013) Breast Cancer Facts & Figures 2013-2014. Atlanta (GA), American Cancer Society Inc, 12 (Exhibit 3).
Antoniou et al., "The BOADICEA model of genetic susceptibility to breast and ovarian cancer" British Journal of Cancer (2004) 91, 1580-1590 (Exhibit 4).
Antoniou et al., "Common variants in LSP1, 2q25 and 8q24 and breast cancer risk for BRCA1 and BRCA2 mutation carriers" Human Genetics (2009) 18(22):4442-4456 (Exhibit 5).
Bonnen et al. (2002), Haplotype and Linkage Disequilibrium Architecture for Human Cancer-Associated Genes, Genome Research, 12:1846-1853 (Exhibit 6).
Bondy et al. (1994) "Validation of a Breast Cancer Risk Assessment Model in Women With a Positive Family History" Journal of the National Cancer Institute, vol. 86, No. 8, pp. 620-625 (Exhibit 7).
"Breast cancer breakthrough", <URL http://au.news.yahoo.com/today-tonight/health/article/-/13691294/breast-cancer-breakthrough> published on May 15, 2012 (Exhibit 8).
Brentall et al. (2014) British Journal of Cancer 110: 827-828 (Exhibit 9).
Chen et al. (2004) Stat Appl Genet Mol Biol. 3: Article 21 (Exhibit 10).

(56) References Cited

OTHER PUBLICATIONS

Chlebowski et al., "Predicting Risk of Breast Cancer in Postmenopausal Women by Hormone Receptor Status" J Natl Cancer Inst (2007) 99:1695-1705 (Exhibit 11).
Claus et al. (1991) Am J Hum Genet. 48: 232-242 (Exhibit 12).
Claus et al. (1993) Breast Cancer Res Treat. 28: 115-120 (Exhibit 13).
Claus et al., "Autosomal Dominant Inheritance of Early-Onset Breast Cancer" Cancer (1994) 73(3):643-651 (Exhibit 14).
Claus et al., "Effect of BRCA1 and BRCA2 on the Association Between Breast Cancer Risk and Family History" Journal of the National Cancer Institute (1998) 90(23):1824-1829 (Exhibit 15).
Cook et al., "The Effect of Including C-Reactive Protein in Cardiovascular Risk Prediction Models for Women" Annals of Internal Medicine (2006) 145:21-29 (Exhibit 16).
Costantino et at., "Validation Studies for Models Projecting the Risk of Invasive and Total Breast Cancer Incidence" J Natl Cancer Inst (1999) 91:1541-8 (Exhibit 17).
Darabi et al. (2012) Breast Cancer Research 14: R25 (Exhibit 18).
De la Cruz (2014) Prim Care Clin Office Pract; 41: 283-306 (Exhibit 19).
Dite et al. (2013) Breast Cancer Res Treat. 139: 887-896 (Exhibit 20).
Dite, G. et al., "Value of adding single-nucleotide polymorphism panel markers to phenotypic algorithms of breast cancer risk", Cancer Research, May 2015, vol. 75, No. 9 suppl. 1, abstract No. P6-09-05 (Exhibit 21).
Dite et al. "Breast cancer risk prediction using clinical models and 77 independent risk-associated SNPs for women aged under 50 years: Australian Breast Cancer Family Registry." Cancer Epidemiology Biomarkers & Prevention 25.2 (2016): 359-365 (Exhibit 22).
Evans et al., "A new scoring system for the chances of identifying a BRCA1/2 mutation outperforms existing models including BRCAPRO" J Med Genet (2004) 41:474-480 (Exhibit 23).
Fodor (1997a) FASEB Journal 11:A879 (Exhibit 24).
Fodor (1997b) Science 277: 393-395 (Exhibit 25).
Gail et al., "Weighing the Risks and Benefits of Tamoxifen Treatment for Preventing Breast Cancer" J Natl Cancer Inst (1999) 91:1829-46 (Exhibit 26).
Gail et al., "Projecting Individualized Absolute Invasive Breast Cancer Risk in African American Women" J Natl Cancer Inst (2007) 99:1782-92 (Exhibit 27).
Gail, "Discriminatory Accuracy From Single-Nucleotide Polymorphisms in Models to Predict Breast Cancer Risk" J Natl Cancer Inst (2008) 100:1037-1041 (Exhibit 28).
Gail, "Value of Adding Single-Nucleotide Polymorphism Genotypes to a Breast Cancer Risk Model" J Natl Cancer Inst (2009) 101:959-963 (Exhibit 29).
Garcia (2004) Pediatrics 113:1394 (Exhibit 30).
Gold et al., "Genome-wide association study provides evidence for a breast cancer risk locus at 6q22.33" PNAS (2008) 105(11):4340-4345 (Exhibit 31).
Hanks et al., Genome Biology (vol. 4, p. 11 published Apr. 29, 2003) (Exhibit 32).
Ho et al. (2013) The Malaysian Journal of Pathology 1: 33-43 (Exhibit 33).
Huusko et al., European Journal of Human Genetics—12:256-256 (2003) (Exhibit 34).
Jonker et al., "Modeling Familial Clustered Breast Cancer Using Published Data" Cancer Epidemiology, Biomarkers & Prevention (2003) 12:1479-1485 (Exhibit 35).
Jupe et al. (2007) "The OncoVue (R) model for predicting breast cancer risk" Breast Cancer Research and Treatment vol. 106 No. Suppl. 1, p. S179 (Exhibit 36).
Kelemen et al., "Genetic Variation in the Chromosome 17q23 Amplicon and Breast Cancer Risk" Cancer Epidemiol Biomarkers Prev (2009) 18(6):1864-8 (Exhibit 37).
Kohno et al (2001), Medical Online 6:25-31 (Exhibit 38).

Kostrikis, "Spectral genotyping of human alleles" Science 279.5354 (1998): 1228+. Expanded Academic ASAP. Web. Oct. 18, 2010, pp. 1-4 (Exhibit 39).
Lee, et al. (2005) "Genetic polymorphisms of ataxia telangiectasia mutated and breast cancer risk" Cancer Epidemiology, Biomarkers & Prevention 14(4):821-825 (Exhibit 40).
Lee et al. (Cancer Epidemiol Biomakers Prve Jan. 2008 vol. 17 p. 258) (Exhibit 41).
Mackarem et al. (2001) The Breast Journal 2001 vol. 7 p. 34 (Exhibit 42).
Mahoney et al. (2008) Cancer J Clin; 58: 347-371 (Exhibit 43).
Matsuno et al. (2011) "Projecting Individualized Absolute Invasive Breast Cancer Risk in Asian and Pacific Islander American Women" J Natl Cancer Inst 2011;103:951-961 (Exhibit 44).
Maxwell et al. (2013), "Common breast cancer risk variants in the post-COGS era: a comprehensive review", Breast Cancer Research, 15:212 (Exhibit 45).
Mazzola et al. (2014) Cancer Epidemiol Biomarkers Prev. 23: 1689-1695 (Exhibit 46).
Mealiffe et al., "Assessment of Clinical Validity of a Breast Cancer Risk Model Combining Genetic and Clinical Information" J Natl Cancer Inst (2010) 102:1618-1627 (Exhibit 47).
Merriam-Webster Dictionary definition for "Caucasian," available from www.merriam-webster.com/medical/Caucasian, accessed Nov. 2, 2012 (Exhibit 48).
Milliken et al., Cancer Epidemiology, Biomarkers and Prevention 2005 vol. 14 p. 2326) (Exhibit 49).
Parmigiani et al. (1998) Am J Hum Genet. 62: 145-158 (Exhibit 50).
Parmigiani et al. (2007) Ann Intern Med. 1479: 441-450 (Exhibit 51).
Pencina et al., "Evaluating the added predictive ability of a new marker: From area under the ROC curve to reclassification and beyond" Statistics in Medicine (2008) 27:157-172 (Exhibit 52).
Pepe and Janes, "Gauging the Performance if SNPs, Biomarkers, and Clinical Factors for Predicting Risk of Breast Cancer" J Natl Cancer Inst (2008) 100(14):978-979 (Exhibit 53).
Pharoah et al., "Polygenes, Risk Prediction, and Targeted Prevention of Breast Cancer" N Eng J Med (2008) 358:2796-803 (Exhibit 54).
Pharoah et al. (2004), Association Studies for Finding Cancer-Susceptibility Genetic Variants, Nature Reviews, 4:850-860 (Exhibit 55).
Ponder et al. (2005), Polygenic Inherited Predisposition to Breast Cancer, Cold Spring Harbor Symposia on Quantitative Biology, vol. LXX, p. 35-41 (Exhibit 56).
"Perlegen Builds Commercial Group to Support Upcoming MammaPLUS(TM) Launch" Evaluatepharma Press Release, Apr. 28, 2009, http://www.evaluatepharma.com/Universal/View.aspx?type=Story&id=184247 (Exhibit 57).
"Perlegen Introduces BRAVAGenTM Breast Cancer Risk Stratification Test" Medical News Today, Sep. 24, 2009, http://www.medicalnewstoday.com/releases/165123.php(Exhibit 58).
Radford et al. (1995) Cancer Research (55) pp. 5180-5183) (Exhibit 59).
Raskin et al. (2008) Cancer Epidemiol Biomarkers Prey Vo. 17 p. 1060 (Exhibit 60).
Rockhill et al., "Validation of the Gail et al. Model of Breast Cancer Risk Prediction and Implications for Chemoprevention" J Natl Cancer Inst (2001) 93:358-66 (Exhibit 61).
Ruiz-Narvaez (2010) Breast Cancer Res Treat vol. 123 p. 525 (Exhibit 62).
Saslow et al. (2007) CA Cancer J Clin. 57: 75-89 (Exhibit 63).
Schwartz (2001) N. Engl. J. Med. 344(18):1392-1393 (Exhibit 64).
Schonfeld et al. (2010) "Effect of Changing Breast Cancer Incidence Rates on the Calibration of the Gail Model" J Clin Oncol 28, pp. 1-8 (Exhibit 65).
Service et al., "Coming Soon: The Pocket DNA Sequencer" Science 282.5388 (1998): 399. Expanded Academic ASAP. Web. Sep. 28, 2010 pp. 1-3 (Exhibit 66).
Slatkin and Excoffier, "Testing for linkage disequilibrium in genotypic data using the Expectation-Maximization algorithm" Heredity (1996) 76, 377-383 (Exhibit 67).

(56) References Cited

OTHER PUBLICATIONS

Spiegelman et al. (1994) "Validation of the Gail et.al. Model for Predicting Individual Breast Cancer Risk" Journal of the National Cancer Institute 68(8):600-607 (Exhibit 68).
Sorlie et al. (2001) Proc. Natl. Acad. Sci., 98: 10869-10874 (Exhibit 69).
Thomas et al., "A multistage genome-wide association study in breast cancer identifies two new risk alleles at 1p11.2 and 14q24.1 (RAD51L1)" Nature Genetics (2009) 41(4):579-584 (Exhibit 70).
Turnbull et al., "Genome-wide association study identifies five new breast cancer susceptibility loci" Nature Genetics (2010) 42(6):504-507 and Online Methods (Exhibit 71).
Tyrer et al., "A breast cancer prediction model incorporating familial and personal risk factors" Statistics in Medicine (2004) 23:1111-1130 (Exhibit 72).
Van Asperen et al., "Risk Estimation for Healthy Women from Breast Cancer Families: New Insights and New Strategies" Cancer Epidemiology, Biomarkers & Prevention (2004) 13, 87-93 (Exhibit 73).
Van Brunt, "Amplifying Genes: PCT and its Alternatives" Bio/Technology (1990) 8, pp. 291, 292 and 294 (Exhibit 74).
Visvanathan et al. (2009) Journal of Clinical Oncology. 27: 3235-3258 (Exhibit 75).
WIRES: Questions and Answers. "Average risk of breast cancer and general information" (Exhibit 76).
Zheng et al. (2010) "Genetic and Clinical Predictors for Breast Cancer Risk Assessment and Stratification Among Chinese Women" Journal of the National Cancer Institute 102(13):972-981 (Exhibit 77).
*Enfish, LLC* v. *Microsoft Corp.*, No. 2015-1244 (Fed. Cir. May 12, 2016) (Exhibit 78).
NCBI SNP Database ss 23920837 (rs889312), http://www.ncbi.nlm.nih.gov/projects/SNP/snp_ref.cgi?rs=889312, downloaded Aug. 20, 2004 (Exhibit 79).
May 19, 2016 Memorandum from USPTO Deputy Commissioner for Patent Examination Policy to the Patent Examining Corps (Exhibit 80).
May 5, 2011 Office Action issued in connection with U.S. Appl. No. 12/890,272 (Exhibit 1).
Jun. 3, 2011 Response filed in connection with U.S. Appl. No. 12/890,272 (Exhibit 2).
Jul. 8, 2011 Response, filed in connection with U.S. Appl. No. 12/890,272 (Exhibit 3).
Sep. 29, 2011 Office Action issued in connection with U.S. Appl. No. 12/890,272 (Exhibit 4).
Mar. 29, 2012 Response filed in connection with U.S. Appl. No. 12/890,272 (Exhibit 5).
Apr. 2, 2012 Applicant-Initiated Interview Summary issued in connection with U.S. Appl. No. 12/890,272 (Exhibit 6).
Apr. 23, 2012 Office Action issued in connection with U.S. Appl. No. 12/890,272 (Exhibit 7).
May 24, 2012 Response filed in connection with U.S. Appl. No. 12/890,272 (Exhibit 8).
May 24, 2012 Applicant-Initiated Interview Summary issued in connection with U.S. Appl. No. 12/890,272 (Exhibit 9).
Jun. 1, 2012 Response filed in connection with U.S. Appl. No. 12/890,272 (Exhibit 10).
Jun. 26, 2012 Response filed in connection with U.S. Appl. No. 12/890,272 (Exhibit 11).
Aug. 23, 2012 Office Action issued in connection with U.S. Appl. No. 12/890,272 (Exhibit 12).
Nov. 16, 2012 Applicant-Initiated Interview Summary, including attached Oct. 26, 2012 facsimile, issued in connection with U.S. Appl. No. 12/890,272 (Exhibit 13).
Nov. 21, 2012 Response filed in connection with U.S. Appl. No. 12/890,272 (Exhibit 14).
Jan. 9, 2013 Office Action issued in connection with U.S. Appl. No. 12/890,272 (Exhibit 15).
Feb. 13, 2013 Applicant-Initiated Interview Summary issued in connection with U.S. Appl. No. 12/890,272 (Exhibit 16).
Mar. 8, 2013 Response filed in connection with U.S. Appl. No. 12/890,272 (Exhibit 17).
Mar. 5, 2013 Applicant-Initiated Interview Summary, including attached Proposed Amendments to the Claims, issued in connection with U.S. Appl. No. 12/890,272 (Exhibit 18).
Jun. 20, 2013 Advisory Action issued in connection with U.S. Appl. No. 12/890,272 (Exhibit 19).
Jul. 9, 2013 Response filed in connection with U.S. Appl. No. 12/890,272 (Exhibit 20).
Jul. 10, 2013 Interview Summary issued in connection with U.S. Appl. No. 12/890,272 (Exhibit 21).
Dec. 18, 2013 Office Action issued in connection with U.S. Appl. No. 12/890,272 (Exhibit 22).
Feb. 4, 2014 Applicant-Initiated Interview Summary issued in connection with U.S. Appl. No. 12/890,272 (Exhibit 23).
Feb. 21, 2014 Response filed in connection with U.S. Appl. No. 12/890,272 (Exhibit 24).
Oct. 20, 2014 Office Action issued in connection with U.S. Appl. No. 12/890,272 (Exhibit 25).
Dec. 5, 2014 Applicant-Initiated Interview Summary issued in connection with U.S. Appl. No. 12/890,272 (Exhibit 26).
Jan. 12, 2015 Response filed in connection with U.S. Appl. No. 12/890,272 (Exhibit 27).
Apr. 24, 2015 Notice of Allowance issued in connection with U.S. Appl. No. 12/890,272 (Exhibit 28).
Jun. 11, 2012 Office Action issued in connection with U.S. Appl. No. 12/920,815 (Exhibit 29).
Jul. 11, 2012 Response filed in connection with U.S. Appl. No. 12/920,815 (Exhibit 30).
Sep. 21, 2012 Office Action issued in connection with U.S. Appl. No. 12/920,815 (Exhibit 31).
Feb. 21, 2013 Response filed in connection with U.S. Appl. No. 12/920,815 (Exhibit 32).
Jun. 24, 2013 Office Action issued in connection with U.S. Appl. No. 12/920,815 (Exhibit 33).
Dec. 23, 2013 Response filed in connection with U.S. Appl. No. 12/920,815 (Exhibit 34).
Apr. 20, 2015 Office Action issued in connection with U.S. Appl. No. 12/920,815 (Exhibit 35).
Oct. 20, 2015 Response filed in connection with U.S. Appl. No. 12/920,815 (Exhibit 36).
Jun. 14, 2016 Office Action issued in connection with U.S. Appl. No. 12/920,815 (Exhibit 37).
Dec. 14, 2016 Response filed in connection with U.S. Appl. No. 12/920,815 (Exhibit 38).
Jun. 19, 2017 Office Action issued in connection with U.S. Appl. No. 12/920,815 (Exhibit 39).
May 23, 2017 Supplemental Response filed in connection with U.S. Appl. No. 12/920,815 (Exhibit 40).
Mar. 22, 2017 Applicant-Initiated Interview Summary issued in connection with U.S. Appl. No. 12/920,815 (Exhibit 41).
Mar. 11, 2016 Supplemental Response filed in connection with U.S. Appl. No. 12/920,815 (Exhibit 42).
Mar. 7, 2016 Examiner-Initiated Interview Summary issued in connection with U.S. Appl. No. 12/920,815 (Exhibit 43).
Jan. 20, 2016 Examiner-Initiated Interview Summary issued in connection with U.S. Appl. No. 12/920,815 (Exhibit 44).
Dec. 18, 2015 Summary dated Nov. 12, 2015 Examiner Interview filed in connection with U.S. Appl. No. 12/920,815 (Exhibit 45).
Nov. 18, 2015 Applicant-Initiated Interview Summary issued in connection with U.S. Appl. No. 12/920,815 (Exhibit 46).
Feb. 4, 2013 Applicant-Initiated Interview Summary issued in connection with U.S. Appl. No. 12/920,815 (Exhibit 47).
Feb. 4, 2014 Applicant-Initiated Interview Summary issued in connection with U.S. Appl. No. 12/370,972 (Exhibit 48).
Aug. 11, 2016 Office Action issued in connection with U.S. Appl. No. 15/133,055 (Exhibit 49).
Nov. 11, 2016 Response filed in connection with U.S. Appl. No. 15/133,055 (Exhibit 50).
Feb. 14, 2017 Office Action issued in connection with U.S. Appl. No. 15/133,055 (Exhibit 51).
Jun. 13, 2017 Response filed in connection with U.S. Appl. No. 15/133,055 (Exhibit 52).

(56) References Cited

OTHER PUBLICATIONS

Jun. 14, 2017 Notice of Appeal filed in connection with U.S. Appl. No. 15/133,055 (Exhibit 53).
Jul. 17, 2017 Notice of Panel Decision from Pre-Appeal Brief Review issued in connection with U.S. Appl. No. 15/133,055 (Exhibit 54).
Jul. 19, 2017 Advisory Action issued in connection with U.S. Appl. No. 15/133,055 (Exhibit 55).
Nov. 15, 2017 Response filed in connection with U.S. Appl. No. 15/133,055 (Exhibit 56).
Jul. 19, 2018 Office Action issued in connection with U.S. Appl. No. 15/133,055 (Exhibit 57);.
Nov. 19, 2018 Response dated Jul. 19, 2018 Office Action issued in connection U.S. Appl. No. 15/133,055 (Exhibit 58).
Nov. 30, 2018 Office Action issues in connection with U.S. Appl. No. 15/814,255 (Exhibit 59).
PCT International Search Report dated Dec. 6, 2007 in connection with PCT International Application No. PCT/US2006/045812, filed Nov. 29, 2006 (Exhibit 71).
PCT International Search Report dated Dec. 8, 2015 in connection with International Application No. PCT/AU2015/050583 (Exhibit 72).
International Preliminary Report on Patentability, dated Dec. 6, 2011, in connection with PCT International Application No. PCT/AU2010/000675 (Exhibit 73).
International Search Report, dated Aug. 13, 2010 in connection with PCT International Application No. PCT/AU2010/000675 (Exhibit 74).
Patent Examination Report No. 1, dated Oct. 9, 2012 in connection with Australian Patent Application No. 2010256343 (Exhibit 75).
European Search Opinion, dated Oct. 18, 2012 in connection with European Patent Application No. 10782820.4 (Exhibit 76).
Extended European Search Report, dated Oct. 18, 2012 in connection with European Patent Application No. 10782820.4 (Exhibit 77).
Apr. 9, 2018 Extended European Search Report issued by the European Patent Office (EPO) in connection with European Patent Application No. 15847907.1 (Exhibit 78).
Cuzick et al. (2014) "Use of a SNP panel to refine risk estimates in women at high risk of breast cancer: Results from two randomized tamoxifen prevention trials", J. Clin. Oncol. 32(5s):suppl; abstr 1519 (Exhibit 79).
Ellis et al. (2006) "Localization of Breast Cancer Susceptibility Loci by Genome-Wide SNP Linkage Disequilibrium Mapping", Genet. Epidemiol. 30(1):48-61 (Fifth IDS filed Apr. 12, 2018) (Exhibit 80).
Kaklamani et al. (2013) "Adiponectin pathway polymorphisms and risk of breast cancer in African Americans and Hispanics in the Women's Health Initiative", Breast Cancer Res Treat. 139(2):461-468 (Exhibit 81).
McCarthy et al. (2013) "Incremental impact of breast cancer SNP panel on risk classification in a screening population of white and African American women", Breast Cancer Res Treat. 138(3):889-898 (Exhibit 82).
Response filed to Japanese Office Action dated Aug. 24, 2012 in connection with Japanese Patent Application No. 2008/543446, including English Language claims (Exhibit 83).
Feb. 26, 2019 Final Office Action issued in connection with U.S. Appl. No. 15/133,055 (Exhibit 84).

\* cited by examiner

| SNP_ID | REFSNP_ID | SUBSNP_ID | ACCESSION_ID | POSITION | ALLELE 1 | ALLELE 2 | Ptrend_weighted | gene_name | geneDescription | HIT_TYPE |
|---|---|---|---|---|---|---|---|---|---|---|
| 2312116 | 2981582 | 23605537 | NC_000010.8 | 123342307 | A | G | 4.60326E-17 | FGFR2 | fibroblast growth factor receptor 2 | intron |
| 1622530 | 1318703 | 23749706 | NC_000016.8 | 7093693 | C | T | 4.0897E-08 | A2BP1 | ataxin 2-binding protein 1 | intron |
| 3712013 | 12443621 | 23555306 | NC_000016.8 | 51105538 | A | G | 8.51988E-08 | TNRC9 | trinucleotide repeat containing 9 | intron |
| 1509710 | 3857481 | 24457601 | NC_000006.9 | 87181288 | G | A | 1.87727E-07 | | | |
| 843029 | 889312 | 23920837 | NC_000005.8 | 56067641 | C | A | 3.91762E-07 | | | |
| 1990126 | 13281615 | 23575498 | NC_000008.9 | 128424800 | A | G | 6.71233E-07 | | | |
| 604819 | 2107425 | 24118127 | NC_000011.8 | 1977651 | C | T | 1.52872E-06 | H19 | imprinted maternally expressed untranslated mRNA | intron |
| 3025734 | 2314099 | 23293611 | NC_000004.9 | 162587067 | T | G | 1.5677E-06 | FSTL5 | follistatin-like 5 | intron |
| 1152499 | 3817198 | 24561224 | NC_000011.8 | 1865582 | T | C | 1.68472E-06 | LSP1 | lymphocyte-specific protein 1 | intron |
| 4415909 | 4666451 | 24628838 | NC_000002.9 | 19208571 | G | A | 1.96102E-06 | LOC388927 | LOC388927 | intron |
| 1732681 | 2049621 | 23524035 | NC_000011.8 | 95067936 | G | C | 2.47234E-06 | | | |
| 4281579 | 4841365 | 24407799 | NC_000008.9 | 10425908 | G | C | 3.31814E-06 | UNQ9391 | tryptophan/serine protease | intron |
| 4454457 | 7313833 | 23714202 | NC_000012.9 | 27974463 | G | A | 3.40399E-06 | | | |
| 2616199 | 981782 | 24429196 | NC_000005.8 | 45321475 | A | C | 3.42446E-06 | HCN1 | hyperpolarization activated cyclic nucleotide-gated potassium channel 1 | intron |
| 1720694 | 11235127 | 23790209 | NC_000011.8 | 86766192 | G | A | 8.83338E-06 | | | |
| 4077723 | 6463266 | 24343132 | NC_000007.11 | 4926524 | G | T | 9.99002E-06 | LOC441192 | | |

Fig. 1

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3711990 | 8051542 | 24530965 | NC_000016.8 | 51091668 | T | C | 1.11036E-05 | TNRC9 | trinucleotide repeat containing 9 | intron |
| 3337858 | 12658840 | 23928828 | NC_000005.8 | 160251566 | A | G | 1.19405E-05 | | | |
| 4093095 | 6469633 | 23343761 | NC_000008.9 | 117205405 | T | C | 1.28115E-05 | | | |
| 4213825 | 7443644 | 23179775 | NC_000005.8 | 29282566 | C | T | 1.49811E-05 | | | |
| 3488617 | 3852789 | 24110311 | NC_000016.8 | 70786007 | A | C | 1.52607E-05 | | | |
| 3610210 | 16998733 | 23731751 | NC_000004.9 | 149695013 | T | C | 1.67319E-05 | NR3C2 | nuclear receptor subfamily 3, group C, member 2 | intron |
| 3451239 | 6843340 | 24659372 | NC_000004.9 | 48460865 | C | T | 1.72313E-05 | KIAA0826 | KIAA0826 protein | intron |
| 1582533 | 17157070 | 24001013 | NC_000007.11 | 108946886 | A | G | 1.74197E-05 | | | |
| 3488150 | 13110927 | 24667925 | NC_000004.9 | 169674258 | T | C | 3.30775E-05 | FLJ31033 | similar to hypothetical protein FLJ20035 | exon |
| 2770052 | 30099 | 23984516 | NC_000005.8 | 52454339 | G | A | 5.25187E-05 | | | |
| 4141351 | 7307700 | 23482623 | NC_000012.9 | 124113077 | G | A | 8.18526E-05 | AACS | acetoacetyl-CoA synthetase | intron |
| 1335030 | 4954956 | 23868773 | NC_000002.9 | 139378309 | C | T | 0.00071933 | | | |
| 2211665 | 10508468 | 24570315 | NC_000010.8 | 139958759 | T | C | 0.00114007 | FRMD4A | FERM domain containing 4A | intron |
| 4538418 | 2298075 | 24488770 | NC_000010.8 | 102237398 | C | A | 0.12570628 | SEC31L2 | SEC31-like 2 (S. cerevisiae) | exon |

Fig. 1 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 2312116 | 2981582 | 23605537 | NC_000010.8 | 123342307 | A | G | 4.60326E-17 | FGFR2 | fibroblast growth factor receptor 2 | intron |
| 4415909 | 4666451 | 24628838 | NC_000002.9 | 19208571 | G | A | 1.96102E-06 | LOC388927 | LOC388927 | intron |
| 1622530 | 1318703 | 23749706 | NC_000016.8 | 7093693 | C | T | 4.0897E-08 | A2BP1 | ataxin 2-binding protein 1 | intron |
| 3712013 | 12443621 | 23553306 | NC_000016.8 | 51105538 | A | G | 8.51988E-08 | TNRC9 | trinucleotide repeat containing 9 | intron |
| 3564092 | 16946255 | 23513100 | NC_000015.8 | 61089362 | A | G | 9.9596E-08 | TPM1 | tropomyosin 1 (alpha) | 30kb up |
| 1509710 | 3857481 | 24457601 | NC_000006.9 | 87181288 | G | A | 1.87727E-07 | | | |
| 1990126 | 13281615 | 23575498 | NC_000008.9 | 128424800 | A | G | 6.71233E-07 | | | |
| 843029 | 889312 | 23920837 | NC_000005.8 | 56067641 | C | A | 3.91762E-07 | | | |
| 1990093 | 10956364 | 24545864 | NC_000008.9 | 128448065 | C | T | 6.21205E-07 | | | |
| 469090 | 961928 | 24346810 | NC_000007.11 | 78118242 | C | T | 8.29847E-07 | AIP1 | atrophin-1 interacting protein 1 | intron |
| 843015 | 1910020 | 23920768 | NC_000005.8 | 56062257 | T | C | 1.12234E-06 | | | |
| 604819 | 2107425 | 24118127 | NC_000011.8 | 1977651 | C | T | 1.52872E-06 | H19 | imprinted maternally expressed untranslated mRNA | intron |
| 1152499 | 3817198 | 24561224 | NC_000011.8 | 1865582 | T | C | 1.68472E-06 | LSP1 | lymphocyte-specific protein 1 | intron |
| 1732681 | 2049621 | 23524035 | NC_000011.8 | 95067936 | G | C | 2.47234E-06 | | | |
| 2312090 | 3750817 | 24103328 | NC_000010.8 | 123322567 | C | T | 2.7826E-06 | FGFR2 | fibroblast growth factor receptor 2 | intron |
| 4281579 | 4841365 | 24407799 | NC_000008.9 | 104259908 | G | C | 3.31814E-06 | UNQ9391 | tryptophan/serine protease | intron |
| 3712118 | 3112624 | 23555885 | NC_000016.8 | 51184052 | A | G | 3.35309E-06 | | | |

Fig. 2

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 4454457 | 7313833 | 23714202 | NC_000012.9 | 27974463 | G | A | 3.40399E-06 | PTHLH | parathyroid hormone-like hormone | 100kb down |
| 2616199 | 981782 | 24429196 | NC_000005.8 | 45321475 | A | C | 3.42446E-06 | HCN1 | hyperpolarization activated cyclic nucleotide-gated potassium channel 1 | intron |
| 332079 | 12529349 | 23945007 | NC_000006.9 | 52038396 | T | G | 3.88017E-06 | PKHD1 | polycystic kidney and hepatic disease 1 (autosomal) | intron |
| 4080071 | 6944999 | 24381432 | NC_000007.11 | 70244514 | C | T | 0.020080291 | WBSCR17 | Williams-Beuren syndrome chromosome region 17 | intron |
| 3712111 | 3104793 | 23556160 | NC_000016.8 | 51198687 | T | C | 4.56599E-06 | | | |
| 2211665 | 10508468 | 24570315 | NC_000010.8 | 139587591 | T | C | 0.001140007 | FRMD4A | FERM domain containing 4A | intron |
| 4181115 | 2463083 | 24560263 | NC_000019.8 | 23570973 | C | T | 0.001638633 | LOC440520 | similar to ribosomal protein S27 | intron |
| 4181115 | 2463083 | 24560263 | NC_000019.8 | 23570973 | C | T | 0.001638633 | LOC390908 | similar to Zinc finger protein 43 (Zinc protein HTF6) (Zinc finger protein KOX27) | up |
| 3488150 | 13110927 | 24667925 | NC_000004.9 | 169674258 | T | C | 3.307775E-05 | FLJ31033 | similar to hypothetical protein FLJ20035 | exon |
| 1720694 | 11235127 | 23790209 | NC_000011.8 | 86766192 | G | A | 8.83338E-06 | | | |
| 1335030 | 4954956 | 23868773 | NC_000002.9 | 139378309 | C | T | 0.00071933 | NXPH2 | neurexophilin 2 | up |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 4077723 | 6463266 | 24343132 | NC_000007.11 | 4926524 | G | T | 9.99002E-06 | OR10AH1P | olfactory receptor, family 10, subfamily AH, member 1 pseudogene | down |
| 4077723 | 6463266 | 24343132 | NC_000007.11 | 4926524 | G | T | 9.99002E-06 | LOC441192 | similar to Zinc finger protein 16 (Zinc finger protein KOX9) | down |
| 3711990 | 8051542 | 24530965 | NC_000016.8 | 51091668 | T | C | 1.11036E-05 | TNRC9 | trinucleotide repeat containing 9 | intron |
| 3488617 | 3852789 | 24110311 | NC_000016.8 | 70786007 | A | C | 1.52607E-05 | PMFBP1 | polyamine modulated factor 1 binding protein 1 | 25kb up |
| 3337858 | 12658840 | 23928828 | NC_000005.8 | 160251566 | A | G | 1.19405E-05 | | | |
| 4093095 | 6469633 | 23343761 | NC_000008.9 | 117205405 | T | C | 1.28115E-05 | TRPS1 | trichorhinophalangeal syndrome I | 450kb up |
| 4538418 | 2298075 | 24488770 | NC_000010.8 | 102237398 | C | A | 0.12570628 | WNT8B | wingless-type MMTV integration site family, member 8B | down |
| 4538418 | 2298075 | 24488770 | NC_000010.8 | 102237398 | C | A | 0.12570628 | SEC31L2 | SEC31-like 2 (S. cerevisiae) | exon |
| 4213825 | 7443644 | 23179775 | NC_000005.8 | 29282566 | C | T | 1.49811E-05 | | | |
| 4141351 | 7307700 | 23482623 | NC_000012.9 | 124113077 | G | A | 8.18526E-05 | AACS | acetoacetyl-CoA synthetase | intron |
| 2770052 | 30099 | 23984516 | NC_000005.8 | 52454339 | G | A | 5.25187E-05 | | | |
| 3610210 | 16998733 | 23731751 | NC_000004.9 | 149695013 | T | C | 1.67319E-05 | NR3C2 | nuclear receptor subfamily 3, group C, member 2 | intron |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3451239 | 6843340 | 24655372 | NC_000004.9 | 48460865 | C | T | 1.72313E-05 | KIAA0826 | KIAA0826 protein | intron |
| 1582533 | 17157070 | 24001013 | NC_000007.11 | 108946886 | A | G | 1.74197E-05 | | | |
| 2211664 | 1418884 | 24570308 | NC_000010.8 | 13958420 | A | G | 0.001170929 | FRMD4A | FERM domain containing 4A | intron |
| 1469031 | 17184313 | 24607058 | NC_000014.7 | 92172004 | C | T | 4.73418E-05 | RIN3 | Ras and Rab interactor 3 | intron |
| 333581 | 9393597 | 23949563 | NC_000006.9 | 25081087 | A | G | 2.99979E-05 | | | |
| 3046384 | 2354314 | 24659411 | NC_000004.9 | 48562255 | T | C | 3.21196E-05 | | | |
| 217009 | 7144254 | 23637031 | NC_000014.7 | 87865970 | A | C | 3.68972E-05 | KCNK10 | potassium channel, subfamily K, member 10 | up |
| 3293027 | 17817901 | 24702043 | NC_000017.9 | 50393744 | A | G | 3.81703E-05 | TOM1L1 | target of myb1-like 1 (chicken) | exon |
| 3293027 | 17817901 | 24702043 | NC_000017.9 | 50393744 | A | G | 3.81703E-05 | COX11 | COX11 homolog, cytochrome c oxidase assembly prote | exon |
| 2494880 | 419793 | 24564591 | NC_000017.9 | 71824681 | C | T | 3.82784E-05 | PRPSAP1 | phosphoribosyl pyrophosphate synthetase-associated | intron |
| 2494880 | 419793 | 24564591 | NC_000017.9 | 71824681 | C | T | 3.82784E-05 | QRICH2 | glutamine rich 2 | up |
| 2040055 | 13121 | 23955626 | NC_000012.9 | 51245972 | G | C | 0.000136807 | K6IRS4 | keratin 6 irs4 | exon |
| 4444217 | 6601491 | 24408136 | NC_000008.9 | 10453427 | A | G | 3.97262E-05 | RP1L1 | retinitis pigmentosa 1-like 1 | 45kb down |
| 2020372 | 17316319 | 24434774 | NC_000012.9 | 24985970 | G | A | 0.005297866 | BCAT1 | branched chain aminotransferase 1, cytosolic | intron |
| 4608752 | 2746479 | 23176778 | NC_000001.8 | 17214998 | G | A | 0.930360524 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3556839 | 12148733 | 24048722 | NC_000015.8 | 70622069 | G | A | 4.30653E-05 | ARIH1 | ariadne homolog, ubiquitin-conjugating enzyme E2 b | intron |
| 4436205 | 6472904 | 24279900 | NC_000008.9 | 76398806 | C | A | 4.30871E-05 | | | |
| 3479310 | 671236 | 23271939 | NC_000004.9 | 160275275 | G | C | 4.36681E-05 | FLJ25371 | hypothetical protein FLJ25371 | intron |
| 2384760 | 13079811 | 23885413 | NC_000003.9 | 82697593 | C | A | 4.51781E-05 | | | |
| 1241235 | 1533802 | 23232437 | NC_000002.9 | 26704766 | A | C | 4.79973E-05 | LOC339778 | hypothetical protein LOC339778 | intron |
| 3479301 | 17223438 | 24322799 | NC_000004.9 | 160287705 | C | T | 4.83903E-05 | FLJ25371 | hypothetical protein FLJ25371 | intron |
| 3198633 | 7185203 | 23521506 | NC_000016.8 | 80196691 | C | T | 5.66624E-05 | CMIP | c-Maf-inducing protein | intron |
| 2414873 | 2997545 | 24567207 | NC_000009.9 | 7409745 | C | G | 5.7616E-05 | | | |
| 2932010 | 7182242 | 23811974 | NC_000015.8 | 58465642 | T | C | 6.44778E-05 | ANXA2 | annexin A2 | up |
| 4537674 | 17816264 | 24403126 | NC_000006.9 | 102073246 | T | C | 0.000470286 | GRIK2 | glutamate receptor, ionotropic, kainate 2 | intron |
| 506949 | 1511682 | 23528382 | NC_000007.11 | 79627074 | A | G | 7.07069E-05 | | | |
| 3396690 | 12511735 | 24308203 | NC_000004.9 | 82230811 | T | C | 0.000115825 | ABLIM2 | actin binding LIM protein family, member 2 | intron |
| 3715867 | 9937572 | 23987502 | NC_000016.8 | 54447899 | G | C | 7.35617E-05 | FLJ31547 | hypothetical protein FLJ31547 | intron |
| 2414930 | 2986261 | 24567528 | NC_000009.9 | 7457934 | G | A | 7.47921E-05 | LOC158345 | similar to ribosomal protein L4; 60S ribosomal pro | down |
| 8190 | 2823288 | 24720177 | NC_000021.7 | 15742759 | G | A | 0.024794583 | | | |
| 4498529 | 932096 | 24585465 | NC_000011.8 | 130847403 | C | T | 7.71211E-05 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 2259433 | 7922576 | 24067081 | NC_000010.8 | 63970643 | A | T | 7.71872E-05 | ZNF365 | zinc finger protein 365 | intron |
| 1459255 | 10143004 | 24129480 | NC_000014.7 | 62896438 | C | T | 7.76274E-05 | | | |
| 173135 | 12433482 | 24114031 | NC_000014.7 | 39106280 | C | G | 7.94798E-05 | | | |
| 2446045 | 10869043 | 23578438 | NC_000009.9 | 68401373 | C | A | 8.00174E-05 | | | |
| 1807755 | 4273130 | 24027015 | NC_000018.8 | 37739538 | G | A | 8.03055E-05 | | | |
| 3451137 | 16868020 | 23370935 | NC_000004.9 | 30882433 | G | A | 8.37895E-05 | | | |
| 2510905 | 1000515 | 24634604 | NC_000004.9 | 157761947 | C | A | 8.38395E-05 | | | |
| 1645593 | 909116 | 24379768 | NC_000011.8 | 1898522 | T | C | 8.93269E-05 | TNNT3 | troponin T3, skeletal, fast | up |
| 3692265 | 637396 | 24455158 | NC_000005.8 | 32493514 | T | C | 9.14205E-05 | | | |
| 3601436 | 2560311 | 24341904 | NC_000005.8 | 121493724 | T | C | 9.18769E-05 | FLJ32921 | hypothetical LOC133923 | intron |
| 3711986 | 9923960 | 24530942 | NC_000016.8 | 51085545 | G | A | 9.29172E-05 | TNRC9 | trinucleotide repeat containing 9 | intron |
| 2209860 | 4750232 | 24098133 | NC_000010.8 | 126281230 | A | G | 9.54033E-05 | CAMK1D | calcium/calmodulin-dependent protein kinase ID | intron |
| 2396695 | 9866721 | 23248754 | NC_000003.9 | 107490054 | T | C | 9.91275E-05 | | | |
| 4121333 | 714694 | 23980083 | NC_000011.8 | 78394949 | A | G | 0.000101714 | | | |
| 4366841 | 2200204 | 23403939 | NC_000011.8 | 83380707 | C | T | 0.000103203 | DLG2 | discs, large homolog 2, chapsyn-110 (Drosophila) | intron |
| 2309019 | 11198171 | 24572407 | NC_000010.8 | 119646662 | G | A | 0.000107332 | | | |
| 4319226 | 4132417 | 23939526 | NC_000003.9 | 118908948 | A | T | 0.000257926 | | | |
| 3451005 | 16861305 | 23728499 | NC_000004.9 | 48307709 | A | G | 0.000113458 | | | |
| 1332268 | 1427604 | 24285363 | NC_000002.9 | 137361437 | G | A | 0.002483802 | | | |
| 3994115 | 1257022 | 24642746 | NC_000002.9 | 97036810 | C | T | 0.000114719 | | | |
| 1071847 | 1889229 | 23151966 | NC_000001.8 | 97974674 | A | T | 0.000116107 | DPYD | dihydropyrimidine dehydrogenase | intron |
| 1439274 | 8021611 | 24542085 | NC_000014.7 | 26683461 | A | G | 0.00011624 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 2225587 | 7905083 | 24200442 | NC_000010.8 | 26510152 | T | A | 0.000116638 | MYO3A | myosin IIIA | intron |
| 1765974 | 2304859 | 24021883 | NC_000018.8 | 2740477 | A | G | 0.000122411 | KIAA0650 | KIAA0650 protein | exon |
| 801087 | 1872556 | 23927075 | NC_000003.9 | 85147919 | A | G | 0.000126165 | | | |
| 4141564 | 2124714 | 24491813 | NC_000012.9 | 130824248 | G | A | 0.000128963 | | | |
| 2271457 | 7076580 | 24089931 | NC_000010.8 | 78913954 | T | C | 0.000438817 | KCNMA1 | potassium large conductance calcium-activated chan | intron |
| 2932281 | 2054622 | 23427448 | NC_000005.8 | 113347984 | C | T | 0.000722701 | | | |
| 3125832 | 3736430 | 23955564 | NC_000005.8 | 56216237 | A | G | 0.000141295 | MAP3K1 | mitogen-activated protein kinase kinase kinase 1 | intron |
| 1792008 | 9952863 | 24197059 | NC_000018.8 | 26808125 | G | A | 0.092758438 | | | |
| 2111104 | 2874716 | 23965722 | NC_000013.9 | 33934537 | G | A | 0.000142792 | | | |
| 3447499 | 17470619 | 24658855 | NC_000004.9 | 44918382 | T | C | 0.000144981 | | | |
| 119233 | 763073 | 24090986 | NC_000022.8 | 27540096 | G | A | 0.000147898 | LOC388890 | LOC388890 | intron |
| 3548614 | 10518741 | 23361950 | NC_000015.8 | 39986759 | T | C | 0.044453006 | EHD4 | EH-domain containing 4 | intron |
| 1671130 | 10400315 | 24148884 | NC_000011.8 | 25914884 | G | A | 0.000153096 | | | |
| 1732604 | 7931430 | 23523373 | NC_000011.8 | 95015194 | T | C | 0.00015587 | | | |
| 2209870 | 6602595 | 24098162 | NC_000010.8 | 12631922 | G | A | 0.000162264 | CAMK1D | calcium/calmodulin-dependent protein kinase ID | intron |
| 309350 | 4512241 | 24021298 | NC_000006.9 | 124229621 | T | G | 0.000168878 | TCBA1 | T-cell lymphoma breakpoint associated target 1 | intron |
| 1408259 | 1355339 | 23904287 | NC_000002.9 | 205668809 | T | C | 0.29494862 | ALS2CR19 | amyotrophic lateral sclerosis 2 (juvenile) chromos | intron |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 2165569 | 9518578 | 23733684 | NC_000013.9 | 101278869 | T | C | 0.000171338 | FGF14 | fibroblast growth factor 14 | intron |
| 2223520 | 11597573 | 23458103 | NC_000010.8 | 24594202 | C | T | 0.000171449 | KIAA1217 | | intron |
| 4237684 | 2080976 | 24008186 | NC_000005.8 | 166923617 | T | C | 0.000172464 | | | |
| 4579386 | 5926344 | 24726009 | NC_000023.8 | 27812548 | C | T | 0.000174311 | | | |
| 984465 | 6696544 | 23850740 | NC_000001.8 | 75555855 | C | A | 0.000177323 | CAMTA1 | calmodulin binding transcription activator 1 | intron |
| 2383801 | 1472302 | 24353339 | NC_000003.9 | 85080588 | C | T | 0.00018387 | | | |
| 1926776 | 17394924 | 24534619 | NC_000008.9 | 66723488 | T | C | 0.000187739 | MTFR1 | mitochondrial fission regulator 1 | intron |
| 4410891 | 4444992 | 23179944 | NC_000005.8 | 29316121 | G | T | 0.000188518 | | | |
| 832067 | 175516457 | 24664787 | NC_000005.8 | 131618286 | T | C | 0.000368434 | PDLIM4 | PDZ and LIM domain 4 | up |
| 1463608 | 8011464 | 23618822 | NC_000014.7 | 82438217 | C | T | 0.001470034 | | | |
| 1563613 | 921915 | 23746941 | NC_000007.11 | 50005842 | T | C | 0.000192754 | | | |
| 1620444 | 17771656 | 24405260 | NC_000016.8 | 4868258 | G | A | 0.00019566 | UBN1 | ubinuclein 1 | intron |
| 1620444 | 17771656 | 24405260 | NC_000016.8 | 4868258 | G | A | 0.00019566 | PPL | periplakin | down |
| 224089 | 17732513 | 24599147 | NC_000014.7 | 91456132 | C | T | 0.000199647 | FBLN5 | fibulin 5 | intron |
| 3326942 | 6580582 | 24195649 | NC_000005.8 | 148153575 | T | C | 0.000199934 | | | |
| 1926956 | 7818219 | 24535439 | NC_000008.9 | 67081677 | G | A | 0.000207237 | | | |
| 4095549 | 7463445 | 24347073 | NC_000008.9 | 136103657 | G | A | 0.000209208 | | | |
| 2618329 | 985053 | 24512618 | NC_000018.8 | 66084702 | C | T | 0.000212168 | | | |
| 2300537 | 1329499 | 23496882 | NC_000010.8 | 110206419 | C | T | 0.000213418 | | | |
| 1263368 | 6713681 | 24618399 | NC_000002.9 | 54558471 | C | G | 0.000217067 | LOC442016 | | up |
| 4130302 | 956993 | 23627628 | NC_000011.8 | 130859681 | T | G | 0.000224646 | | | |
| 2228425 | 796829 | 24202945 | NC_000010.8 | 29153703 | G | C | 0.00358584 | | | |
| 4450860 | 7016682 | 23768269 | NC_000008.9 | 110037787 | T | G | 0.000231981 | | | |
| 3705419 | 7226024 | 23793458 | NC_000017.9 | 5666418 | T | C | 0.000238606 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 1044847 | 3790436 | 24243521 | NC_000001.8 | 65587872 | G | C | 0.000815582 | DNAJC6 | DnaJ (Hsp40) homolog, subfamily C, member 6 | intron |
| 3116422 | 17266006 | 24428214 | NC_000005.8 | 44574638 | C | T | 0.000240339 | | | |
| 2414892 | 2986258 | 24102575 | NC_000009.9 | 7442632 | C | T | 0.000240516 | | | |
| 989937 | 6658612 | 24244162 | NC_000001.8 | 15285618 | G | C | 0.000242229 | FLJ10199 | hypothetical protein FLJ10199 | intron |
| 2160010 | 2993568 | 24224498 | NC_000013.9 | 94854541 | G | A | 0.000253047 | | | |
| 3615438 | 10015937 | 23686365 | NC_000004.9 | 153291215 | T | C | 0.014236138 | | | |
| 1678510 | 2227973 | 24104518 | NC_000011.8 | 36553889 | A | G | 0.000257749 | RAG1 | recombination activating gene 1 | exon |
| 1942247 | 10112708 | 24093024 | NC_000008.9 | 80701779 | G | T | 0.000261129 | STMN2 | stathmin-like 2 | intron |
| 3456439 | 10030740 | 24356386 | NC_000004.9 | 36208318 | A | G | 0.000261436 | | | |
| 31381165 | 7872321 | 24524095 | NC_000009.9 | 124131826 | C | T | 0.003292547 | NEK6 | NIMA (never in mitosis gene a)-related kinase 6 | intron |
| 3293073 | 6504950 | 23788943 | NC_000017.9 | 50411470 | G | A | 0.000270244 | STXBP4 | syntaxin binding protein 4 | up |
| 1562775 | 2043394 | 23745577 | NC_000007.11 | 48277028 | G | A | 0.009931002 | ABCA13 | ATP binding cassette gene, sub-family A (ABC1), me | intron |
| 1938678 | 10092157 | 23568081 | NC_000008.9 | 77401292 | T | G | 0.000276109 | | | |
| 1776660 | 1954856 | 24013360 | NC_000018.8 | 106090090 | G | A | 0.017222687 | LOC440480 | | down |
| 2488222 | 8075449 | 24119233 | NC_000017.9 | 64144160 | C | T | 0.001177372 | | | |
| 2246245 | 10822095 | 24564484 | NC_000010.8 | 52444923 | C | T | 0.000282007 | | | |
| 309389 | 2057081 | 23465932 | NC_000006.9 | 124257139 | G | C | 0.000288185 | TCBA1 | T-cell lymphoma breakpoint associated target 1 | intron |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 14586 | 17755917 | 24692249 | NC_000021.7 | 17878576 | T | C | 0.000293026 | BTG3 | BTG family, member 3 | down |
| 4605974 | 314274 | 23659133 | NC_000006.9 | 105519625 | A | C | 0.000296788 | LOC389421 | LOC389421 | intron |
| 8332159 | 3091338 | 24664633 | NC_000005.8 | 131430637 | C | T | 0.000299146 | IL3 | interleukin 3 (colony-stimulating factor, multiple | down |
| 8332159 | 3091338 | 24664633 | NC_000005.8 | 131430637 | C | T | 0.000299146 | CSF2 | colony stimulating factor 2 (granulocyte-macrophag | up |
| 1785118 | 4800637 | 24710897 | NC_000005.8 | 213472217 | C | T | 0.001484172 | LOC441817 | | intron |
| 677379 | 12748993 | 24238877 | NC_000001.8 | 8063773 | A | G | 0.000300336 | | | |
| 4444356 | 6725361 | 24628836 | NC_000002.9 | 19200437 | G | A | 0.002136012 | LOC388927 | LOC388927 | down |
| 965534 | 1006436 | 24577204 | NC_000016.8 | 70789817 | A | G | 0.000309771 | | | |
| 3415236 | 17355932 | 24330925 | NC_000004.9 | 107713111 | A | G | 0.055431553 | | | |
| 4459567 | 73333503 | 24453356 | NC_000013.9 | 94884481 | C | T | 0.000310854 | CLDN10 | claudin 10 | intron |
| 1937485 | 6989976 | 23559603 | NC_000008.9 | 76392642 | A | G | 0.000311249 | | | |
| 211496 | 190119 | 24604849 | NC_000014.7 | 79768599 | T | C | 0.249098722 | | | |
| 3132019 | 10120598 | 23530014 | NC_000009.9 | 114805665 | T | A | 0.009174673 | | | |
| 4310485 | 4767751 | 24354343 | NC_000012.9 | 117876630 | G | T | 0.000329805 | KIAA1853 | KIAA1853 protein | up |
| 1180519 | 1339207 | 24282858 | NC_000001.8 | 213624209 | T | C | 0.000330482 | ESRRG | estrogen-related receptor gamma | intron |
| 2757715 | 159352 | 24438530 | NC_000005.8 | 94246916 | C | G | 0.000331105 | MCTP1 | multiple C2 domains, transmembrane 1 | intron |
| 2290837 | 10450393 | 24556565 | NC_000010.8 | 97204408 | T | C | 0.000333239 | SORBS1 | sorbin and SH3 domain containing 1 | intron |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 1866638 | 10110673 | 24407713 | NC_000008.9 | 13070079 | G | A | 0.000335314 | DLC1 | deleted in liver cancer 1 | intron |
| 1420908 | 16660316 | 23728525 | NC_000002.9 | 220490605 | C | T | 0.000338169 | | | |
| 4441196 | 6551302 | 24644406 | NC_000003.9 | 88380393 | A | G | 0.000338519 | | | |
| 3637653 | 6712838 | 24274391 | NC_000002.9 | 77390874 | C | T | 0.000338895 | | | |
| 2329317 | 17047056 | 23874187 | NC_000003.9 | 7317847 | G | A | 0.000349926 | GRM7 | glutamate receptor, metabotropic 7 | intron |
| 3384681 | 17063892 | 23373247 | NC_000005.8 | 174100885 | T | C | 0.045944708 | | | |
| 4625548 | 7407574 | 24198712 | NC_000018.8 | 46278357 | G | T | 0.000365739 | | | |
| 119275 | 5762870 | 24091131 | NC_000022.8 | 27585713 | C | T | 0.000366135 | | | |
| 1015553 | 11208958 | 23836719 | NC_000001.8 | 409451166 | C | T | 0.003044271 | KCNQ4 | potassium voltage-gated channel, KQT-like subfamil | intron |
| 2246625 | 679438 | 24102278 | NC_000010.8 | 52867317 | T | C | 0.000373272 | PRKG1 | protein kinase, cGMP-dependent, type I | intron |
| 1763514 | 3932728 | 23452441 | NC_000018.8 | 381147 | T | C | 0.000375941 | COLEC12 | collectin sub-family member 12 | intron |
| 3400817 | 6837118 | 23929205 | NC_000004.9 | 16405845 | C | T | 0.000380543 | LDB2 | LIM domain binding 2 | intron |
| 267509 | 6909231 | 23344270 | NC_000006.9 | 16579218 | T | A | 0.00038304 | SCA1 | spinocerebellar ataxia 1 (olivopontocerebellar ata | intron |
| 876010 | 10809833 | 23964059 | NC_000009.9 | 1273014 | C | T | 0.000388289 | | | |
| 2770095 | 1445998 | 24387628 | NC_000005.8 | 56303962 | A | G | 0.000391458 | | | |
| 3329550 | 2915827 | 24198744 | NC_000005.8 | 151099898 | A | T | 0.000397136 | ATOX1 | ATX1 antioxidant protein 1 homolog (yeast) | down |
| 3153177 | 3732582 | 23942357 | NC_000003.9 | 185016771 | G | C | 0.000406858 | FLJ10201 | hypothetical protein FLJ10201 | down |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3153177 | 3732582 | 23942357 | NC_000003.9 | 185016771 | G | C | | FLJ12748 | hypothetical protein FLJ12748 | exon |
| 1008558 | 10753302 | 23180780 | NC_000001.8 | 34360427 | C | A | 0.000406858 | MGC15882 | hypothetical protein MGC15882 | down |
| 2430749 | 7871803 | 24694501 | NC_000009.9 | 25210929 | T | C | 0.000408863 | | | |
| 853211 | 4837864 | 23676926 | NC_000009.9 | 116623987 | T | C | 0.000414357 | ASTN2 | astrotactin 2 | intron |
| 4240775 | 1008328 | 23762489 | NC_000019.8 | 41287276 | A | C | 0.000417526 | POLR2I | polymerase (RNA) II (DNA directed) polypeptide I, | down |
| 4240775 | 1008328 | 23762489 | NC_000019.8 | 41287276 | A | C | 0.000424572 | LOC400688 | similar to comment for location 3447-3655: BLASTX | up |
| 4240775 | 1008328 | 23762489 | NC_000019.8 | 41287276 | A | C | 0.000424572 | WDR62 | WD repeat domain 62 | exon |
| 4569912 | 7497644 | 23451745 | NC_000015.8 | 36464819 | A | G | 0.000426045 | | | |
| 2411434 | 13294435 | 24684738 | NC_000009.9 | 1958865 | A | T | 0.001787587 | | | |
| 1512505 | 2220790 | 24472413 | NC_000006.9 | 92854884 | A | G | 0.000433087 | | | |
| 3451645 | 11947369 | 24175450 | NC_000004.9 | 52541699 | T | C | 0.000433104 | KIAA0276 | KIAA0276 protein | up |
| 3125930 | 16886518 | 23955788 | NC_000005.8 | 56269494 | C | A | 0.000433859 | MGC33648 | hypothetical protein MGC33648 | intron |
| 3125930 | 16886518 | 23955788 | NC_000005.8 | 56269494 | C | A | 0.000433859 | DKFZP78I11119 | hypothetical protein FLJ35954 | intron |
| 189787 | 17824919 | 24213669 | NC_000014.7 | 62927561 | G | A | 0.000434991 | PPP2R5E | protein phosphatase 2, regulatory subunit B (B56). | intron |
| 3162327 | 17383211 | 24444883 | NC_000018.8 | 1518514 | A | G | 0.000447949 | | | |
| 2346382 | 9842800 | 23273689 | NC_000003.9 | 26937324 | A | G | 0.000452629 | | | |
| 4171235 | 7209174 | 24532524 | NC_000017.9 | 75912344 | A | T | 0.000452782 | KIAA1618 | KIAA1618 | down |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 2295056 | 4244347 | 24493405 | NC_000010.8 | 103442635 | A | C | 0.000457877 | SHFM3 | split hand/foot malformation (ectrodactyly) type 3 | intron |
| 532507 | 855737 | 24400682 | NC_000007.11 | 148801656 | T | C | 0.000460881 | KIAA1862 | | intron |
| 1943565 | 10504736 | 24562209 | NC_000008.9 | 82269581 | G | A | 0.000461953 | LOC392238 | LOC392238 | intron |
| 3396667 | 6841948 | 23250549 | NC_000004.9 | 81058731 | T | C | 0.000466165 | ABLIM2 | actin binding LIM protein family, member 2 | intron |
| 152828 | 4982579 | 24709056 | NC_000014.7 | 21764924 | C | T | 0.000470185 | | | |
| 1639033 | 10852432 | 24679236 | NC_000016.8 | 64960016 | T | C | 0.008108658 | CDH5 | cadherin 5, type 2, VE-cadherin (vascular epitheli | intron |
| 2856553 | 330336 | 23934183 | NC_000005.8 | 124936798 | C | G | 0.011702637 | | | |
| 3444104 | 2632710 | 23722617 | NC_000004.9 | 42215130 | T | C | 0.000481175 | | | |
| 2290061 | 1010570 | 23586587 | NC_000010.8 | 96436622 | G | A | 0.000490734 | CYP2C18 | cytochrome P450, family 2, subfamily C, polypeptid | intron |
| 966431 | 7190785 | 24508965 | NC_000016.8 | 9780966 | G | A | 0.000492641 | GRIN2A | glutamate receptor, ionotropic, N-methyl D-asparta | intron |
| 1662099 | 2654010 | 24100039 | NC_000011.8 | 19334920 | T | C | 0.000502931 | | | |
| 438606 | 6134320 | 23801369 | NC_000020.9 | 11604757 | C | G | 0.000506436 | | | |
| 3558319 | 7178409 | 24049349 | NC_000015.8 | 70874419 | T | C | 0.000864056 | | | |
| 2488224 | 7359564 | 23631377 | NC_000017.9 | 64145462 | G | A | 0.001399067 | | | |
| 4644209 | 6459856 | 23935604 | NC_000007.11 | 157596862 | T | C | 0.000517387 | PTPRN2 | protein tyrosine phosphatase, receptor type, N pol | intron |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3686023 | 9292668 | 23904948 | NC_000005.8 | 19603537 | T | C | 0.000086008 | CDH18 | cadherin 18, type 2 | intron |
| 2142614 | 9564996 | 24063534 | NC_000013.9 | 72937265 | G | A | 0.000519763 | | | |
| 2638022 | 1111481 | 24530959 | NC_000016.8 | 51089856 | C | T | 0.000052222 | TNRC9 | trinucleotide repeat containing 9 | intron |
| 4441915 | 6556352 | 23922149 | NC_000005.8 | 155404292 | C | T | 0.000531957 | | | |
| 886860 | 4763707 | 24702081 | NC_000012.9 | 11605921 | G | A | 0.000533058 | | | |
| 3667983 | 2292462 | 24365878 | NC_000015.8 | 83001758 | G | T | 0.000536267 | WDR73 | WD repeat domain 73 | up |
| 3667983 | 2292462 | 24365878 | NC_000015.8 | 83001758 | G | T | 0.000536267 | SCAND2 | SCAN domain containing 2 | intron |
| 3667983 | 2292462 | 24365878 | NC_000015.8 | 83001758 | G | T | 0.000536267 | NMB | neuromedin B | intron |
| 3594921 | 4906753 | 23748382 | NC_000015.8 | 23519154 | G | A | 0.688040199 | ATP10A | ATPase, Class V, type 10A | intron |
| 1408258 | 4675478 | 23268928 | NC_000002.9 | 205668475 | C | T | 0.145833517 | ALS2CR19 | amyotrophic lateral sclerosis 2 (juvenile) chromos | intron |
| 2106017 | 6491176 | 24465377 | NC_000013.9 | 26480230 | C | T | 0.00291247 | | | |
| 4047923 | 152088 | 23983485 | NC_000005.8 | 52344772 | C | T | 0.000547038 | ITGA2 | integrin, alpha 2 (CD49B, alpha 2 subunit of VLA-2 receptor) | intron |
| 1687176 | 1973716 | 24101842 | NC_000011.8 | 43903155 | G | C | 0.000547148 | LOC387763 | hypothetical gene supported by BC052560 | up |
| 1687176 | 1973716 | 24101842 | NC_000011.8 | 43903155 | G | C | 0.000547148 | DEPC-1 | prostate cancer antigen-1 | down |
| 2093317 | 12425296 | 24169760 | NC_000012.9 | 116450294 | A | C | 0.000547453 | KSR2 | kinase suppressor of Ras-2 | intron |
| 4068031 | 694975 | 24426548 | NC_000006.9 | 153281383 | A | G | 0.000761866 | | | |

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 1646434 | 683142 | 24061897 | NC_000011.8 | 3671612 | T | G | 0.000555232 | NUP98 | nucleoporin 98kDa | intron |
| 391866 | 1291149 | 24206491 | NC_000020.9 | 34966876 | C | T | 0.000552768 | SAMHD1 | SAM domain and HD domain 1 | intron |
| 2563410 | 3846370 | 23295212 | NC_000004.9 | 13744469 | G | A | 0.000555229 | | | |
| 3845440 | 11143514 | 24474467 | NC_000009.9 | 73019133 | G | A | 0.000555518 | LOC442424 | similar to tMDC 1 | intron |
| 3845440 | 11143514 | 24474467 | NC_000009.9 | 73019133 | G | A | 0.000555518 | ANXA1 | annexin A1 | down |
| 946689 | 2165698 | 24455109 | NC_000013.9 | 87356040 | T | C | 0.00055612 | | | |
| 4411283 | 4450862 | 24629557 | NC_000003.9 | 31236256 | A | G | 0.000561198 | | | |
| 4263852 | 728448 | 23655180 | NC_000001.8 | 34727194 | G | A | 0.000571044 | | | |
| 4565513 | 1144953 | 23660481 | NC_000012.9 | 67576949 | G | T | 0.000575206 | CPM | carboxypeptidase M | intron |
| 618936 | 17350806 | 24529263 | NC_000011.8 | 34360958 | T | A | 0.015170064 | | | |
| 3193216 | 2738545 | 24683409 | NC_000016.8 | 77186821 | G | A | 0.000577481 | WWOX | WW domain containing oxidoreductase | intron |
| 1777298 | 7239326 | 24464456 | NC_000018.8 | 11655293 | C | G | 0.000577736 | | | |
| 4231045 | 500079 | 23812937 | NC_000019.8 | 54070806 | A | G | 0.000581683 | TULP2 | tubby like protein 2 | down |
| 4231045 | 500079 | 23812937 | NC_000019.8 | 54070806 | A | G | 0.000581683 | PLEKHA4 | pleckstrin homology domain containing, family A (p | up |
| 4231045 | 500079 | 23812937 | NC_000019.8 | 54070806 | A | G | 0.000581683 | PPP1R15A | protein phosphatase 1, regulatory (inhibitor) subu | exon |
| 3589081 | 11241256 | 23997557 | NC_000005.8 | 113363129 | C | T | 0.000587987 | | | |
| 2082684 | 17034027 | 23455354 | NC_000012.9 | 102399062 | T | C | 0.000164348 | FLJ25323 | FLJ25323 protein | up |
| 4613353 | 881997 | 24241925 | NC_000004.9 | 78455985 | C | T | 0.000599656 | | | |
| 1870512 | 7012024 | 24174665 | NC_000008.9 | 14882125 | T | C | 0.046328297 | | | |
| 2093797 | 4766886 | 23719822 | NC_000012.9 | 116807841 | T | C | 0.000603925 | | | |

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 1869307 | 10503496 | 24423949 | NC_000008.9 | 14293571 | C | T | 0.000606004 | SGCZ | sarcoglycan zeta | intron |
| 885177 | 17835992 | 24204152 | NC_000012.9 | 35392501 | G | A | 0.000617635 | HRMT1L4 | HMT1 hnRNP methyltransferase-like 4 (S. cerevisiae) | intron |
| 678769 | 1933398 | 23181463 | NC_000001.8 | 77176693 | G | C | 0.001620126 | SIAT7E | sialyltransferase 7 ((alpha-N-acetylneuraminyl-2,3 | intron |
| 3161532 | 6567201 | 24513626 | NC_000018.8 | 56988681 | T | A | 0.000623025 | | | |
| 1160916 | 946262 | 24256140 | NC_000001.8 | 199889886 | T | C | 0.102265582 | CHI3L1 | chitinase 3-like 1 (cartilage glycoprotein-39) | up |
| 3601420 | 2560314 | 24341869 | NC_000005.8 | 121487762 | C | T | 0.001448248 | FLJ32921 | hypothetical LOC133923 | up |
| 831864 | 4706020 | 24664526 | NC_000005.8 | 130701975 | G | A | 0.000645476 | | | |
| 1275782 | 10496221 | 23882303 | NC_000002.9 | 79475174 | T | C | 0.000649174 | | | |
| 2401308 | 7611423 | 23310174 | NC_000003.9 | 113990491 | C | T | 0.000663474 | | | |
| 1827179 | 302050 | 23604804 | NC_000018.8 | 52286539 | G | T | 0.003056778 | | | |
| 1836909 | 17827708 | 24503658 | NC_000018.8 | 63440675 | A | G | 0.000668666 | | | |
| 3869041 | 12852381 | 23829904 | NC_000023.8 | 120081768 | A | G | 0.096568117 | | | |
| 486999 | 10231161 | 24432882 | NC_000007.11 | 26483805 | G | C | 0.000685196 | SCAP2 | src family associated phosphoprotein 2 | intron |
| 1666000 | 17305979 | 24625499 | NC_000011.8 | 21969179 | G | A | 0.004877609 | | | |
| 249186 | 2064491 | 24595200 | NC_000014.7 | 101003117 | C | T | 0.325952337 | | | |
| 3385954 | 13164340 | 24383100 | NC_000005.8 | 180047128 | G | C | 0.000687812 | OR2A11P | olfactory receptor, family 2, subfamily A1, member 1 pseudogene | down |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 825740 | 12450620 | 23619204 | NC_000017.9 | 43485253 | G | T | 0.153279685 | NFE2L1 | nuclear factor (erythroid-derived 2)-like 1 | intron |
| 825740 | 12450620 | 23619204 | NC_000017.9 | 43485253 | G | T | 0.153279685 | LOC400602 | LOC400602 | up |
| 996355 | 3738099 | 23844815 | NC_000001.8 | 216400411 | T | C | 0.000697798 | ALPL | alkaline phosphatase, liver/bone/kidney | exon |
| 3593039 | 10004565 | 23411693 | NC_000035.5 | 1399635555 | T | C | 0.000698791 | | | |
| 1197836 | 828470 | 23233251 | NC_000001.8 | 226833740 | T | C | 0.000698987 | | | |
| 1204167 | 12133803 | 24265434 | NC_000001.8 | 231189917 | T | C | 0.004436676 | | | |
| 657579 | 7548280 | 23179173 | NC_000001.8 | 164471098 | C | G | 0.000715737 | MP2L1 | myelin protein zero-like 1 | intron |
| 1998542 | 3847174 | 24480616 | NC_000008.9 | 134062628 | C | T | 0.000719576 | TG | thyroglobulin | intron |
| 1957380 | 2575721 | 23504535 | NC_000008.9 | 97617224 | A | C | 0.000864411 | SDC2 | syndecan 2 (heparan sulfate proteoglycan 1, cell s | intron |
| 832147 | 4705916 | 24664657 | NC_000005.8 | 131435392 | C | A | 0.000725255 | IL3 | interleukin 3 (colony-stimulating factor, multiple | down |
| 832147 | 4705916 | 24664657 | NC_000005.8 | 131435392 | C | A | 0.000725255 | CSF2 | colony stimulating factor 2 (granulocyte-macrophag | up |
| 332043 | 9296670 | 24373204 | NC_000006.9 | 52057204 | C | T | 0.00072555 | PKHD1 | polycystic kidney and hepatic disease 1 (autosomal | intron |
| 3867915 | 17261572 | 24729638 | NC_000023.8 | 119542511 | A | T | 0.000736375 | LOC392531 | | up |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3867915 | 17261572 | 24729638 | NC_000023.8 | 119542511 | A | T | 0.000736375 | C1GALT2 | core 1 UDP-galactose:N-acetylgalactosamine-alpha-R | exon |
| 1451284 | 17721908 | 24140439 | NC_000014.7 | 49494161 | G | T | 0.000743578 | | | |
| 224041 | 2498835 | 24599081 | NC_000014.7 | 91440576 | T | G | 0.000744089 | FBLN5 | fibulin 5 | intron |
| 1255579 | 698778 | 23717259 | NC_000002.9 | 44652335 | G | A | 0.011783626 | FLJ23451 | hypothetical protein FLJ23451 | intron |
| 119389 | 2213645 | 24553392 | NC_000022.8 | 27685713 | A | G | 0.000756818 | ZNRF3 | novel C3HC4 type Zinc finger (ring finger) | intron |
| 1970418 | 1497628 | 23570328 | NC_000008.9 | 10973626 | T | C | 0.00076029 | | | |
| 3368550 | 2898881 | 24726765 | NC_000023.8 | 77977631 | C | T | 0.000766552 | | | |
| 3125553 | 154751 | 23973603 | NC_000005.8 | 11448451 | A | G | 0.000769562 | CTNND2 | catenin (cadherin-associated protein), delta 2 (ne | intron |
| 3451458 | 13141523 | 23728801 | NC_000004.9 | 48630197 | A | G | 0.000771589 | | | |
| 4650399 | 1546886 | 24065134 | NC_000020.9 | 40011278 | G | A | 0.000772004 | | | |
| 4440396 | 6546094 | 24276517 | NC_000002.9 | 64785093 | G | A | 0.000776583 | SERTAD2 | SERTA domain containing 2 | intron |
| 3705423 | 8069941 | 24213783 | NC_000017.9 | 5668399 | C | T | 0.000784662 | | | |
| 3615642 | 6896703 | 24379569 | NC_000005.8 | 131549194 | C | G | 0.000796285 | P4HA2 | procollagen-proline, 2-oxoglutarate 4-dioxygenase | down |
| 3615642 | 6896703 | 24379569 | NC_000005.8 | 131549194 | C | G | 0.000796285 | LOC389325 | LOC389325 | intron |
| 2430737 | 1412517 | 24694486 | NC_000009.9 | 25202649 | G | A | 0.000797914 | | | |
| 2686520 | 1347454 | 24021434 | NC_000015.8 | 34154319 | T | C | 0.000799132 | | | |
| 4300783 | 7688340 | 23738179 | NC_000004.9 | 18873919 | T | C | 0.003063641 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 3396691 | 17795478 | 24308194 | NC_000004.9 | 8221394 | C | | | | actin binding LIM protein family, member 2 | |
| | | | | | | T | 0.000800284 | ABLIM2 | | intron |
| 4539519 | 2999896 | 24241332 | NC_000001.8 | 13570501 | T | C | 0.000803654 | LOC126755 | hypothetical protein LOC126755 | intron |
| 3601018 | 300911 | 24389878 | NC_000004.9 | 144634360 | G | T | 0.000605937 | GAB1 | GRB2-associated binding protein 1 | intron |
| 1264660 | 1346793 | 24630907 | NC_000002.9 | 55881932 | T | C | 0.000609531 | | | |
| 354693 | 1208255 | 24004239 | NC_000006.9 | 134174739 | T | G | 0.000811026 | MGC34034 | hypothetical protein MGC34034 | up |
| 3583256 | 12593575 | 23437814 | NC_000015.8 | 76177964 | C | T | 0.000811042 | CIB2 | calcium and integrin binding family member 2 | down |
| 1088435 | 3795823 | 23874649 | NC_000001.8 | 111438911 | G | A | 0.000832231 | FLJ22457 | hypothetical protein FLJ22457 | down |
| 1088435 | 3795823 | 23874649 | NC_000001.8 | 111438911 | G | A | 0.000832231 | CEPT1 | choline/ethanolamine phosphotransferase | exon |
| 1942166 | 4739907 | 23588448 | NC_000008.9 | 80751774 | C | T | 0.00083384 | | | |
| 1129535 | 16856889 | 23845714 | NC_000001.8 | 163000954 | A | G | 0.000836922 | | | |
| 4105591 | 291765 | 23454706 | NC_000009.9 | 90746565 | C | T | 0.000850109 | SYK | spleen tyrosine kinase | down |
| 2703938 | 1368369 | 24198560 | NC_000005.8 | 150948496 | G | A | 0.000850927 | | | |
| 213800 | 2300522 | 24569307 | NC_000014.7 | 80566393 | G | T | 0.000852209 | TSHR | thyroid stimulating hormone receptor | intron |
| 1895302 | 13255161 | 23480571 | NC_000008.9 | 32041263 | C | T | 0.000866257 | | | |
| 3443893 | 9683673 | 23338304 | NC_000004.9 | 23337542 | A | G | 0.000868687 | | | |
| 4548839 | 7638112 | 23303275 | NC_000003.9 | 72666539 | C | T | 0.913882826 | | | |
| 2081816 | 6539043 | 24011662 | NC_000012.9 | 101579685 | G | C | 0.019303335 | | | |
| 815642 | 8082686 | 23638776 | NC_000017.9 | 12485779 | G | A | 0.000871805 | FLJ34690 | hypothetical protein FLJ34690 | down |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 91200 | 2836070 | 24132451 | NC_000021.7 | 41896583 | A | G | 0.001800824 | | | |
| 1643940 | 10500568 | 24431903 | NC_000016.8 | 71151888 | C | T | 0.000875549 | | | |
| 2110397 | 10507409 | 24035110 | NC_000013.9 | 33016027 | A | T | 0.000883575 | | | |
| 2246286 | 16913371 | 24100647 | NC_000010.8 | 52498121 | T | C | 0.000885831 | PRKG1 | protein kinase, cGMP-dependent, type I | up |
| 946690 | 9518812 | 24455100 | NC_000013.9 | 87351779 | A | G | 0.000886272 | | | |
| 751920 | 17033285 | 24156052 | NC_000002.9 | 45401284 | T | A | 0.000889669 | UNQ6975 | similar to NGNL6975 | up |
| 3450991 | 17472113 | 24659280 | NC_000004.9 | 48336590 | T | A | 0.000889198 | ZAR1 | zygote arrest 1 | intron |
| 3450991 | 17472113 | 24659280 | NC_000004.9 | 48336590 | T | A | 0.000889198 | SLC10A4 | solute carrier family 10 (sodium/bile acid cotrans | down |
| 3450991 | 17472113 | 24659280 | NC_000004.9 | 48336590 | T | A | 0.000889198 | KIAA0826 | KIAA0826 protein | down |
| 1938621 | 13260143 | 24539906 | NC_000008.9 | 77369603 | A | T | 0.000892627 | | | |
| 674217 | 7544640 | 23173406 | NC_000001.8 | 37486507 | A | T | 0.000895043 | | | |
| 3380230 | 17067831 | 23439759 | NC_000005.8 | 166358869 | A | C | 0.003818814 | | | |
| 3643521 | 7683446 | 23879802 | NC_000004.9 | 178893145 | T | G | 0.000896634 | LOC285500 | | intron |
| 2834089 | 2605232 | 24659589 | NC_000004.9 | 48895608 | T | G | 0.000905655 | FLJ21511 | hypothetical protein FLJ21511 | intron |
| 4044112 | 7446326 | 24668029 | NC_000002.9 | 2170914 | G | A | 0.000913877 | | | |
| 4120648 | 967751 | 23503390 | NC_000011.8 | 34814660 | T | G | 0.000916161 | | | |
| 3304862 | 1911904 | 24387400 | NC_000005.8 | 98127160 | G | A | 0.0009169653 | RGMB | RGM domain family, member B | up |
| 1362142 | 12692585 | 23260110 | NC_000002.9 | 160906348 | A | G | 0.000920643 | | | |
| 1665956 | 324224 | 24625492 | NC_000011.8 | 21942789 | A | G | 0.000934587 | | | |
| 4520312 | 356260 | 24699158 | NC_000011.8 | 126947359 | A | G | 0.000938236 | | | |
| 3640565 | 6553774 | 23912274 | NC_000004.9 | 175479969 | A | G | 0.000939523 | | | |
| 3568851 | 7162035 | 23552037 | NC_000015.8 | 79842138 | T | C | 0.000952883 | | | |
| 181627 | 1189273 | 23637650 | NC_000014.7 | 56029785 | T | C | 0.001504799 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 1162094 | 16852249 | 23179254 | NC_000001.8 | 200436116 | T | C | | ATP2B4 | ATPase, Ca++ transporting, plasma membrane 4 | intron |
| 4636961 | 217756 | 24336011 | NC_000011.8 | 16762736 | G | T | 0.000957193 | PLEKHA7 | pleckstrin homology domain containing, family A member 7 | down |
| 4636961 | 217756 | 24336011 | NC_000011.8 | 16762736 | G | T | 0.000959247 | LOC283278 | | intron |
| 4037595 | 6841316 | 24222076 | NC_000004.9 | 138899576 | G | A | 0.050448615 | | | |
| 4222457 | 1171442 | 24710935 | NC_000018.8 | 21458701 | G | A | 0.003455805 | LOC441817 | | intron |
| 4567541 | 2291248 | 23482706 | NC_000012.9 | 124144188 | C | T | 0.000969047 | AACS | acetoacetyl-CoA synthetase | intron |
| 213336 | 2236179 | 24571630 | NC_000014.7 | 81022995 | A | G | 0.000972578 | SEL1L | sel-1 suppressor of lin-12-like (C. elegans) | intron |
| 4281007 | 1000031 | 24067213 | NC_000018.8 | 44615439 | G | A | 0.000974941 | KIAA0427 | KIAA0427 | intron |
| 2249625 | 2384311 | 23622802 | NC_000010.8 | 55231153 | C | T | 0.011312669 | LOC387683 | LOC399775 | down |
| 1662075 | 4393295 | 24099985 | NC_000011.8 | 19328483 | G | A | 0.000983308 | | | |
| 4164684 | 2130882 | 24027887 | NC_000015.8 | 96314849 | T | C | 0.305326425 | ARRDC4 | arrestin domain containing 4 | exon |
| 4228325 | 1735169 | 24057079 | NC_000008.9 | 146037858 | G | A | 0.000984964 | ZNF7 | zinc finger protein 7 (KOX 4, clone HF.16) | exon |
| 4228325 | 1735169 | 24057079 | NC_000008.9 | 146037858 | G | A | 0.000984964 | COMMD5 | COMM domain containing 5 | exon |
| 603100 | 918979 | 24418519 | NC_000007.11 | 37243524 | G | T | 0.000986907 | ELMO1 | engulfment and cell motility 1 (ced-12 homolog, C. | intron |
| 1515525 | 17743380 | 24399461 | NC_000006.9 | 97418992 | C | T | 0.000991359 | | | |

Fig. 2 (cont.)

| SNP_ID | REFSNP_ID | SUBSNP_ID | ACCESSION_ID | POSITION | ALLELE_1 | ALLELE_2 | Ptrend_weighted | gene_name | geneDescription | HIT_TYPE |
|---|---|---|---|---|---|---|---|---|---|---|
| 472022 | 10278690 | 23987736 | NC_000007.11 | 96829683 | T | A | 0.00269045 | | | |
| 2404865 | 4855915 | 23955743 | NC_000003.9 | 118266086 | G | C | 0.000993514 | | | |
| 2749673 | 1422893 | 24466412 | NC_000005.8 | 153000786 | C | A | 0.000994764 | GRIA1 | glutamate receptor, ionotropic, AMPA 1 | intron |
| 4379421 | 7367948 | 24282262 | NC_000001.8 | 113004700 | A | G | 0.000995549 | LOC128322 | similar to Nuclear transport factor 2 (NTF-2) (Pla | down |
| 2478264 | 9889782 | 23638741 | NC_000017.9 | 21318809 | G | A | 0.000998024 | | | |

Fig. 2 (cont.)

MARKERS FOR BREAST CANCER

CROSS REFERENCE TO RELATED APPLICATIONS

This application is a continuation of U.S. Ser. No. 14/738,639, filed Jun. 12, 2015, which is a continuation of U.S. Ser. No. 12/370,972, filed Feb. 13, 2009, now U.S. Pat. No. 9,068,229, issued Jun. 30, 2015, which is a divisional of U.S. Ser. No. 11/606,634, filed Nov. 29, 2006, which claims priority to and benefit of U.S. Provisional Application No. 60/740,971, filed Nov. 29, 2005, and also claims priority to and benefit of U.S. Provisional Application No. 60/781,483, filed Mar. 10, 2006, the contents of each of which are hereby incorporated by reference in their entirety.

BACKGROUND OF THE INVENTION

Breast cancer, like other common cancers, shows familial clustering. Numerous epidemiological studies have demonstrated that, overall, the disease is approximately twice as common in first degree relatives of breast cancer patients[1]. Family studies, and particularly twin studies, suggest that most if not all of this clustering has a genetic basis[2,3]. For example, Peto and Mack[3] estimated that the risk of breast cancer in the MZ twin of an affected woman was approximately four-fold greater than the risk to a sister of a case.

Several breast cancer susceptibility genes have already been identified, most importantly BRCA1 and BRCA2. Mutations in these genes confer a high risk of breast cancer (of the order of 65% and 45%, respectively, by age 70)[4]. Mutation screening of population-based series of breast cancer cases has shown that only about 15% of the familial risk of breast cancer can be explained by mutations in these genes[5,6]. The other known breast cancer susceptibility genes (TP53, PTEN, ATM, CHEK2) make only small contributions to the familial risk (because the predisposing mutations are rare and/or confer only small risks). In total therefore, the known breast cancer susceptibility genes have been estimated to account for no more than 20% of the familial risk[7].

Genetic variation in risk may result from rare highly-penetrant mutations (such as those in BRCA1 and BRCA2) or from variants conferring more moderate risks. Several lines evidence suggest strongly that high penetrance mutations are not major contributors to the residual familial risk of breast cancer. Firstly, mutation screening of multiple case families has found that the large majority of cases with a very strong family history (for example four or more affected relatives) harbor mutations in BRCA1 or BRCA2[8]. Secondly, despite extensive efforts over the past nine years, genetic linkage studies have not identified any further linked loci[9,10]. Thirdly, segregation analyses of large series of breast cancer families have found, after adjusting for BRCA1 and BRCA2, no evidence for a further major dominant breast cancer susceptibility allele[11,12]. In the largest such analysis, Antoniou et al.[13] found that the most parsimonious model for breast cancer was a polygenic model, equivalent to a large number of loci of small effect combining multiplicatively.

While the above analyses suggest that several low penetrance breast cancer susceptibility genes remain to be detected, the precise number of such genes is unknown. Moreover, in the prior art, it is unclear whether such susceptibility alleles are common or rare in the population. The subject application focuses on alleles that are relatively common (frequencies greater than 5%) and identification of such loci is performed herein on a genome-wide basis.

SUMMARY OF THE INVENTION

The invention includes the identification of polymorphic loci that are correlated with breast cancer phenotypes, such as susceptibility to breast cancer. FIGS. 1 and 2 provides descriptions of the phenotypic loci. FIG. 1 provides descriptions of preferred phenotypic loci. Accordingly, this invention provides previously unknown correlations between various polymorphisms and breast cancer susceptibility phenotypes. The detection of these polymorphisms (or loci linked thereto), accordingly, provides robust and precise methods and systems for identifying patients that are at risk for breast cancer. In addition, the identification of these polymorphisms provides high-throughput systems and methods for identifying modulators of breast cancer.

Therefore, in one aspect, the invention provides methods of identifying a breast cancer phenotype for an organism or biological sample derived therefrom. The method includes detecting, in the organism or biological sample, a polymorphism or a locus closely linked thereto, the polymorphism being selected from a polymorphism of FIG. 1, wherein the polymorphism is associated with a breast cancer phenotype. The methods further include correlating the polymorphism or locus to the phenotype.

The organism is typically a mammal, and is preferably a human patient, most typically a human female patient (although breast cancer does occur in men, and the associations noted herein may be applicable to male patients as well). Similarly, the biological sample is typically derived from a mammal, e.g., a human patient, e.g., following appropriate informed consent practices. The methods can be used to detect breast cancer markers in samples taken from human patients, or can be used to detect markers in biological samples (e.g., cells, including primary and cultured cells) derived therefrom.

The polymorphisms can be detected by any available method, including amplification, hybridization to a probe or array, or the like. In one specific embodiment, Detection includes amplifying the polymorphism, linked locus or a sequence associated therewith (e.g., flanking sequences, transcribed sequences or the like) and detecting the resulting amplicon. For example, in one embodiment, amplifying includes a) admixing an amplification primer or amplification primer pair with a nucleic acid template isolated from the organism or biological sample. The primer or primer pair can be complementary or partially complementary to a region proximal to or including the polymorphism or linked locus, and are capable of initiating nucleic acid polymerization by a polymerase on the nucleic acid template. The primer or primer pair is extended in a DNA polymerization reaction comprising a polymerase and the template nucleic acid to generate the amplicon. In certain aspects, the amplicon is optionally detected by a process that includes hybridizing the amplicon to an array, digesting the amplicon with a restriction enzyme, or real-time PCR analysis. Optionally, the amplicon can be fully or partially sequenced, e.g., by hybridization. Typically, amplification can include performing a polymerase chain reaction (PCR), reverse transcriptase PCR (RT-PCR), or ligase chain reaction (LCR) using nucleic acid isolated from the organism or biological sample as a template in the PCR, RT-PCR, or LCR. Other technologies can be substituted for amplification, e.g., use of branched DNA (bDNA) probes.

In typical embodiments, the polymorphism or linked locus can include a SNP. Example alleles include those described in FIGS. 1 and/or 2. Relevant polymorphisms can be those, e.g., of FIG. 1 (most preferred) or FIG. 2. Preferred polymorphisms include SNPs selected from the group of SNPs described by SNP identification numbers consisting of: SNP ID 2312116, SNP ID 1622530, SNP ID 3712013, SNP ID 1509710, SNP ID 843029, SNP ID 1990126 (rs13281615), SNP ID 604819, SNP ID 3025734, SNP ID 1152499, SNP ID 4415909, SNP ID 1732681, SNP ID 4281579, SNP ID 4454457, SNP ID 2616199, SNP ID1720694, SNP ID 4077723, SNP ID 3711990, SNP ID 3337858, SNP ID 4093095, SNP ID 4213825, SNP ID 3488617, SNP ID 3610210, SNP ID 3451239, SNP ID 1582533, SNP ID 3488150, SNP ID 2770052, SNP ID 4141351, SNP ID 1335030, SNP ID 2211665, and SNP ID 4538418. These identification numbers are Perlegen SNP identification numbers (Perlegen Sciences, Inc. in Mountain View, Calif.), which are publicly available and can be viewed with considerable associated information at Perlegen.com, by using the company's available genome browser genome(dot)perlegen(dot)com/browser/index(dot)html. Wild card characters (e.g., "*" symbols) can be added at the beginning of the SNP_ID to identify pertinent information for all alleles of the SNP, e.g., following the complete instructions provided. This database also links to the NCBI genomic database, thereby providing considerable additional information for the relevant genes and polymorphisms. These SNPs include SNPs associated with, e.g., the following genes: FGFR2, A2BP1, TNRC9, H19, FSTL5, LSP1, LOC388927, UNQ9391, HCN1, LOC441192, TNRC9, NR3C2, KIAA0826, FLJ31033, AACS, FRMD4A and SEC31L2 (See also, FIG. 1). Polymorphisms linked to these genes are, accordingly, also preferred SNPs that can be associated with breast cancer polymorphisms.

Optionally, and, in certain embodiments, preferably, the method includes detecting polymorphisms in more than one such gene (e.g., in certain convenient applications, several polymorphisms can be detected simultaneously for a single patient to more completely determine or assign the relevant phenotype). Thus, in one aspect, the invention includes detecting a plurality of polymorphisms or linked loci in a plurality of said genes. This can include, e.g., detecting at least one polymorphism for each of: SNP ID 2312116, SNP ID 1622530, SNP ID 3712013, SNP ID 1509710 and SNP ID 84302, and/or polymorphism in FGFR2, A2BP1, TNRC9, H19, and FSTL5. Similarly, the method can include detecting at least one polymorphism for each of: SNP ID 2312116, SNP ID 1622530, SNP ID 3712013, SNP ID 1509710, SNP ID 843029, SNP ID 1990126, SNP ID 604819, SNP ID 3025734, SNP ID 1152499, SNP ID 4415909, SNP ID 1732681, SNP ID 4281579, SNP ID 4454457, SNP ID 2616199, SNP ID 1720694, SNP ID 4077723, SNP ID 3711990, SNP ID 3337858, SNP ID 4093095, SNP ID 4213825, SNP ID 3488617, SNP ID 3610210, SNP ID 3451239, SNP ID 1582533, SNP ID 3488150, SNP ID 2770052, SNP ID 4141351, SNP ID 1335030, SNP ID 2211665, and SNP ID 4538418, or at least one polymorphism in each of: FGFR2, A2BP1, TNRC9, H19, FSTL5, LSP1, LOC388927, UNQ9391, HCN1, LOC441192, TNRC9, NR3C2, KIAA0826, FLJ31033, AACS, FRMD4A and SEC31L2. In general, any combination of these or any other polymorphism/gene/locus in the figures herein can be detected, and all such combinations are optionally a feature of the invention, whether listed expressly or not. Probes or primers of the invention useful in detecting the polymorphisms herein can include a nucleotide sequence of a polymorphism of FIGS. 1 and/or 2, a flanking sequence thereof, or a complementary nucleic acid thereof, or a transcribed product thereof (e.g., a nRNA or mRNA form produced from a genomic sequence, e.g., by transcription or splicing). Polymorphisms can also be detected in a polypeptide sequence, e.g., for any polypeptide sequence transcribed from a given allelic form of a nucleic acid.

In general, any polymorphism that is linked to a QTL can be used as a marker for the QTL. Thus, markers linked to a given polymorphism of the Figures can be used as proxy markers for the given polymorphism. In general, the closer the linkage, the better the marker will be for a QTL/polymorphism. Thus, desirably, the linked locus can be a closely linked locus that is about 5 cM or less (and, optionally, 1 cM or less) from the polymorphism.

The methods optionally include correlating the polymorphism or linked locus to the breast cancer phenotype by referencing a look up table that comprises correlation information for alleles of the polymorphism or linked locus and the breast cancer phenotype. Databases that are used for this correlation can be heuristic, or otherwise capable of refining correlations based on information obtained by correlating marker-trait information.

Related compositions are a feature of the invention, e.g., a composition comprising a plurality of marker probes or amplification primers that detect or amplify a plurality of polymorphisms associated with a breast cancer phenotype, e.g., as described herein. The primers/probes can be array based, or free in solution.

In an additional aspect, methods of identifying a modulator of a breast cancer phenotype are also provided. The methods include contacting a potential modulator to a gene or gene product, e.g., wherein the gene or gene product comprises or is closely linked to a polymorphism described herein (e.g., in FIGS. 1 and/or 2). An effect of the potential modulator on the gene or gene product is detected, thereby identifying whether the potential modulator modulates the phenotype.

The gene or gene product optionally includes a particular allele of a polymorphism selected from those listed herein, but modulators can also be tested on other alleles to identify modulators that modulate alleles specifically or non-specifically. The effects that can be tested for include any of: (a) increased or decreased expression of the gene or gene product in the presence of the modulator; (b) increased or decreased activity of the gene product in the presence of the modulator; and, (c) an altered expression pattern of the gene or gene product in the presence of the modulator.

A kit for treatment of a breast cancer phenotype can include a modulator identified by the method and instructions for administering the modulator to a patient to treat the phenotype.

In addition to the methods noted above, kits and systems for practicing the methods are also a feature of the invention. For example, a system for identifying a breast cancer phenotype for an organism or biological sample derived therefrom are one feature of the invention. The system includes, e.g., a set of marker probes or primers configured to detect at least one allele of one or more polymorphism or linked locus, e.g., where the polymorphism is any polymorphism noted herein, e.g., in FIG. 1 or 2. The system optionally additionally includes a detector that is configured to detect one or more signal outputs from the set of marker probes or primers, or an amplicon produced from the set of marker probes or primers, thereby identifying the presence or absence of the allele. System instructions (e.g., software embodied in a computer of the system) that correlate the presence or absence of the allele with a predicted phenotype are typically included as components of the system.

Systems for screening modulators are also a feature of the invention. The systems can include, e.g., genes linked to a polymorphism herein, or an encoded expression products of the gene. The systems will typically include a detector that measures increased or decreased expression of the gene or gene product in the presence of the modulator; increased or decreased activity of the gene product in the presence of the modulator; or an altered expression pattern of the gene or gene product in the presence of the modulator. The systems can also include fluid handling elements for mixing and aliquotting modulator and/or the gene or product, mixing them, performing laboratory operations (e.g., purification, synthesis, cell culture, etc.). System instructions for recording modulator effects and, optionally, for selecting modulators are also an optional feature of these systems.

Kits for performing any of the methods herein are another feature of the invention. Such kits can include probes or amplicons for detecting any polymorphism herein, appropriate packaging materials, and instructions for practicing the methods.

The polymorphisms and genes, and corresponding marker probes, amplicons or primers described above can be embodied in any system herein, either in the form of physical nucleic acids or polypeptides, or in the form of system instructions that include sequence information for the nucleic acids and polypeptides. For example, the system can include primers or amplicons corresponding to (or that amplify a portion of) a gene or polymorphism described herein, such as SNP ID 2312116, SNP ID 1622530, SNP ID 3712013, SNP ID 1509710, SNP ID 843029, SNP ID 1990126, SNP ID 604819, SNP ID 3025734, SNP ID 1152499, SNP ID 4415909, SNP ID 1732681, SNP ID 4281579, SNP ID 4454457, SNP ID 2616199, SNP ID 1720694, SNP ID 4077723, SNP ID 3711990, SNP ID 3337858, SNP ID 4093095, SNP ID 4213825, SNP ID 3488617, SNP ID 3610210, SNP ID 3451239, SNP ID 1582533, SNP ID 3488150, SNP ID 2770052, SNP ID 4141351, SNP ID 1335030, SNP ID 2211665, and SNP ID 4538418, and/or FGFR2, A2BP1, TNRC9, H19, FSTL5, LSP1, LOC388927, UNQ9391, HCN1, LOC441192, TNRC9, NR3C2, KIAA0826, FLJ31033, AACS, FRMD4A and SEC31L2. As in the methods above, the set of marker probes or primers optionally detects a plurality of polymorphisms in a plurality of said genes or genetic loci. Thus, for example, the set of marker probes or primers detects at least one polymorphism in each of these polymorphisms or genes, or any other polymorphism, gene or locus in the Figures herein. Any such probe or primer can include a nucleotide sequence of any such polymorphism or gene, or a complementary nucleic acid thereof, or a transcribed product thereof (e.g., a nRNA or mRNA form produced from a genomic sequence, e.g., by transcription or splicing).

Many alternate variants are embodiments of the invention. For example, the detector typically detects one or more light emission that is indicative of the presence or absence of the allele. The instructions typically comprise at least one look-up table that includes a correlation between the presence or absence of the allele and the phenotype. The system optionally comprises a sample for testing, e.g., a genomic DNA, amplified genomic DNA, cDNA, amplified cDNA, RNA, or amplified RNA. The sample can be from or derived from a mammal such as a human patient.

All features of the methods, kits and systems can be used together in combination. For example, systems for detecting modulators can be used for practicing methods of modulator detection. Systems for identifying correlations between breast cancer phenotypes and polymorphisms can be used for practicing the methods herein. Kits can be used for practicing the methods herein. Thus, described features of the systems, methods and kits can be applied to the different systems, methods and kits herein.

BRIEF DESCRIPTION OF THE FIGURES

FIG. 1 is a table of preferred polymorphisms, genes and related information for polymorphisms associated with breast cancer.

FIG. 2 is a table of preferred polymorphisms, genes and related information for polymorphisms associated with breast cancer.

Definitions

It is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a," "an" and "the," for example, optionally include plural referents unless the content clearly dictates otherwise. Thus, for example, reference to "a probe" optionally includes a plurality of probe molecules; similarly, depending on the context, use of the term "a nucleic acid" optionally includes, as a practical matter, many copies of that nucleic acid molecule. Letter designations for genes or proteins can refer to the gene form and/or the protein form, depending on context. One of skill is fully able to relate the nucleic acid and amino acid forms of the relevant biological molecules by reference to the sequences herein, known sequences and the genetic code.

Unless otherwise indicated, nucleic acids are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "phenotype" is a trait or collection of traits that is/are observable in an individual or population. The trait can be quantitative (a quantitative trait, or QTL) or qualitative. For example, susceptibility to breast cancer is a phenotype that can be monitored according to the methods, compositions, kits and systems herein.

A "breast cancer susceptibility phenotype" is a phenotype that displays a predisposition towards developing breast cancer in an individual. A phenotype that displays a predisposition for breast cancer, can, for example, show a higher likelihood that the cancer will develop in an individual with the phenotype than in members of a relevant general population under a given set of environmental conditions (diet, physical activity regime, geographic location, etc.).

A "polymorphism" is a locus that is variable; that is, within a population, the nucleotide sequence at a polymorphism has more than one version or allele. The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. One example of a polymorphism is a "single nucleotide polymorphism" (SNP), which is a polymorphism at a single nucleotide position in a genome (the nucleotide at the specified position varies between individuals or populations).

An allele "positively" correlates with a trait when it is linked to it and when presence of the allele is an indictor that the trait or trait form will occur in an individual comprising the allele. An allele negatively correlates with a trait when it is linked to it and when presence of the allele is an indicator that a trait or trait form will not occur in an individual comprising the allele.

A marker polymorphism or allele is "correlated" or "associated" with a specified phenotype (breast cancer susceptibility, etc.) when it can be statistically linked (positively or negatively) to the phenotype. That is, the specified polymorphism occurs more commonly in a case population (e.g., breast cancer patients) than in a control population (e.g., individuals that do not have breast cancer). This correlation is often inferred as being causal in nature, but it need not be-simple genetic linkage to (association with) a locus for a trait that underlies the phenotype is sufficient for correlation/association to occur.

A "favorable allele" is an allele at a particular locus that positively correlates with a desirable phenotype, e.g., resistance to breast cancer, e.g., an allele that negatively correlates with predisposition to breast cancer. A favorable allele of a linked marker is a marker allele that segregates with the favorable allele. A favorable allelic form of a chromosome segment is a chromosome segment that includes a nucleotide sequence that positively correlates with the desired phenotype, or that negatively correlates with the unfavorable phenotype at one or more genetic loci physically located on the chromosome segment.

An "unfavorable allele" is an allele at a particular locus that negatively correlates with a desirable phenotype, or that correlates positively with an undesirable phenotype, e.g., positive correlation to breast cancer susceptibility. An unfavorable allele of a linked marker is a marker allele that segregates with the unfavorable allele. An unfavorable allelic form of a chromosome segment is a chromosome segment that includes a nucleotide sequence that negatively correlates with the desired phenotype, or positively correlates with the undesirable phenotype at one or more genetic loci physically located on the chromosome segment.

"Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line or population (e.g., cases or controls) by averaging the allele frequencies of a sample of individuals from that line or population. Similarly, one can calculate the allele frequency within a population of lines by averaging the allele frequencies of lines that make up the population.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal position or region. For example, a polymorphic locus is a position or region where a polymorphic nucleic acid, trait determinant, gene or marker is located. In a further example, a "gene locus" is a specific chromosome location (region) in the genome of a species where a specific gene can be found. Similarly, the term "quantitative trait locus" or "QTL" refers to a locus with at least two alleles that differentially affect the expression or alter the variation of a quantitative or continuous phenotypic trait in at least one genetic background, e.g., in at least one population or progeny.

A "marker," "molecular marker" or "marker nucleic acid" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, nRNA, mRNA, a cDNA, etc.), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Nucleic acids are "complementary" when they specifically hybridize in solution, e.g., according to Watson-Crick base pairing rules. A "marker locus" is a locus that can be used to track the presence of a second linked locus, e.g., a linked or correlated locus that encodes or contributes to the population variation of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus. In one aspect, the present invention provides marker loci correlating with a phenotype of interest, e.g., breast cancer susceptibility/resistance. Each of the identified markers is expected to be in close physical and genetic proximity (resulting in physical and/or genetic linkage) to a genetic element, e.g., a QTL, that contributes to the relevant phenotype. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of allele specific hybridization (ASH), detection of single nucleotide extension, detection of amplified variable sequences of the genome, detection of self-sustained sequence replication, detection of simple sequence repeats (SSRs), detection of single nucleotide polymorphisms (SNPs), or detection of amplified fragment length polymorphisms (AFLPs).

A "genetic map" is a description of genetic linkage (or association) relationships among loci on one or more chromosomes (or linkage groups) within a given species, generally depicted in a diagrammatic or tabular form. "Mapping" is the process of defining the linkage relationships of loci through the use of genetic markers, populations segregating for the markers, and standard genetic principles of recombination frequency. A "map location" is an assigned location on a genetic map relative to linked genetic markers where a specified marker can be found within a given species. The term "chromosome segment" or designates a contiguous linear span of genomic DNA that resides on a single chromosome. Similarly, a "haplotype" is a set of genetic loci found in the heritable material of an individual or population (the set can be a contiguous or non-contiguous). In the context of the present invention genetic elements such as one or more alleles herein and one or more linked marker alleles can be located within a chromosome segment and are also, accordingly, genetically linked, a specified genetic recombination distance of less than or equal to 20 centimorgan (cM) or less, e.g., 15 cM or less, often 10 cM or less, e.g., about 9, 8, 7, 6, 5, 4, 3, 2, 1, 0.75, 0.5, 0.25, or 0.1 CM or less.

That is, two closely linked genetic elements within a single chromosome segment undergo recombination during meiosis with each other at a frequency of less than or equal to about 20%, e.g., about 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25%, or 0.1% or less. Once a correlation/association between a phenotype (e.g., breast cancer predisposition) and a polymorphic locus in identified, e.g., by comparison of a statistical frequency of the locus in cases and controls, any polymorphism that is linked to the associated locus can be used as a proxy marker for the correlated locus.

A "genetic recombination frequency" is the frequency of a recombination event between two genetic loci. Recombination frequency can be observed by following the segregation of markers and/or traits during meiosis. In the context of this invention, a marker locus is "associated with" another marker locus or some other locus (for example, a breast cancer susceptibility locus), when the relevant loci are part of the same linkage group, due to physical chromosomal association, and are in linkage disequilibrium. This occurs when the marker locus and a linked locus are found together in progeny more frequently than if the loci segregate randomly. Similarly, a marker locus can also be associated with a trait, e.g., a marker locus can be "associated with" a given trait (breast cancer resistance or susceptibility) when the marker locus is in linkage disequilibrium with the trait (this can be detected, e.g., when the marker is found more commonly in case versus control populations). The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random frequency (in the case of co-segregating traits, the loci that underlie the traits are in sufficient proximity to each other). Linked loci co-segregate more than 50% of the time, e.g., from about 51% to about 100% of the time. Advantageously, the two loci are located in close proximity such that recombination between homologous chromosome pairs does not occur between the two loci during meiosis with high frequency, e.g., such that closely linked loci co-segregate at least about 80% of the time, more preferably at least about 85% of the time, still more preferably at least 90% of the time, e.g., 91%, 92%, 93%, 94%, 95%, 96%, 97%, 98%, 99%, 99.5%, 99.75%, or 99.90% or more of the time.

The phrase "closely linked," in the present application, means that recombination between two linked loci (e.g., a SNP such as one identified in FIG. 1 or 2 (e.g., that is correlated to a breast cancer phenotype by comparison of case and control populations) and a second linked polymorphism) occurs with a frequency of equal to or less than about 20%. Put another way, the closely (or "tightly") linked loci co-segregate at least 80% of the time. Marker loci are especially useful in the present invention when they are closely linked to target loci (e.g., QTL for breast cancer, or, alternatively, simply other breast cancer marker loci). The more closely a marker is linked to a target locus, the better an indicator for the target locus that the marker is. Thus, in one embodiment, tightly linked loci such as a marker locus and a second locus display an inter-locus recombination frequency of about 20% or less, e.g., 15% or less, e.g., 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination frequency of about 1% or less, e.g., about 0.75% or less, more preferably about 0.5% or less, or yet more preferably about 0.25% or less, or still more preferably about 0.1% or less. Two loci that are localized to the same chromosome, and at such a distance that recombination between the two loci occurs at a frequency of less than about 20%, e.g., 15%, more preferably 10% (e.g., about 9%, 8%, 7%, 6%, 5%, 4%, 3%, 2%, 1%, 0.75%, 0.5%, 0.25%, 0.1% or less) are also said to be "proximal to" each other. When referring to the relationship between two linked genetic elements, such as a genetic element contributing to a trait and a proximal marker, "coupling" phase linkage indicates the state where the "favorable" allele at the trait locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for breast cancer susceptibility) is physically associated on the same chromosome strand as an "unfavorable" allele at the proximal marker locus, and the two "favorable" alleles are not inherited together (i.e., the two loci are "out of phase" with each other).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise nontranscribed (e.g., chromosome structural sequences, promoter regions, enhancer regions, etc.) and/or non-translated sequences (e.g., introns), whereas spliced RNA/cDNA typically do not have introns. A "template genomic nucleic acid" is a genomic nucleic acid that serves as a template in an amplification reaction (e.g., a polymerase based amplification reaction such as PCR, a ligase mediated amplification reaction such as LCR, a transcription reaction, or the like).

An "exogenous nucleic acid" is a nucleic acid that is not native to a specified system (e.g., a germplasm, cell, individual, etc.), with respect to sequence, genomic position, or both. As used herein, the terms "exogenous" or "heterologous" as applied to polynucleotides or polypeptides typically refers to molecules that have been artificially supplied to a biological system (e.g., a cell, an individual, etc.) and are not native to that particular biological system. The terms can indicate that the relevant material originated from a source other than a naturally occurring source, or can refer to molecules having a non-natural configuration, genetic location or arrangement of parts.

The term "introduced" when referring to translocating a heterologous or exogenous nucleic acid into a cell refers to the incorporation of the nucleic acid into the cell using any methodology. The term encompasses such nucleic acid introduction methods as "transfection," "transformation" and "transduction."

As used herein, the term "vector" is used in reference to polynucleotides or other molecules that transfer nucleic acid segment(s) into a cell. The term "vehicle" is sometimes used interchangeably with "vector." A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a mammalian cell expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes. In one optional embodiment, a gene corresponding to a loci herein is cloned into an expression vector and expressed, with the gene product(s) to be used in the methods and systems herein for modulator identification.

A specified nucleic acid is "derived from" a given nucleic acid when it is constructed using the given nucleic acid's sequence, or when the specified nucleic acid is constructed using the given nucleic acid.

A "gene" is one or more sequence(s) of nucleotides in a genome that together encode one or more expressed molecule, e.g., an RNA, or polypeptide. The gene can include coding sequences that are transcribed into RNA which may then be translated into a polypeptide sequence, and can include associated structural or regulatory sequences that aid in replication or expression of the gene. Genes of interest in the present invention include those that include or are closely linked to the loci of FIGS. 1 and/or 2.

A "genotype" is the genetic constitution of an individual (or group of individuals) at one or more genetic loci. Genotype is defined by the allele(s) of one or more known loci of the individual, typically, the compilation of alleles inherited from its parents. A "haplotype" is the genotype of an individual at a plurality of genetic loci on a single DNA strand. Typically, the genetic loci described by a haplotype are physically and genetically linked, i.e., on the same chromosome strand.

A "set" of markers or probes refers to a collection or group of markers or probes, or the data derived therefrom, used for a common purpose, e.g., identifying an individual with a specified phenotype (e.g., breast cancer resistance or susceptibility). Frequently, data corresponding to the markers or probes, or derived from their use, is stored in an electronic medium. While each of the members of a set possess utility with respect to the specified purpose, individual markers selected from the set as well as subsets including some, but not all of the markers, are also effective in achieving the specified purpose.

A "look up table" is a table that correlates one form of data to another, or one or more forms of data with a predicted outcome to which the data is relevant. For example, a look up table can include a correlation between allele data and a predicted trait that an individual comprising one or more given alleles is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM or RAM, flash memory, etc.), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless correction, or the like.

"System instructions" are instruction sets that can be partially or fully executed by the system. Typically, the instruction sets are present as system software.

A "translation product" is a product (typically a polypeptide) produced as a result of the translation of a nucleic acid. A "transcription product" is a product (e.g., an RNA, optionally including mRNA, or, e.g., a catalytic or biologically active RNA) produced as a result of transcription of a nucleic acid (e.g., a DNA).

An "array" is an assemblage of elements. The assemblage can be spatially ordered (a "patterned array") or disordered (a "randomly patterned" array). The array can form or comprise one or more functional elements (e.g., a probe region on a microarray) or it can be non-functional.

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein, such reference may include derivatives of the DNA such as amplicons, RNA transcripts thereof, etc.

DETAILED DESCRIPTION

Overview

The invention includes new correlations between the polymorphisms of FIGS. 1 and 2 (and genes that include or are proximal to the polymorphisms) and breast cancer predisposition. Certain alleles in, and linked to, these genes or gene products are predictive of the likelihood that an individual possessing the relevant alleles will develop breast cancer. Accordingly, detection of these alleles, by any available method, can be used for diagnostic purposes such as early detection of susceptibility to breast cancer, prognosis for patients that present with breast cancer and in assisting in diagnosis, e.g., where current criteria are insufficient for a definitive diagnosis.

The identification that the polymorphisms, genes or gene products of FIG. 1 or 2, are correlated with breast cancer phenotypes also provides a platform for screening potential modulators of breast cancer disorders. Modulators of the activity of any genes or encoded proteins corresponding to the polymorphisms of FIGS. 1 and 2, are expected to have an effect on breast cancer. Thus, methods of screening, systems for screening and the like, are features of the invention. Modulators identified by these screening approaches are also a feature of the invention.

Kits for the diagnosis and treatment of breast cancer, e.g., comprising probes to identify relevant alleles, packaging materials, and instructions for con-elating detection of relevant alleles to breast cancer are also a feature of the invention. These kits can also include modulators of breast cancer and/or instructions for treating patients using conventional methods.

Methods of Identifying Breast Cancer Predisposition

As noted, the invention provides the discovery that certain genes or other loci of FIGS. 1 and 2, are linked to breast cancer phenotypes. Thus, by detecting markers (e.g., the SNPs in FIG. 1 or 2 or loci closely linked thereto) that con-elate, positively or negatively, with the relevant phenotypes, it can be determined whether an individual or population is likely to be comprise these phenotypes. This provides enhanced early detection options to identify patients that are at risk for breast cancer, making it possible, in some cases, to prevent actual development of cancer, e.g., by taking early preventative action (e.g., any existing therapy, including prophylactic surgery, diet, exercise, available medications, etc.). In addition, use of the various markers herein also adds certainty to existing diagnostic techniques for identifying whether a patient is suffering from a particular form of breast cancer. Furthermore, knowledge of whether there is a molecular basis for the disease can also assist in determining patient prognosis, e.g., by providing an indication of how likely it is that a patient can respond to conventional therapy for breast cancer. Disease treatment can also be targeted based on what type of molecular disorder the patient displays.

Detection methods for detecting relevant alleles can include any available method, e.g., amplification technologies. For example, detection can include amplifying the polymorphism or a sequence associated therewith and detecting the resulting amplicon. This can include admixing an amplification primer or amplification primer pair with a nucleic acid template isolated from the organism or biological sample (e.g., comprising the SNP or other polymorphism), e.g., where the primer or primer pair is complementary or partially complementary to at least a portion of the gene or tightly linked polymorphism, or to a sequence proximal thereto. The primer is typically capable of initiating nucleic acid polymerization by a polymerase on the nucleic acid template. The primer or primer pair is extended, e.g., in a DNA polymerization reaction (PCR, RT-PCR, etc.) comprising a polymerase and the template nucleic acid to generate the amplicon. The amplicon is detected by any available detection process, e.g., sequencing, hybridizing the amplicon to an array (or affixing the amplicon to an array and hybridizing probes to it), digesting the amplicon with a restriction enzyme (e.g., RFLP), real-time PCR analysis, single nucleotide extension, allele-specific hybridization, or the like.

The correlation between a detected polymorphism and a trait can be performed by any method that can identify a relationship between an allele and a phenotype. Most typically, these methods involve referencing a look up table that comprises correlations between alleles of the polymorphism and the phenotype. The table can include data for multiple allele-phenotype relationships and can take account of additive or other higher order effects of multiple allele-phenotype relationships, e.g., through the use of statistical tools such as principle component analysis, heuristic algorithms, etc.

Within the context of these methods, the following discussion first focuses on how markers and alleles are linked and how this phenomenon can be used in the context of methods for identifying breast cancer phenotypes, and then focuses on marker detection methods. Additional sections below discuss data analysis.

Markers, Linkage and Alleles

In traditional linkage (or association) analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher: frequency are more closely linked than traits which are inherited together with lower (but still above random) frequency. Traits are linked because the genes which underlie the traits reside near one another on the same chromosome. The further apart on a chromosome the genes reside, the less likely they are to segregate together, because homologous chromosomes recombine during meiosis. Thus, the further apart on a chromosome the genes reside, the more likely it is that there will be a recombination event during meiosis that will result in two genes segregating separately into progeny.

A common measure of linkage (or association) is the frequency with which traits cosegregate. This can be expressed as a percentage of cosegregation (recombination frequency) or, also commonly, in centiMorgans (cM), which are actually a reciprocal unit of recombination frequency. The cM is named after the pioneering geneticist Thomas Hunt Morgan and is a unit of measure of genetic recombination frequency. One cM is equal to a 1% chance that a trait at one genetic locus will be separated from a trait at another locus due to recombination in a single generation (meaning the traits segregate together 99% of the time). Because chromosomal distance is approximately proportional to the frequency of recombination events between traits, there is an approximate physical distance that correlates with recombination frequency. For example, in humans, 1 cM correlates, on average, to about 1 million base pairs (1 Mbp).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL for breast cancer), due to recombination in a single generation. The markers herein, e.g., those listed in FIGS. 1 and 2, can correlate with breast cancer. This means that the markers comprise or are sufficiently proximal to a QTL for breast cancer that they can be used as a predictor for the trait itself. This is extremely useful in the context of disease diagnosis.

The polymorphisms of FIGS. 1 and 2 have been identified as being more prevalent in case (breast cancer patient) versus control populations. Any marker that is linked to a trait locus of interest (e.g., in the present case, a QTL or identified linked marker locus for breast cancer, e.g., as in FIGS. 1 and 2) can be used as a marker for that trait. Thus, in addition to the markers noted in FIGS. 1 and 2, other markers closely linked to the markers itemized in these Figures can also usefully predict the presence of the marker alleles indicated in the figures (and, thus, the relevant phenotypic trait). Such linked markers are particularly useful when they are sufficiently proximal to a given locus so that they display a low recombination frequency with the given locus. In the present invention, such closely linked markers are a feature of the invention. Closely linked loci display a recombination frequency with a given marker of about 20% or less (the given marker is within 20 cM of the given marker). Put another way, closely linked loci co-segregate at least 80% of the time. More preferably, the recombination frequency is 10% or less, e.g., 9%, 8%, 7%, 6%, 5%, 4%, 3%, 2%, 1%, 0.5%, 0.25%, or 0.1% or less. In one typical class of embodiments, closely linked loci are within 5 cM or less of each other.

As one of skill in the art will recognize, recombination frequencies (and, as a result, map positions) can vary depending on the map used (and the markers that are on the map). Additional markers that are closely linked to (e.g., within about 20 cM, or more preferably within about 10 cM, or still more preferably within 5 cM of) the markers identified in FIGS. 1 and 2 may readily be used for identification of QTL for breast cancer predisposition.

Marker loci are especially useful in the present invention when they are closely linked to target loci (e.g., QTL for breast cancer phenotypes, or, alternatively, simply other marker loci that are, themselves, linked to such QTL) that they are being used as markers for. The more closely a marker is linked to a target locus that encodes or affects a phenotypic trait, the better an indicator for the target locus that the marker is (due to the reduced cross-over frequency between the target locus and the marker). Thus, in one embodiment, closely linked loci such as a marker locus and a second locus (e.g., a given marker locus of FIGS. 1 and 2 and an additional second locus) display an inter-locus cross-over frequency of about 20% or less, e.g., 15% or less, preferably 10% or less, more preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or 0.1% or less. Thus, the loci are about 20 cM, 19 cM, 18 cM, 17 cM, 16 cM, 15 cM, 14 cM, 13 cM, 12 cM, 11 cM, 10 cM, 9 cM, 8 cM, 7 cM, 6 cM, 5 cM, 4 cM, 3 cM, 2 cM, 1 cM, 0.75 cM, 0.5 cM, 0.25 cM, 0 or 0.1 cM or less apart. Put another way, two loci that are localized to the same chromosome, and at such a distance that recombination between the two loci occurs at a frequency of less than 20% (e.g., about 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25%, 0.1% or less) are said to be "proximal to" each other. In one aspect, linked markers are within 100 kb (which correlates in humans to about 0.1 cM, depending on local recombination rate), e.g., 50 kb, or even 20 kb or less of each other.

When referring to the relationship between two genetic elements, such as a genetic element contributing to breast cancer, and a proximal marker, "coupling" phase linkage indicates the state where the "favorable" allele at the locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for breast cancer) is physically linked with an "unfavorable" allele at the proximal marker locus, and the two "favorable" alleles are not inherited together (i.e., the two loci are "out of phase" with each other).

In addition to tracking SNP and other polymorphisms in the genome, and in corresponding expressed nucleic acids and polypeptides, expression level differences between individuals or populations for the gene products of FIGS. 1 and 2, in either mRNA or protein form, can also correlate to breast cancer. Accordingly, markers of the invention can include any of, e.g.: genomic loci, transcribed nucleic acids, spliced nucleic acids, expressed proteins, levels of transcribed nucleic acids, levels of spliced nucleic acids, and levels of expressed proteins.

Marker Amplification Strategies

Amplification primers for amplifying markers (e.g., marker loci) and suitable probes to detect such markers or to genotype a sample with respect to multiple marker alleles, are a feature of the invention. In FIGS. 1 and 2, specific loci for amplification are provided, along with known flanking sequences in the design of such primers. For example, primer selection for long-range PCR is described in U.S. Ser. No. 10/042,406, filed Jan. 9, 2002 and U.S. Ser. No. 10/236,480, filed Sep. 5, 2002; for short-range PCR, U.S. Ser. No. 10/341,832, filed Jan. 14, 2003 provides guidance with respect to primer selection. Also, there are publicly available programs such as "Oligo" available for primer design. With such available primer selection and design software, the publicly available human genome sequence and the polymorphism locations as provided in FIGS. 1 and 2, one of skill can construct primers to amplify the SNPs of the present invention. Further, it will be appreciated that the precise probe to be used for detection of a nucleic acid comprising a SNP (e.g., an amplicon comprising the SNP) can vary, e.g., any probe that can identify the region of a marker amplicon to be detected can be used in conjunction with the present invention. Further, the configuration of the detection probes can, of course, vary. Thus, the invention is not limited to the sequences recited herein.

Indeed, it will be appreciated that amplification is not a requirement for marker detection—for example, one can directly detect unamplified genomic DNA simply by performing a Southern blot on a sample of genomic DNA. Procedures for performing Southern blotting, standard amplification (PCR, LCR, or the like) and many other nucleic acid detection methods are well established and are taught, e.g., in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis).

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH), detection of single nucleotide extension, array hybridization (optionally including ASH), or other methods for detecting single nucleotide polymorphisms (SNPs), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme marker detection, no1ihern analysis (where expression levels are used as markers), quantitative amplification of mRNA or cDNA, or the like. While the exemplary markers provided in the Figures are SNP markers, any of the aforementioned marker types can be employed in the context of the invention to identify linked loci that correlate with a breast cancer phenotype.

Example Techniques for Marker Detection

The invention provides molecular markers that comprise or are linked to QTL for breast cancer phenotypes. The markers find use in disease predisposition diagnosis, prognosis, treatment, etc. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, northern analysis, allele specific hybridization (ASH), array based hybridization, amplified variable sequences of the genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. Any of these methods are readily adapted to high throughput analysis.

Some techniques for detecting genetic markers utilize hybridization of a probe nucleic acid to nucleic acids corresponding to the genetic marker (e.g., amplified nucleic acids produced using genomic DNA as a template). Hybridization formats, including, but not limited to: solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology— Hybridization with Nucleic Acid Probes* Elsevier, New York, as well as in Sambrook, Berger and Ausubel.

For example, markers that comprise restriction fragment length polymorphisms (RFLP) are detected, e.g., by hybridizing a probe which is typically a subfragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals or populations. Determining one or more restriction enzyme that produces informative fragments for each allele of a marker is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (2003) *Handbook of Fluorescent Probes and Research Chemicals Ninth Edition* by Molecular Probes, Inc. (Eugene Oreg.). Additional details regarding marker detection strategies are found below.

Amplification-Based Detection Methods

PCR, RT-PCR and LCR are in particularly broad use as amplification and amplification-detection methods for amplifying nucleic acids of interest (e.g., those comprising marker loci), facilitating detection of the nucleic acids of interest. Details regarding the use of these and other amplification methods can be found in any of a variety of standard texts, including, e.g., Sambrook, Ausubel, and Berger. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also, Ausubel, Sambrook and Berger, above. These methods can also be used to quantitatively amplify mRNA or corresponding cDNA, providing an indication of expression levels of mRNA that correspond to a gene product corresponding to the genes or gene products of FIGS. 1 and 2 in an individual. Differences in expression levels for these genes between individuals, families, lines and/or populations can be used as markers for breast cancer phenotypes.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." *Nucleic Acids Res.* 26:2150-2155; Tyagi and Kramer (1996) "Molecular beacons: probes that fluoresce upon hybridization" *Nature Biotechnology* 14:303-308; Blok and Kramer (1997) "Amplifiable hybridization probes containing a molecular switch" *Mol Cell Probes* 11:187-194; Hsuih et al. (1997) "Novel, ligationdependent PCR assay for detection of hepatitis C in serum" *J Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Bonnet et al. (1999) "Thermodynamic basis of the chemical specificity of structured DNA probes" *Proc. Natl. Acad. Sci. U.S.A.* 96:6171-6176; Fang et al. (1999) "Designing a novel molecular beacon for surface-immobilized DNA hybridization studies" *J. Am. Chem. Soc.* 121:2921-2922; Marras et al. (1999) "Multiplex detection of single-nucleotide variation using molecular beacons" *Genet. Anal. Biomol. Eng.* 14:151-156; and Vet et al. (1999) "Multiplex detection of four pathogenic retroviruses using molecular beacons" *Proc. Natl. Acad. Sci. U.S.A.* 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" USP 6, 150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO92/02638.

Other similar methods include e.g. fluorescence resonance energy transfer between two adjacently hybridized probes, e.g., using the "LightCycler®" format described in U.S. Pat. No. 6,174,670.

Array-Based Marker Detection

Array-based detection can be performed using commercially available arrays, e.g., from Affymetrix (Santa Clara, Calif.) or other manufacturers. Reviews regarding the operation of nucleic acid arrays include Sapolsky et al. (1999) "High-throughput polymorphism screening and genotyping with high-density oligonucleotide arrays." *Genetic Analysis: Biomolecular Engineering* 14:187-192; Lockhart (1998) "Mutant yeast on drugs" *Nature Medicine* 4:1235-1236; Fodor (1997) "Genes, Chips and the Human Genome." *FASEB Journal* 11:A879; Fodor (1997) "Massively Parallel Genomics." *Science* 277: 393-395; and Chee et al. (1996) "Accessing Genetic Information with High-Density DNA Arrays." *Science* 274:610-614. Array based detection is a preferred method for identification markers of the invention in samples, due to the inherently high-throughput nature of array based detection.

A variety of probe arrays have been described in the literature and can be used in the context of the present invention for detection of markers that can be correlated to the phenotypes noted herein. For example, DNA probe array chips or larger DNA probe array wafers (from which individual chips would otherwise be obtained by breaking up the wafer) are used in one embodiment of the invention. DNA probe array wafers generally comprise glass wafers on which high density arrays of DNA probes (short segments of DNA) have been placed. Each of these wafers can hold, for example, approximately 60 million DNA probes that are used to recognize longer sample DNA sequences (e.g., from individuals or populations, e.g., that comprise markers of interest). The recognition of sample DNA by the set of DNA probes on the glass wafer takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a marker found in the nucleic acid is present. One can also use this approach to perform ASH, by controlling the hybridization conditions to permit single nucleotide discrimination, e.g., for SNP identification and for genotyping a sample for one or more SNPs. Arrays provide one convenient embodiment for detecting multiple polymorphic markers simultaneously (or in series). For example, breast cancer susceptibility detection arrays can be constructed in which any or all of the polymorphisms noted herein (or polymorphisms linked thereto) are detected simultaneously to assign a breast cancer susceptibility phenotype. Of course, any detection technology (PCR, LCR, real-time PCR, etc.) can similarly be used, e.g., with multiplex amplification/detection reactions, or simply by running several separate reactions, e.g., simultaneously or in series.

The use of DNA probe arrays to obtain allele information typically involves the following general steps: design and manufacture of DNA probe arrays, preparation of the sample, hybridization of sample DNA to the array, detection of hybridization events and data analysis to determine sequence. Preferred wafers are manufactured using a process adapted from semiconductor manufacturing to achieve cost effectiveness and high quality, and are available, e.g., from Affymetrix, Inc of Santa Clara, Calif.

For example, probe arrays can be manufactured by light-directed chemical synthesis processes, which combine solid-phase chemical synthesis with photolithographic fabrication techniques as employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays can be synthesized simultaneously on a large glass wafer. This parallel process enhances reproducibility and helps achieve economies of scale.

Once fabricated, DNA probe arrays can be used to obtain data regarding presence and/or expression levels for markers of interest. The DNA samples may be tagged with biotin and/or a fluorescent reporter group by standard biochemical methods. The labeled samples are incubated with an array, and segments of the samples bind, or hybridize, with complementary sequences on the array. The array can be washed and/or stained to produce a hybridization pattern. The array is then scanned and the patterns of hybridization are detected by emission of light from the fluorescent reporter groups. Additional details regarding these procedures are found in the examples below. Because the identity and position of each probe on the array is known, the nature of the DNA sequences in the sample applied to the array can be determined. When these arrays are used for genotyping experiments, they can be referred to as genotyping arrays. As already noted, the genotype of any or all of the polymorphisms noted herein, e.g., in FIG. 1 and/or FIG. 2 can be detected, e.g., to assign a breast cancer predisposition phenotype.

The nucleic acid sample to be analyzed is isolated, amplified and, typically, labeled with biotin and/or a fluorescent reporter group. The labeled nucleic acid sample is then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labeled nucleic acid, which is now bound to the probe array. Probes that most clearly match the labeled nucleic acid produce stronger signals than those that have mismatches. Since the sequence and position of each probe on the an-ay are known, by complementarity, the identity of the nucleic acid sample applied to the probe array can be identified.

In one embodiment, two DNA samples may be differentially labeled and hybridized with a single set of the designed genotyping arrays. In this way two sets of data can be obtained from the same physical arrays. Labels that can be used include, but are not limited to, cychrome, fluorescein, or biotin (later stained with phycoerythrin-streptavidin after hybridization). Two-color labeling is described in U.S. Pat. No. 6,342,355, incorporated herein by reference in its entirety. Each array may be scanned such that the signal from both labels is detected simultaneously, or may be scanned twice to detect each signal separately.

Intensity data is collected by the scanner for all the markers for each of the individuals that are tested for presence of the marker. The measured intensities are a measure indicative of the amount of a particular marker present in the sample for a given individual (expression level and/or number of copies of the allele present in an individual, depending on whether genomic or expressed nucleic acids are analyzed). This can be used to determine whether the individual is homozygous or heterozygous for the marker of interest. The intensity data is processed to provide corresponding marker information for the various intensities.

Additional Details Regarding Amplified Variable Sequences, SSR, AFLP, ASH, SNPs and Isozyme Markers Amplified variable sequences refer to amplified sequences of the genome which exhibit high nucleic acid residue variability between members of the same species. All organisms have variable genomic sequences and each organism (with the exception of a clone, e.g., a cloned cell) has a different set of variable sequences. Once identified, the presence of specific variable sequence can be used to predict phenotypic traits. Preferably, DNA from the genome serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially, in vitro, under substantially isothermal conditions by using three enzymatic activities involved in retroviral replication: (1) reverse transcriptase, (2) Rnase H, and (3) a DNA-dependent RNA polymerase (Guatelli et al. (1990) *Proc Natl Acad Sci USA* 87:1874). By mimicking the retroviral strategy of RNA replication by means of cDNA intermediates, this reaction 25 accumulates cDNA and RNA copies of the original target.

Amplified fragment length polymophisms (AFLP) can also be used as genetic markers (Vos et al. (1995) *Nucl Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping (Becker et al. (1995) *Mol Gen Genet* 249:65; and Meksem et al. (1995) *Mol Gen Genet* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection may be accomplished via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe.

The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis or array based detection are also appropriate.

Isozyme markers can be employed as genetic markers, e.g., to track isozyme markers linked to the markers herein. Isozymes are multiple forms of enzymes that differ from one another in their amino acid, and therefore their nucleic acid sequences. Some isozymes are multimeric enzymes contain slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

Additional Details Regarding Nucleic Acid Amplification

As noted, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in the references noted above, e.g., Innis, Sambrook; Ausubel, and Berger. Additional details are found in Mullis et al. (1987) U.S. Pat. No. 4,683,202; Amheim & Levinson (Oct. 1, 1990) C&EN 36-47; The Journal Of NIH Research (1991) 3, 81-94; (Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem 35, 1826; Landegren et al., (1988) Science 241, 5 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of amplifying large nucleic acids by PCR, which is useful in the context of positional cloning of genes linked to the polymorphisms herein (FIGS. 1 and/or 2), are further summarized in Cheng et al. (1994) Nature 369: 684, and the references therein, in which PCR amplicons of up to 40 kb are generated. Methods for long-range PCR are disclosed, for example, in U.S. patent application Ser. No. 10/042,406, filed Jan. 9, 2002, entitled "Algorithms for Selection of Primer Pairs"; U.S. patent application Ser. No. 10/236,480, filed Sep. 9, 2002, entitled "Methods for Amplification of Nucleic Acids"; and U.S. Pat. No. 6,740,510, issued May 25, 2004, entitled "Methods for 15 Amplification of Nucleic Acids". U.S. Ser. No. 10/341,832 (filed Nov. 24, 2003) also provides details regarding primer picking methods for performing short range PCR.

Detection of Protein Expression Products

Proteins such as those encoded by the genes noted in FIGS. 1 and/or 2 are encoded by nucleic acids, including those comprising markers that are correlated to the phenotypes of interest herein. For a description of the basic paradigm of molecular biology, including the expression (transcription and/or translation) of DNA into RNA into protein, see, Alberts et al. (2002) Molecular Biology of the Cell, 4th Edition Taylor and Francis, Inc., ISBN: 0815332181 ("Alberts"), and Lodish et al. (1999) Molecular Cell Biology, 4$^{th}$ Edition W H Freeman & Co, ISBN: 071673706X ("Lodish"). Accordingly, proteins corresponding to the genes in FIGS. 1 and/or 2 can be detected as markers, e.g., by detecting different protein isotypes between individuals or populations, or by detecting a differential presence, absence or expression level of such a protein of interest (e.g., a gene product of FIGS. 1 and/or 2).

A variety of protein detection methods are known and can be used to distinguish markers. In addition to the various references noted supra, a variety of protein manipulation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

"Proteomic" detection methods, which detect many proteins simultaneously have been described. These can include various multidimensional electrophoresis methods (e.g., 2-d gel electrophoresis), mass spectrometry based methods (e.g., SELDI, MALDI, electrospray, etc.), or surface plasmon reasonance methods. For example, in MALDI, a sample is usually mixed with an appropriate matrix, placed on the surface of a probe and examined by laser desorption/ionization. The technique of MALDI is well known in the art. See, e.g., U.S. Pat. No. 5,045,694 (Beavis et al.), U.S. Pat. No. 5,202,561 (Gleissmann et al.), and U.S. Pat. No. 6,111,251 (Hillenkamp). Similarly, for SELDI, a first aliquot is contacted with a solid support-bound (e.g., substrate-bound) adsorbent. A substrate is typically a probe (e.g., a biochip) that can be positioned in an interrogatable relationship with a gas phase ion spectrometer. SELDI is also a well known technique, and has been applied to diagnostic proteomics. See, e.g. Issaq et al. (2003) "SELDI-TOF MS for Diagnostic Proteomics" *Analytical Chemistry* 75:149A-155A.

In general, the above methods can be used to detect different forms (alleles) of proteins and/or can be used to detect different expression levels of the proteins (which can be due to allelic differences) between individuals, families, lines, populations, etc. Differences in expression levels, when controlled for environmental factors, can be indicative of different alleles at a QTL for the gene of interest, even if the encoded differentially expressed proteins are themselves identical. This occurs, for example, where there are multiple allelic forms of a gene in non-coding regions, e.g., regions such as promoters or enhancers that control gene expression. Thus, detection of differential expression levels can be used as a method of detecting allelic differences.

In other aspect of the present invention, a gene complising, in linkage disequilibrium with, or under the control of a nucleic acid associated with a breast cancer phenotype may exhibit differential allelic expression. "Differential allelic expression" as used herein refers to both qualitative and quantitative differences in the allelic expression of multiple alleles of a single gene present in a cell. As such, a gene displaying differential allelic expression may have one allele expressed at a different time or level as compared to a second allele in the same cell/tissue. For example, an allele associated with a breast cancer phenotype may be expressed at a higher or lower level than an allele that is not associated with the breast cancer phenotype, even though both are alleles of the same gene and are present in the same cell/tissue. Differential allelic expression and analysis methods are disclosed in detail in U.S. patent application Ser. No. 10/438,184, filed May 13, 2003 and U.S. patent application Ser. No. 10/845,316, filed May 12, 2004, both of which are entitled "Allele-specific expression patterns." Detection of a differential allelic expression pattern of one or more nucleic acids, or fragments, derivatives, polymorphisms, variants or complements thereof, associated with a breast cancer phenotype is a prognostic and diagnostic for susceptibility/resistance to breast cancer; likewise, detection of a differential allelic expression pattern of one or more nucleic acids, or fragments, derivatives, polymorphisms, variants or complements thereof, associated with a breast cancer phenotype is prognostic for and diagnostic of breast cancer and breast cancer treatment outcomes.

Additional Details Regarding Types of Markers Appropriate for Screening

The biological markers that are screened for correlation to the phenotypes herein can be any of those types of markers that can be detected by screening, e.g., genetic markers such as allelic variants of a genetic locus (e.g., as in SNPs), expression markers (e.g., presence or quantity of mRNAs and/or proteins), and/or the like.

The nucleic acid of interest to be amplified, transcribed, translated and/or detected in the methods of the invention can be essentially any nucleic acid, though nucleic acids derived from human sources are especially relevant to the detection of markers associated with disease diagnosis and clinical applications. The sequences for many nucleic acids and amino acids (from which nucleic acid sequences can be derived via reverse translation) are available, including for the genes/proteins of FIGS. 1 and/or 2. Common sequence repositories for known nucleic acids include GenBank® EMBL, DDBJ and the NCBI. Other repositories can easily be identified by searching the internet. The nucleic acid to be amplified, transcribed, translated and/or detected can be an RNA (e.g., where amplification includes R T-PCR or LCR, the Van-Gelder Eberwine reaction or RiboSPIA) or DNA (e.g., amplified DNA, cDNA or genomic DNA), or even any analogue thereof (e.g., for detection of synthetic nucleic acids or analogues thereof, e.g., where the sample of interest includes or is used to derive or synthesize artificial nucleic acids). Any variation in a nucleic acid sequence or expression level between individuals or populations can be detected as a marker, e.g., a mutation, a polymorphism, a single nucleotide polymorphism (SNP), an allele, an isotype, expression of an RNA or protein, etc. One can detect variation in sequence, expression levels or gene copy numbers as markers that can be correlated to a breast cancer phenotype.

For example, the methods of the invention are useful in screening samples derived from patients for a marker nucleic acid of interest, e.g., from bodily fluids (blood, saliva, urine etc.), biopsy, tissue, and/or waste from the patient. Thus, tissue biopsies, stool, sputum, saliva, blood, lymph, tears, sweat, urine, vaginal secretions, ejaculatory fluid or the like can easily be screened for nucleic acids by the methods of the invention, as can essentially any tissue of interest that contains the appropriate nucleic acids. These samples are typically taken, following informed consent, from a patient by standard medical laboratory methods.

Prior to amplification and/or detection of a nucleic acid comprising a marker, the nucleic acid is optionally purified from the samples by any available method, e.g., those taught in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook"); and/or *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")). A plethora of kits are also commercially available for the purification of nucleic acids from cells or other samples (see, e.g., EasyPrep™, FlexiPrep™, both from Pharmacia Biotech; StrataClean™, from Stratagene; and, QIAprep™ from Qiagen). Alternately, samples can simply be directly subjected to amplification or detection, e.g., following aliquotting and/or dilution.

Examples of markers can include polymorphisms, single nucleotide polymorphisms, presence of one or more nucleic acids in a sample, absence of one or more nucleic acids in a sample, presence of one or more genomic DNA sequences, absence or one or more genomic DNA sequences, presence of one or more mRNAs, absence of one or more mRNAs, expression levels of one or more mRNAs, presence of one or more proteins, expression levels of one or more proteins, and/or data derived from any of the preceding or combinations thereof. Essentially any number of markers can be detected, using available methods, e.g., using array technologies that provide high density, high throughput marker mapping. Thus, at least about 10, 100, 1,000, 10,000, or even 100,000 or more genetic markers can be tested, simultaneously or in a serial fashion (or combination thereof), for correlation to a relevant phenotype, in the first and/or second population. Combinations of markers can also be desirably tested, e.g., to identify genetic combinations or combinations of expression patterns in populations that are correlated to the phenotype.

As noted, the biological marker to be detected can be any detectable biological component. Commonly detected markers include genetic markers (e.g., DNA sequence markers present in genomic DNA or expression products thereof) and expression markers (which can reflect genetically coded factors, environmental factors, or both). Where the markers are expression markers, the methods can include determining a first expression profile for a first individual or population (e.g., of one or more expressed markers, e.g., a set of expressed markers) and comparing the first expression profile to a second expression profile for the second individual or population. In this example, correlating expression marker(s) to a particular phenotype can include correlating the first or second expression profile to the phenotype of interest.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), *Tetrahedron Letts.*, 22(20): 1859-1862, e.g., using a commercially available automated synthesizer, e.g., as described in Needham-VanDevanter et al. (1984) *Nucleic Acids Res.*, 12:6159-6168. Oligonucleotides, including modified oligonucleotides can also be ordered from a variety of commercial sources known to persons of skill. There are many commercial providers ofoligo synthesis services, and thus this is a broadly accessible technology. Any nucleic acid can be custom ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others. Similarly, PNAs can be custom ordered from any of a variety of sources, such as PeptidoGenic (pkim@ccnet.com), HTI Bio-products, inc. (htibio.com), BMA Biomedicals Ltd (U.K.), Bio Synthesis, Inc., and many others.

In Silico Marker Detection

In some embodiments, in silica methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors. The entire human genome has been sequenced and, thus, sequence information can be used to identify marker regions, flanking nucleic acids, etc.

Amplification Primers for Marker Detection

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region.

Suitable primers to be used with the invention can be designed using any suitable method. It is not intended that the invention be limited to any particular primer or primer pair. For example, primers can be designed using any suitable software program, such as LASER GENE®, e.g., taking account of publicly available sequence information. Flanking sequences for the polymorphisms identified herein are publicly available; accordingly, suitable amplification primers can be constructed based on well understood base-pairing rules. The sequence of any amplicon can be detected as has already been discussed above, e.g., by hybridization, array hybridization, PCR, real-time PCR, LCR, or the like.

In some embodiments, the primers of the invention are radiolabelled, or labeled by any suitable means (e.g., using a non-radioactive fluorescent tag), to allow for rapid visualization of differently sized amplicons following an amplification reaction without any additional labeling step or visualization step. In some embodiments, the primers are not labeled, and the amplicons are visualized following their size resolution, e.g., following agarose or acrylamide gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the marker loci and alleles herein are not limited to amplifying the entire region of the relevant locus, or any subregion thereof. The primers can generate an amplicon of any suitable length for detection. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Amplicons of any size can be detected using the various technologies described herein. Differences in base composition or size can be detected by conventional methods such as electrophoresis.

Detection of Markers for Positional Cloning

In some embodiments, a nucleic acid probe is used to detect a nucleic acid that comprises a marker sequence. In addition to their role in determining breast cancer phenotypes, such probes can also be used, for example, in positional cloning to isolate nucleotide sequences linked to the marker nucleotide sequence. It is not intended that the nucleic acid probes of the invention be limited to any particular size. In some embodiments, nucleic acid probe is at least 20 nucleotides in length, or alternatively, at least 50 nucleotides in length, or alternatively, at least 100 nucleotides in length, or alternatively, at least 200 nucleotides in length.

A hybridized probe is detected using, e.g., autoradiography, fluorography or other similar detection techniques depending on the label to be detected. Examples of specific hybridization protocols are widely available in the art, see, e.g., Berger, Sambrook, and Ausubel, all herein.

Generation of Transgenic Cells

The present invention also provides cells which are transformed with nucleic acids corresponding to QTL identified according to the invention. For example, such nucleic acids include chromosome intervals (e.g., genomic fragments), genes, ORFs and/or cDNAs that encode genes that correspond or are linked to QTL for breast cancer phenotypes. Additionally, the invention provides for the production of polypeptides that influence breast cancer phenotypes. This is useful, e.g., to influence breast cancers, and for the generation of transgenic cells. These cells provide commercially useful cell lines having defined genes that influence the relevant phenotype, thereby providing a platform for screening potential modulators of phenotype, as well as basic research into the mechanism of action for each of the genes of interest. In addition, gene therapy can be used to introduce desirable genes into individuals or populations thereof. Such gene therapies may be used to provide a treatment for a disorder exhibited by an individual, or may be used as a preventative measure to prevent the development of such a disorder in an individual at risk.

General texts which describe molecular biological techniques for the cloning and manipulation of nucleic acids and production of encoded polypeptides include Berger and Kimmel, *Guide to Molecular Cloning Techniques. Methods in Enzymology* volume 152 Academic Press, Inc., San Diego, Calif. (Berger); Sambrook et al., *Molecular Cloning—A Laboratory Manual* (3rd Ed.). *Vol.* 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004 or later) ("Ausubel")). These texts describe mutagenesis, the use of vectors, promoters and many other relevant topics related to, e.g., the generation of clones that comprise nucleic acids of interest, e.g., genes, marker loci, marker probes, QTL that segregate with marker loci, etc.

Host cells are genetically engineered (e.g., transduced, transfected, transformed, etc.) with the vectors of this invention (e.g., vectors, such as expression vectors which comprise a gene or an ORF derived from or related to a QTL) which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. Additional details regarding nucleic acid introduction methods are found in Sambrook, Berger and Ausubel, infra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. In addition to Sambrook, Berger and Ausubel, all infra, Atlas and Parks (eds) *The Handbook of Microbiological Media* (1993) CRC Press, Boca Raton, Fla. and available commercial literature such as the *Life Science Research Cell Culture Catalogue* (2004) from Sigma-Aldrich, Inc (St Louis, Mo.) ("Sigma-LSRCCC") provide additional details.

Correlating Markers to Phenotypes

One aspect of the invention is a description of correlations between polymorphisms noted in FIGS. 1 and/or 2 and breast cancer phenotypes. An understanding of these correlations can be used in the present invention to correlate information regarding a set of polymorphisms that an individual or sample is determined to possess and a phenotype that they are likely to display. Further, higher order correlations that account for combinations of alleles in one or more different genes can also be assessed for correlations to phenotype.

These correlations can be performed by any method that can identify a relationship between an allele and a phenotype, or a combination of alleles and a combination of phenotypes. For example, alleles in genes or loci in FIGS. 1 and/or 2 can be correlated with one or more breast cancer phenotypes. Most typically, these methods involve referencing a look up table that comprises correlations between alleles of the polymorphism and the phenotype. The table can include data for multiple allele-phenotype relationships and can take account of additive or other higher order effects of multiple allele-phenotype relationships, e.g., through the use of statistical tools such as principle component analysis, heuristic algorithms, etc.

Correlation of a marker to a phenotype optionally includes performing one or more statistical tests for correlation. Many statistical tests are known, and most are computer-implemented for ease of analysis. A variety of statistical methods of determining associations/correlations between phenotypic traits and biological markers are known and can be applied to the present invention. For an introduction to the topic, see, Hartl (1981) *A Primer of Population Genetics* Washington University, Saint Louis Sinauer Associates, Inc. Sunderland, Mass. ISBN: 0-087893-271-2. A variety of appropriate statistical models are described in Lynch and Walsh (1998) *Genetics and Analysis of Quantitative Traits*, Sinauer Associates, Inc. Sunderland Mass. ISBN 0-87893-481-2. These models can, for example, provide for correlations between genotypic and phenotypic values, characterize the influence of a locus on a phenotype, sort out the relationship between environment and genotype, determine dominance or penetrance of genes, determine maternal and other epigenetic effects, determine principle components in an analysis (via principle component analysis, or "PCA"), and the like. The references cited in these texts provides considerable further detail on statistical models for correlating markers and phenotype.

In addition to standard statistical methods for determining correlation, other methods that determine correlations by pattern recognition and training, such as the use of genetic algorithms, can be used to determine correlations between markers and phenotypes. This is particularly useful when identifying higher order correlations between multiple alleles and multiple phenotypes. To illustrate, neural network approaches can be coupled to genetic algorithm-type programming for heuristic development of a structure-function data space model that determines correlations between genetic information and phenotypic outcomes. For example, NNUGA (Neural Network Using Genetic Algorithms) is an available program (e.g., on the world wide web at cs.bgu.ac.il/~omri/NNUGA which couples neural networks and genetic algorithms. An introduction to neural networks can be found, e.g., in Kevin Gurney, An Introduction to Neural Networks, UCL Press (1999) and on the world wide web at shef(dot)ac(dot)uk/psychology/gurney/notes/index(dot) html. Additional useful neural network references include those noted above in regard to genetic algorithms and, e.g., Bishop, Neural Networks for Pattern Recognition, Oxford University Press (1995), and Ripley et al., Pattern Recognition and Neural Networks, Cambridge University Press (1995). Two tables showing exemplary data sets including certain statistical analyses are shown in FIGS. 1 and/or 2.

Additional references that are useful in understanding data analysis applications for using and establishing correlations, principle components of an analysis, neural network modeling and the like, include, e.g., Hinchliffe, Modeling Molecular Structures, John Wiley and Sons (1996), Gibas and Jambeck, Bioinformatics Computer Skills, O'Reilly (2001), Pevzner, Computational Molecular Biology and Algorithmic Approach, The MIT Press (2000), Durbin et al., Biological Sequence Analysis: Probabilistic Models of Proteins and Nucleic Acids, Cambridge University Press (1998), and Rashidi and Buehler, Bioinformatic Basics: Applications in Biological Science and Medicine, CRC Press LLC (2000).

In any case, essentially any statistical test can be applied in a computer implemented model, by standard programming methods, or using any of a variety of "off the shelf" software packages that perform such statistical analyses, including, for example, those noted above and those that are commercially available, e.g., from Partek Incorporated (St.

Peters, Mo.; www.partek.com), e.g., that provide software for pattern recognition (e.g., which provide Partek Pro 2000 Pattern Recognition Software) which can be applied to genetic algorithms for multivariate data analysis, interactive visualization, variable selection, neural network & statistical modeling, etc. Relationships can be analyzed, e.g., by Principal Components Analysis (PCA) mapped mapped scatterplots and biplots, MultiDimensional Scaling (MDS) Multi-Dimensional Scaling (MDS) mapped scatterplots, star plots, etc. Available software for performing correlation analysis includes SAS, Rand MathLab.

The marker(s), whether polymorphisms or expression patterns, can be used for any of a variety of genetic analyses. For example, once markers have been identified, as in the present case, they can be used in a number of different assays for association studies. For example, probes can be designed for microarrays that interrogate these markers. Other exemplary assays include, e.g., the Taqman assays and molecular beacon assays described supra, as well as conventional PCR and/or sequencing techniques.

Additional details regarding association studies can be found in Ser. No. 10/106,097, filed Mar. 26, 2002, entitled "Methods for Genomic Analysis;" Ser. No. 10/042,819, filed Jan. 7, 2002, entitled "Genetic Analysis Systems and Methods;" Ser. No. 10/286,417, filed Oct. 31, 2002, entitled "Methods for Genomic Analysis;" Ser. No. 10/768,788, filed Jan. 30, 2004, entitled "Apparatus and Methods for Analyzing and Charactelizing Nucleic Acid Sequences;" Ser. No. 10/447,685, filed May 28, 2003, entitled "Liver Related Disease Compositions and Methods;" Ser. No. 10/970,761, filed Oct. 20, 2004, entitled "Improved Analysis Methods and Apparatus for Individual Genotyping" (methods for individual genotyping); Ser. No. 10/956,224, filed Sep. 30, 2004, entitled "Methods for Genetic Analysis."

In some embodiments, the marker data is used to perform association studies to show correlations between markers and phenotypes. This can be accomplished by determining marker characteristics in individuals with the phenotype of interest (i.e., individuals or populations displaying the phenotype of interest) and comparing the allele frequency or other characteristics (expression levels, etc.) of the markers in these individuals to the allele frequency or other characteristics in a control group of individuals. Such marker determinations can be conducted on a genome-wide basis, or can be focused on specific regions of the genome (e.g., haplotype blocks of interest). In one embodiment, markers that are linked to the genes or loci in FIGS. 1 and/or 2 are assessed for correlation to one or more specific breast cancer predisposition phenotypes.

In addition to the other embodiments of the methods of the present invention disclosed herein, the methods additionally allow for the "dissection" of a phenotype. That is, a particular phenotypes can (and typically do) result from two or more different genetic bases. For example, a susceptibility phenotype in one individual may be the result of a "defect" (or simply a particular allele-"defect" with respect to a susceptibility phenotype is context dependent, e.g., whether the phenotype is desirable or undesirable in the individual in a given environment) in a gene for in FIGS. 1 and/or 2, while the same basic phenotype in a different individual may be the result of multiple "defects" in multiple genes in FIGS. 1 and/or 2. Thus, scanning a plurality of markers (e.g., as in genome or haplotype block scanning) allows for the dissection of varying genetic bases for similar (or graduated) phenotypes.

As described in the previous paragraph, one method of conducting association studies is to compare the allele frequency (or expression level) of markers in individuals with a phenotype of interest ("case group") to the allele frequency in a control group of individuals. In one method, informative SNPs are used to make the SNP haplotype pattern comparison (an "informative SNP" is genetic SNP marker such as a SNP or subset (more than one) of SNPs in a genome or haplotype block that tends to distinguish one SNP or genome or haplotype pattern from other SNPs, genomes or haplotype patterns). The approach of using informative SNPs has an advantage over other whole genome scanning or genotyping methods known in the art, for instead of reading all 3 billion bases of each individual's genome—or even reading the 3-4 million common SNPs that may be found—only informative SNPs from a sample population need to be detected. Reading these particular, informative SNPs provides sufficient information to allow statistically accurate association data to be extracted from specific experimental populations, as described above.

Thus, in an embodiment of one method of determining genetic associations, the allele frequency of informative SNPs is determined for genomes of a control population that do not display the phenotype. The allele frequency of informative SNPs is also determined for genomes of a population that do display the phenotype. The informative SNP allele frequencies are compared. Allele frequency comparisons can be made, for example, by determining the allele frequency (number of instances of a particular allele in a population divided by the total number of alleles) at each informative SNP location in each population and comparing these allele frequencies. The informative SNPs displaying a difference between the allele frequency of occurrence in the control versus case populations/groups are selected for analysis. Once informative SNPs are selected, the SNP haplotype block(s) that contain the informative SNPs are identified, which in turn identifies a genomic region of interest that is correlated with the phenotype. The genomic regions can be analyzed by genetic or any biological methods known in the art e.g., for use as drug discovery targets or as diagnostic markers.

Systems for Identifying Breast Cancer Phenotypes

Systems for performing the above correlations are also a feature of the invention. Typically, the system will include system instructions that correlate the presence or absence of an allele (whether detected directly or, e.g., through expression levels) with a predicted phenotype. The system instructions can compare detected information as to allele sequence or expression level with a database that includes correlations between the alleles and the relevant phenotypes. As noted above, this database can be multidimensional, thereby including higher-order relationships between combinations of alleles and the relevant phenotypes. These relationships can be stored in any number of look-up tables, e.g., taking the form of spreadsheets (e.g., Excel™ spreadsheets) or databases such as an Access™, SQL™, Oracle™, Paradox™, or similar database. The system includes provisions for inputting sample-specific information regarding allele detection information, e.g., through an automated or user interface and for comparing that information to the look up tables.

Optionally, the system instructions can also include software that accepts diagnostic information associated with any detected allele information, e.g., a diagnosis that a subject with the relevant allele has a particular phenotype. This software can be heuristic in nature, using such inputted associations to improve the accuracy of the look up tables and/or interpretation of the look up tables by the system. A variety of such approaches, including neural networks, Markov modeling, and other statistical analysis are described above.

The invention provides data acquisition modules for detecting one or more detectable genetic marker(s) (e.g., one or more array comprising one or more biomolecular probes, detectors, fluid handlers, or the like). The biomolecular probes of such a data acquisition module can include any that are appropriate for detecting the biological marker, e.g., oligonucleotide probes, proteins, aptamers, antibodies, etc. These can include sample handlers (e.g., fluid handlers), robotics, microfluidic systems, nucleic acid or protein purification modules, arrays (e.g., nucleic acid arrays), detectors, thermocyclers or combinations thereof, e.g., for acquiring samples, diluting or aliquoting samples, purifying marker materials (e.g., nucleic acids or proteins), amplifying marker nucleic acids, detecting amplified marker nucleic acids, and the like.

For example, automated devices that can be incorporated into the systems herein have been used to assess a variety of biological phenomena, including, e.g., expression levels of genes in response to selected stimuli (Service (1998) "Microchips Arrays Put DNA on the Spot" *Science* 282: 396-399), high throughput DNA genotyping (Zhang et al. (1999) "Automated and Integrated System for High-Throughput DNA Genotyping Directly from Blood" *Anal. Chem.* 71:1138-1145) and many others. Similarly, integrated systems for performing mixing experiments, DNA amplification, DNA sequencing and the like are also available. See, e.g., Service (1998) "Coming Soon: the Pocket DNA Sequencer" *Science* 282: 399-401. A variety of automated system components are available, e.g., from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). Similarly, commercially available microfluidic systems that can be used as system components in the present invention include those from Agilent technologies and the Caliper Technologies. Furthermore, the patent and technical literature includes numerous examples of microfluidic systems, including those that can interface directly with microwell plates for automated fluid handling.

Any of a variety of liquid handling and/or array configurations can be used in the systems herein. One common format for use in the systems herein is a microtiter plate, in which the array or liquid handler includes a microtiter tray. Such trays are commercially available and can be ordered in a variety of well sizes and numbers of wells per tray, as well as with any of a variety of functionalized surfaces for binding of assay or array components. Common trays include the ubiquitous 96 well plate, with 384 and 1536 well plates also in common use. Samples can be processed in such trays, with all of the processing steps being performed in the trays. Samples can also be processed in microfluidic apparatus, or combinations of microtiter and microfluidic apparatus.

In addition to liquid phase arrays, components can be stored in or analyzed on solid phase arrays. These arrays fix materials in a spatially accessible pattern (e.g., a grid of rows and columns) onto a solid substrate such as a membrane (e.g., nylon or nitrocellulose), a polymer or ceramic surface, a glass or modified silica surface, a metal surface, or the like. Components can be accessed, e.g., by hybridization, by local rehydration (e.g., using a pipette or other fluid handling element) and fluidic transfer, or by scraping the array or cutting out sites of interest on the array.

The system can also include detection apparatus that is used to detect allele information, using any of the approached noted herein. For example, a detector configured to detect real-time PCR products (e.g., a light detector, such as a fluorescence detector) or an array reader can be incorporated into the system. For example, the detector can be configured to detect a light emission from a hybridization or amplification reaction comprising an allele of interest, wherein the light emission is indicative of the presence or absence of the allele. Optionally, an operable linkage between the detector and a computer that comprises the system instructions noted above is provided, allowing for automatic input of detected allele-specific information to the computer, which can, e.g., store the database information and/or execute the system instructions to compare the detected allele specific information to the look up table.

Probes that are used to generate information detected by the detector can also be incorporated within the system, along with any other hardware or software for using the probes to detect the amplicon. These can include thermocycler elements (e.g., for performing PCR or LCR amplification of the allele to be detected by the probes), arrays upon which the probes are arrayed and/or hybridized, or the like. The fluid handling elements noted above for processing samples, can be used for moving sample materials (e.g., template nucleic acids and/or proteins to be detected) primers, probes, amplicons, or the like into contact with one another. For example, the system can include a set of marker probes or primers configured to detect at least one allele of one or more genes or linked loci associated with a phenotype, where the gene encodes a polymorphism in FIGS. 1 and/or 2. The detector module is configured to detect one or more signal outputs from the set of marker probes or primers, or an amplicon produced from the set of marker probes or primers, thereby identifying the presence or absence of the allele.

The sample to be analyzed is optionally part of the system, or can be considered separate from it. The sample optionally includes e.g., genomic DNA, amplified genomic DNA, cDNA, amplified cDNA, RNA, amplified RNA, proteins, etc., as noted herein. In one aspect, the sample is derived from a mammal such as a human patient.

Optionally, system components for interfacing with a user are provided. For example, the systems can include a user viewable display for viewing an output of computer-implemented system instructions, user input devices (e.g., keyboards or pointing devices such as a mouse) for inputting user commands and activating the system, etc. Typically, the system of interest includes a computer, wherein the various computer-implemented system instructions are embodied in computer software, e.g., stored on computer readable media.

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Sequel™, Oracle™, Paradox™) can be adapted to the present invention by inputting a character string corresponding to an allele herein, or an association between an allele and a phenotype. For example, the systems can include software having the appropriate character string information, e.g., used in conjunction with a user interface (e.g., a GUI in a standard operating system such as a Windows, Macintosh or LINUX system) to manipulate strings of characters. Specialized sequence alignment programs such as BLAST can also be incorporated into the systems of the invention for alignment of nucleic acids or proteins (or corresponding character strings) e.g., for identifying and relating multiple alleles.

As noted, systems can include a computer with an appropriate database and an allele sequence or correlation of the invention. Software for aligning sequences, as well as data sets entered into the software system comprising any of the sequences herein can be a feature of the invention. The computer can be, e.g., a PC (Intel x86 or Pentium chip-compatible DOS™, OS2™ WINDOWS™ WINDOWS NT™, WINDOWS95™, WINDOWS98™, WINDOWS2000, WINDOWSME, or LINUX based machine, a MACINTOSH™, Power PC, or a UNIX based (e.g., SUN™ work station or LINUX based machine) or other commercially common computer which is known to one of skill. Software for entering and aligning or otherwise manipulating sequences is available, e.g., BLASTP and BLASTN, or can easily be constructed by one of skill using a standard programming language such as Visualbasic, Fortran, Basic, Java, or the like.

Methods of Identifying Modulators

In addition to providing various diagnostic and prognostic markers for identifying breast cancer predisposition, etc., the invention also provides methods of identifying modulators of breast cancer phenotypes. In the methods, a potential modulator is contacted to a relevant protein corresponding to a loci in FIGS. 1 and/or 2, or to a nucleic acid that encodes such a protein. An effect of the potential modulator on the gene or gene product is detected, thereby identifying whether the potential modulator modulates the underlying molecular basis for the phenotype.

In addition, the methods can include, e.g., administering one or more putative modulator to an individual that displays a relevant phenotype and determining whether the putative modulator modulates the phenotype in the individual, e.g., in the context of a clinical trial or treatment. This, in turn, determines whether the putative modulator is clinically useful.

The gene or gene product that is contacted by the modulator can include any allelic form noted herein. Allelic forms, whether genes or proteins, that positively correlate to undesirable phenotypes are preferred targets for modulator screening.

Effects of interest that can be screened for include: (a) increased or decreased expression of a gene or gene product in FIGS. 1 and/or 2 in the presence of the modulator, (b) a change in the timing or location of expression; (c) or a change in localization of the proteins corresponding to loci of FIGS. 1 and/or 2 in the presence of the modulator.

The precise format of the modulator screen will, of course, vary, depending on the effect(s) being detected and the equipment available. Northern analysis, quantitative RT-PCR and/or array-based detection formats can be used to distinguish expression levels of genes noted above. Protein expression levels can also be detected using available methods, such as western blotting, ELISA analysis, antibody hybridization, BIAcore, or the like. Any of these methods can be used to distinguish changes in expression levels that result from a potential modulator.

Accordingly, one may screen for potential modulators for activity or expression. For example, potential modulators (small molecules, organic molecules, inorganic molecules, proteins, hormones, transcription factors, or the like) can be contacted to a cell comprising an allele of interest and an effect on activity or expression (or both) of a gene or protein corresponding to a loci in FIGS. 1 and/or 2 can be detected, e.g., via northern analysis or quantitative (optionally real time) RT-PCR, before and after application of potential expression modulators. Similarly, promoter regions of the various genes (e.g., generally sequences in the region of the start site of transcription, e.g., within 5 kb of the start site, e.g., 1 kb, or less e.g., within 500 bp or 250 bp or 100 bp of the start site) can be coupled to repolier constructs (CAT, beta-galactosidase, luciferase or any other available reporter) and can be similarly be tested for expression activity modulation by the potential modulator. In either case, the assays can be performed in a high-throughput fashion, e.g., using automated fluid handling and/or detection systems, in serial or parallel fashion. Similarly, activity modulators can be tested by contacting a potential modulator to an appropriate cell using any of the activity detection methods herein, regardless of whether the activity that is detected is the result of activity modulation, expression modulation or both.

Biosensors for detecting modulator activity detection are also a feature of the invention. These include devices or systems that comprise a gene or gene product corresponding to a loci of FIGS. 1 and/or 2 coupled to a readout that measures or displays one or more activity of the gene or product. Thus, any of the above described assay components can be configured as a biosensor by operably coupling the appropriate assay components to a readout. The readout can be optical (e.g., to detect cell markers or cell survival) electrical (e.g., coupled to a FET, a BIAcore, or any of a variety of others), spectrographic, or the like, and can optionally include a user-viewable display (e.g., a CRT or optical viewing station). The biosensor can be coupled to robotics or other automation, e.g., microfluidic systems, that direct contact of the putative modulators to the proteins of the invention, e.g., for automated high-throughput analysis of putative modulator activity. A large variety of automated systems that can be adapted to use with the biosensors of the invention are commercially available. For example, automated systems have been made to assess a variety of biological phenomena, including, e.g., expression levels of genes in response to selected stimuli (Service (1998) "Microchips Arrays Put DNA on the Spot" Science 282: 396-399). Laboratory systems can also perform, e.g., repetitive fluid handling operations (e.g., pipetting) for transferring material to or from reagent storage systems that comprise arrays, such as microtiter trays or other chip trays, which are used as basic container elements for a variety of automated laboratory methods. Similarly, the systems manipulate, e.g., microtiter trays and control a variety of environmental conditions such as temperature, exposure to light or air, and the like. Many such automated systems are commercially available and are described herein, including those described above. These include various Zymate systems, ORCA® robots, microfluidic devices, etc. For example, the LabMicrofluidic Device® high throughput screening system (HTS) by Caliper Technologies, Mountain View, Calif. can be adapted for use in the present invention to screen for modulator activity.

In general, methods and sensors for detecting protein expression level and activity are available, including those taught in the various references above, including R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach*

IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and Satinder Ahuja ed., *Handbook of Bioseparations*, Academic Press (2000). "Proteomic" detection methods, which detect many proteins simultaneously have been described and are also noted above, including various multidimensional electrophoresis methods (e.g., 2-d gel electrophoresis), mass spectrometry based methods (e.g., SELDI, MALDI, electrospray, etc.), or surface plasmon reasonance methods. These can also be used to track protein activity and/or expression level.

Similarly, nucleic acid expression levels (e.g., mRNA) can be detected using any available method, including northern analysis, quantitative RT-PCR, or the like. References sufficient to guide one of skill through these methods are readily available, including Ausubel, Sambrook and Berger.

Potential modulator libraries to be screened for effects on expression and/or activity are available. These libraries can be random, or can be targeted.

Targeted libraries include those designed using any form of a rational design technique that selects scaffolds or building blocks to generate combinatorial libraries. These techniques include a number of methods for the design and combinatorial synthesis of target-focused libraries, including morphing with bioisosteric transformations, analysis of target-specific privileged structures, and the like. In general, where information regarding structure genes or gene products of FIGS. 1 and/or 2, is available, likely binding partners can be designed, e.g., using flexible docking approaches, or the like. Similarly, random libraries exist for a variety of basic chemical scaffolds. In either case, many thousands of scaffolds and building blocks for chemical libraries are available, including those with polypeptide, nucleic acid, carbohydrate, and other backbones. Commercially available libraries and library design services include those offered by Chemical Diversity (San Diego, Calif.), Affymetrix (Santa Clara, Calif.), Sigma (St. Louis Mo.), ChemBridge Research Laboratories (San Diego, Calif.), TimTec (Newark, Del.), Nuevolution A/S (Copenhagen, Denmark) and many others.

Kits for treatment of breast cancer phenotypes can include a modulator identified as noted above and instructions for administering the compound to a patient to treat breast cancer.

Regulating Gene Expression of Genes

Gene expression (e.g., transcription and/or translation) of any gene linked to a polymorphism in FIGS. 1 and 2 can be regulated using any of a variety of techniques known in the art. For example, gene expression can be inhibited using an antisense nucleic acid or an interfering RNA. Inhibition of expression in particular cell-types can be used for further studying the in vitro or in vivo role of these genes, and/or as a mechanism for treating a condition caused by overexpression of a linked gene, and/or for treating a dominant effect caused by a particular allele of such a gene. Gene expression modulators are one class of modulators provided by the present invention, e.g., modulators applied to modulate a breast cancer phenotype.

For example, use of antisense nucleic acids is well known in the art. An antisense nucleic acid has a region of complementarity to a target nucleic acid, e.g., a target gene, mRNA, or cDNA. Typically, a nucleic acid comprising a nucleotide sequence in a complementary, antisense orientation with respect to a coding (sense) sequence of an endogenous gene is introduced into a cell. The antisense nucleic acid can be RNA, DNA, a PNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced, e.g., for any gene whose coding sequence is known or can be determined by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. No. 6,242,258 to Haselton and Alexander (Jun. 5, 2001) entitled "Methods for the selective regulation of DNA and RNA transcription and translation by photoactivation"; U.S. Pat. Nos. 6,500,615; 6,498,035; 6,395,544; 5,563,050; E. Schuch et al (1991) Symp Soc. Exp Biol 45:117-127; de Lange et al., (1995) *Curr Top Microbiol Immunol* 197:57-75; Hamilton et al. (1995) *Curr Top Microbiol Immunol* 197:77-89; Finnegan et al., (1996) *Proc Natl Acad Sci USA* 93:8449-8454; Uhlmann and A. Pepan (1990), *Chem. Rev.* 90:543; P. D. Cook (1991), Anti-Cancer Drug Design 6: 5 85; J. Goodchild, Bioconjugate Chem. 1 (1990) 165; and, S. L. Beaucage and R. P. Iyer (1993), *Tetrahedron* 49:6123; and F. Eckstein, Ed. (1991), *Oligonucleotides and Analogues—A Practical Approach*, IRL Press.

Gene expression can also be inhibited by RNA silencing or interference. "RNA silencing" refers to any mechanism through which the presence of a single-stranded or, typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g., histone acetylation and heterochromatin formation leading to inhibition of transcription of the target mRNA).

The term "RNA interference" ("RNAi," sometimes called RNA-mediated interference, post-transcriptional gene silencing, or quelling) refers to a phenomenon in which the presence of RNA, typically double-stranded RNA, in a cell results in inhibition of expression of a gene comprising a sequence identical, or nearly identical, to that of the double-stranded RNA. The double-stranded RNA responsible for inducing RNAi is called an "interfering RNA." Expression of the gene is inhibited by the mechanism of RNAi as described below, in which the presence of the interfering RNA results in degradation of mRNA transcribed from the gene and thus in decreased levels of the mRNA and any encoded protein.

The mechanism of RNAi has been and is being extensively investigated in a number of eukaryotic organisms and cell types. See, for example, the following reviews: McManus and Sharp (2002) "Gene silencing in mammals by small interfering RNAs" Nature Reviews Genetics 3:737-747; Hutvagner and Zamore (2002) "RNAi: Nature abhors a double strand" Curr Opin Genet & Dev 200:225-232; Hannon (2002) "RNA interference" Nature 418:244-251; Agami (2002) "RNAi and related mechanisms and their potential use for therapy" Curr Opin Chem Biol 6:829-834; Tuschl and Borkhardt (2002) "Small interfering RNAs: A revolutionary tool for the analysis of gene function and gene therapy" Molecular Interventions 2:158-167; Nishikura (2001) "A short primer on RNAi: RNAdirected RNA polymerase acts as a key catalyst" Cell 107:415-418; and Zamore (2001) "RNA interference: Listening to the sound of silence" Nature Structural Biology 8:746-750. RNAi is also described in the patent literature; see, e.g., CA 2359180 by Kreutzer and Limmer entitled "Method and medicament for inhibiting the expression of a given gene"; WO 01/68836 by Beach et al. entitled "Methods and compositions for RNA interference"; WO 01/70949 by Graham et al. entitled "Genetic silencing"; and WO 01/75164 by Tuschl et al. entitled "RNA sequence-specific mediators of RNA interference."

In brief, double-stranded RNA introduced into a cell (e.g., into the cytoplasm) is processed, for example by an RNAse III-like enzyme called Dicer, into shorter double-stranded fragments called small interfering RNAs (siRNAs, also called short interfering RNAs). The length and nature of the siRNAs produced is dependent on the species of the cell, although typically siRNAs are 21-25 nucleotides long (e.g., an siRNA may have a 19 base pair duplex portion with two nucleotide 3' overhangs at each end). Similar siRNAs can be produced in vitro (e.g., by chemical synthesis or in vitro transcription) and introduced into the cell to induce RNAi. The siRNA becomes associated with an RNA-induced silencing complex (RISC). Separation of the sense and antisense strands of the siRNA, and interaction of the siRNA antisense strand with its target mRNA through complementary base-pairing interactions, optionally occurs. Finally, the mRNA is cleaved and degraded.

Expression of a target gene in a cell can thus be specifically inhibited by introducing an appropriately chosen double-stranded RNA into the cell. Guidelines for design of suitable interfering RNAs are known to those of skill in the art. For example, interfering RNAs are typically designed against exon sequences, rather than intrans or untranslated regions. Characteristics of high efficiency interfering RNAs may vary by cell type. For example, although siRNAs may require 3' overhangs and 5' phosphates for most efficient induction of RNAi in *Drosophila* cells, in mammalian cells blunt ended siRNAs and/or RNAs lacking 5' phosphates can induce RNAi as effectively as siRNAs with 3' overhangs and/or 5' phosphates (see, e.g., Czauderna et al. (2003) "Structural variations and stabilizing modifications of synthetic siRNAs in mammalian cells" Nucl Acids Res 31:2705-2716). As another example, since double-stranded RNAs greater than 30-80 base pairs long activate the antiviral interferon response in mammalian cells and result in nonspecific silencing, interfering RNAs for use in mammalian cells are typically less than 30 base pairs (for example, Caplen et al. (2001) "Specific inhibition of gene expression by small double-stranded RNAs in invertebrate and vertebrate systems" Proc. Natl. Acad. Sci. USA 98:9742-9747, Elbashir et al. (2001) "Duplexes of 21-nucleotide RNAs mediate RNA interference in cultured mammalian cells" Nature 411:494-498 and Elbashir et al. (2002) "Analysis of gene function in somatic mammalian cells using small interfering RNAs" Methods 26: 199-213 describe the use of 21 nucleotide siRNAs to specifically inhibit gene expression in mammalian cell lines, and Kim et al. (2005) "Synthetic dsRNA Dicer substrates enhance RNAi potency and efficacy" Nature Biotechnology 23:222-226 describes use of 25-30 nucleotide duplexes). The sense and antisense strands of a siRNA are typically, but not necessarily, completely complementary to each other over the double-stranded region of the siRNA (excluding any overhangs). The antisense strand is typically completely complementary to the target mRNA over the same region, although some nucleotide substitutions can be tolerated (e.g., a one or two nucleotide mismatch between the antisense strand and the mRNA can still result in RNAi, although at reduced efficiency). The ends of the double-stranded region are typically more tolerant to substitution than the middle; for example, as little as 15 bp (base pairs) of complementarity between the antisense strand and the target mRNA in the context of a 21 mer with a 19 bp doublestranded region has been shown to result in a functional siRNA (see, e.g., Czaudema et al. (2003) "Structural variations and stabilizing modifications of synthetic siRNAs in mammalian cells" Nucl Acids Res 31:2705-2716). Any overhangs can but need not be complementary to the target mRNA; for example, TT (two 2'-deoxythymidines) overhangs are frequently used to reduce synthesis costs.

Although double-stranded RNAs (e.g., double-stranded siRNAs) were initially thought to be required to initiate RNAi, several recent reports indicate that the antisense strand of such siRNAs is sufficient to initiate RNAi. Single-stranded antisense siRNAs can initiate RNAi through the same pathway as double-stranded siRNAs (as evidenced, for example, by the appearance of specific mRNA endonucleolytic cleavage fragments). As for double-stranded interfering RNAs, characteristics of high-efficiency single-stranded siRNAs may vary by cell type (e.g., a 5' phosphate may be required on the antisense strand for efficient induction of RNAi in some cell types, while a free 5' hydroxyl is sufficient in other cell types capable of phosphorylating the hydroxyl). See, e.g., Martinez et al. (2002) "Single-stranded antisense siRNAs guide target RNA cleavage in RNAi" Cell 110:563-574; Amarzguioui et al. (2003) "Tolerance for mutations and chemical modifications in a siRNA" Nucl. Acids Res. 31:589-595; Holen et al. (2003) "Similar behavior of single-strand and double-strand siRNAs suggests that they act through a common RNAi pathway" Nucl. Acids Res. 31:2401-2407; and Schwarz et al. (2002) Mol. Cell 10:537-548.

Due to differences in efficiency between siRNAs corresponding to different regions of a given target mRNA, several siRNAs are typically designed and tested against the target mRNA to determine which siRNA is most effective. Interfering RNAs can also be produced as small hairpin RNAs (shRNAs, also called short hairpin RNAs), which are processed in the cell into siRNA-like molecules that initiate RNAi (see, e.g., Siolas et al. (2005) "Synthetic shRNAs as potent RNAi triggers" Nature Biotechnology 23:227-231).

The presence of RNA, particularly double-stranded RNA, in a cell can result in inhibition of expression of a gene comprising a sequence identical or nearly identical to that of the RNA through mechanisms other than RNAi. For example, double-stranded RNAs that are partially complementary to a target mRNA can repress translation of the mRNA without affecting its stability. As another example, double-stranded RNAs can induce histone methylation and heterochromatin formation, leading to transcriptional silencing of a gene comprising a sequence identical or nearly identical to that of the RNA (see, e.g., Schramke and Allshire (2003) "Hairpin RNAs and retrotransposon LTRs effect RNAi and chromatin-based gene silencing" Science 301: 1069-1074; Kawasaki and Taira (2004) "Induction of DNA methylation and gene silencing by short interfering RNAs in human cells" Nature 431:211-217; and Morris et al. (2004)

"Small interfering RNA-induced transcriptional gene silencing in human cells" Science 305: 1289-1292).

Short RNAs called microRNAs (miRNAs) have been identified in a variety of species. Typically, these endogenous RNAs are each transcribed as a long RNA and then processed to a pre-miRNA of approximately 60-75 nucleotides that forms an imperfect hairpin (stem-loop) structure. The pre-miRNA is typically then cleaved, e.g., by Dicer, to form the mature miRNA. Mature miRNAs are typically approximately 21-25 nucleotides in length, but can vary, e.g., from about 14 to about 25 or more nucleotides. Some, though not all, miRNAs have been shown to inhibit translation of mRNAs bearing partially complementary sequences. Such miRNAs contain one or more internal mismatches to the corresponding mRNA that are predicted to result in a bulge in the center of the duplex formed by the binding of the miRNA antisense strand to the mRNA. The miRNA typically forms approximately 14-17 Watson-Crick base pairs with the mRNA; additional wobble base pairs can also be formed. In addition, short synthetic double-stranded RNAs (e.g., similar to siRNAs) containing central mismatches to the corresponding mRNA have been shown to repress translation (but not initiate degradation) of the mRNA. See, for example, Zeng et al. (2003) "MicroRNAs and small interfering RNAs can inhibit mRNA expression by similar mechanisms" Proc. Natl. Acad. Sci. USA 100: 9779-9784; Doench et al. (2003) "siRNAs can function as miRNAs" Genes & Dev. 17:438-442; Bartel and Bartel (2003) "MicroRNAs: At the root of plant development?" Plant Physiology 132:709-717; Schwarz and Zamore (2002) "Why do miRNAs live in the miRNP?" Genes & Dev. 16: 1025-1031; Tang et al. (2003) "A biochemical framework for RNA silencing in plants" Genes & Dev. 17:49-63; Meister et al. (2004) "Sequence-specific inhibition of microRNA- and siRNA-induced RNA silencing" RNA 10:544-550; Nelson et al. (2003) "The microRNA world: Small is mighty" Trends Biochem. Sci. 28:534-540; Scacheri et al. (2004) "Short interfering RNAs can induce unexpected and divergent changes in the levels of untargeted proteins in mammalian cells" Proc. Natl. Acad. Sci. USA 101:1892-1897; Sempere et al. (2004) "Expression profiling of mammalian micro RNAs uncovers a subset of brain expressed microRNAs with possible roles in murine and human neuronal differentiation" Genome Biology 5:R13; Dykxhoom et al. (2003) "Killing the messenger: Short RNAs that silence gene expression" Nature Reviews Molec. and Cell Biol. 4:457-467; McManus (2003) "MicroRNAs and cancer" Semin Cancer Biol. 13:253-288; and Stark et al. (2003) "Identification of *Drosophila* microRNA targets" PLoS Biol. 1:E60.

The cellular machinery involved in translational repression of mRNAs by partially complementary RNAs (e.g., certain miRNAs) appears to partially overlap that involved in RNAi, although, as noted, translation of the mRNAs, not their stability, is affected and the mRNAs are typically not degraded.

The location and/or size of the bulge(s) formed when the antisense strand of the RNA binds the mRNA can affect the ability of the RNA to repress translation of the mRNA. Similarly, location and/or size of any bulges within the RNA itself can also affect efficiency of translational repression. See, e.g., the references above. Typically, translational repression is most effective when the antisense strand of the RNA is complementary to the 3' untranslated region (3' UTR) of the mRNA. Multiple repeats, e.g., tandem repeats, of the sequence complementary to the antisense strand of the RNA can also provide more effective translational repression; for example, some mRNAs that are translationally repressed by endogenous miRNAs contain 7-8 repeats of the miRNA binding sequence at their 3' UTRs. It is wolih noting that translational repression appears to be more dependent on concentration of the RNA than RNA interference does; translational repression is thought to involve binding of a single mRNA by each repressing RNA, while RNAi is thought to involve cleavage of multiple copies of the mRNA by a single siRNA-RISC complex.

Guidance for design of a suitable RNA to repress translation of a given target mRNA can be found in the literature (e.g., the references above and Doench and Sharp (2004) "Specificity of microRNA target selection in translational repression" Genes & Dev. 18:504-511; Rehmsmeier et al. (2004) "Fast and effective prediction of microRNA/target duplexes" RNA 10:1507-1517; Robins et al. (2005) "Incorporating structure to predict micro RNA targets" Proc Natl Acad Sci 102:4006-4009; and Mattick and Makunin (2005) "Small regulatory RNAs in mammals" Hum. Mol. Genet. 14:R121—15 R132, among many others) and herein. However, due to differences in efficiency of translational repression between RNAs of different structure (e.g., bulge size, sequence, and/or location) and RNAs corresponding to different regions of the target mRNA, several RNAs are optionally designed and tested against the target mRNA to determine which is most effective at repressing translation of the target mRNA.

Antibodies to Gene Products

An additional class of modulators are antibodies that bind to products of genes linked to the loci herein. The antibodies can be utilized for detecting and/or purifying the gene products e.g., in situ, to monitor the gene product. Antibodies can also be used to block function of gene products, in vivo, in situ or in vitro. As used herein, the term "antibody" includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a relevant gene product, any of a variety of host animals may be immunized by injection with the polypeptide, or a portion thereof. Such host animals may include, but are not limited to, rabbits, mice and rats, to name but a few. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacille Calmette-Guerin*) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., 20 *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies maybe of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

In addition, techniques developed for the production of "chimeric multibodies" (Morrison et al., *Proc. Nat'l. Acad. Sci. USA* 81:6851-6855, 1984; Neuberger et al., *Nature* 312:604-608, 1984; Takeda et al., *Nature* 314:452-454, 1985) by splicing the genes from a mouse antibody molecule of appropriate antigen specificity, together with genes from a human antibody molecule of appropriate biological activity, can be used. A chimeric antibody is a molecule in which different portions are derived from different animal species, such as those having a variable or hypervariable region derived from a murine mAb and a human immunoglobulin constant region. Similarly, humanized antibodies can also be produced using available techniques.

Alternatively, techniques described for the production of single-chain antibodies (U.S. Pat. No. 4,946,778; Bird, *Science* 242:423-426, 1988; Huston et al., *Proc. Nat'l. Acad. Sci. USA* 85:5879-5883, 1988; and Ward et al., *Nature* 334:544-546, 10 1989) can be adapted to produce differentially expressed gene-single chain antibodies. Single chain antibodies are fanned by linking the heavy and light chain fragments of the Fv region via an amino acid bridge, resulting in a single-chain polypeptide.

In one aspect, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments which recognize specific epitopes may be generated by known techniques. For example, such fragments include, but are not limited to, the F(ab')$_2$ fragments, which can be produced by pepsin digestion of the antibody molecule, and the Fab fragments, which can be generated by reducing the disulfide bridges of the F(ab')$_2$ fragments. Alternatively, Fab expression libraries may be constructed (Huse et al., Science 246:1275-1281, 1989) to allow rapid and easy identification of monoclonal Fab fragments with the desired specificity.

The protocols for detecting and measuring the expression of the gene products, using the above mentioned antibodies, are well known in the art. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific and patent literature, and many employed commercially.

One method, for ease of detection, is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule and incubated for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay, in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the protein expressed by the gene of interest.

The most commonly used reporter molecules in this type of assay are either enzymes, fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product, rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of PLAB which is present in the serum sample.

Alternately, fluorescent compounds, such as fluorescein and rhodamine, can be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Cell Rescue and Therapeutic Administration

In one aspect, the invention includes rescue of a cell that is defective in function of one or more endogenous genes or polypeptides of FIGS. 1 and/or 2 (thus conferring the relevant phenotype of interest, e.g., breast cancer susceptibility, resistance, etc.). This can be accomplished simply by introducing a new copy of the gene (or a heterologous nucleic acid that expresses the relevant protein), i.e., a gene having an allele that is desired, into the cell. Other approaches, such as homologous recombination to repair the defective gene (e.g., via chimeraplasty) can also be performed. In any event, rescue of function can be measured, e.g., in any of the assays noted herein. Indeed, this method can be used as a general method of screening cells in vitro for expression or activity of any gene or gene product of FIGS. 1 and/or 2. Accordingly, in vitro rescue of function is useful in this context for the myriad in vitro screening methods noted above. The cells that are rescued can include cells in culture, (including primary or secondary cell culture from patients, as well as cultures of well-established cells). Where the cells are isolated from a patient, this has additional diagnostic utility in establishing which gene or product is defective in a patient that presents with a relevant phenotype.

In another aspect, the cell rescue occurs in a patient, e.g., a human, e.g., to remedy a defect. Thus, one aspect of the invention is gene therapy to remedy defects. In these applications, the nucleic acids of the invention are optionally cloned into appropriate gene therapy vectors (and/or are simply delivered as naked or liposome-conjugated nucleic acids), which are then delivered, optionally in combination with appropriate carriers or delivery agents. Proteins can also be delivered directly, but delivery of the nucleic acid is typically preferred in applications where stable expression is desired. Similarly, modulators of any defect identified by the methods herein can be used therapeutically.

Compositions for administration, e.g., comprise a therapeutically effective amount of the modulator, gene therapy vector or other relevant nucleic acid, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering gene therapy vectors for topical use are well known in the art and can be applied to administration of the nucleic acids of the invention.

Therapeutic compositions comprising one or more modulator or gene therapy nucleic acid of the invention are optionally tested in one or more appropriate in vitro and/or in vivo animal model of disease, to confirm efficacy, tissue metabolism, and to estimate dosages, according to methods well known in the art. In particular, dosages can initially be determined by activity, stability or other suitable measures of the formulation.

Administration is by any of the routes normally used for introducing a molecule into ultimate contact with cells. Modulators and/or nucleic acids that encode a relevant sequence can be administered in any suitable manner, optionally with one or more pharmaceutically acceptable carriers. Suitable methods of administering such nucleic acids in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Compositions can be administered by a number of routes including, but not limited to: oral, intravenous, intraperitoneal, intramuscular, transdermal, subcutaneous, topical, sublingual, or rectal administration. Compositions can be administered via liposomes (e.g., topically), or via topical delivery of naked DNA or viral vectors. Such administration routes and appropriate formulations are generally known to those of skill in the art.

The compositions, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

The dose administered to a patient, in the context of the present invention, is sufficient to effect a beneficial therapeutic response in the patient over time. The dose is determined by the efficacy of the particular vector, or other formulation, and the activity, stability or serum half-life of the polypeptide which is expressed, and the condition of the patient, as well as the body weight or surface area of the patient to be treated. The size of the dose is also determined by the existence, nature, and extent of any adverse side-effects that accompany the administration of a particular vector, formulation, or the like in a particular patient. In determining the effective amount of the vector or formulation to be administered in the treatment of disease, the physician evaluates local expression, or circulating plasma levels, formulation toxicities, progression of the relevant disease, and/or where relevant, the production of antibodies to proteins encoded by the polynucleotides. The dose administered, e.g., to a 70 kilogram patient are typically in the range equivalent to dosages of currently-used therapeutic proteins, adjusted for the altered activity or serum half-life of the relevant composition. The vectors of this invention can supplement treatment conditions by any known conventional therapy.

For administration, formulations of the present invention are administered at a rate determined by the LD-50 of the relevant formulation, and/or observation of any side effects of the vectors of the invention at various concentrations, e.g., as applied to the mass or topical delivery area and overall health of the patient. Administration can be accomplished via single or divided doses.

If a patient undergoing treatment develops fevers, chills, or muscle aches, he/she receives the appropriate dose of aspirin, ibuprofen, acetaminophen or other pain/fever controlling drug. Patients who experience reactions to the compositions, such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

Diagnostic and Prognostic Assays

The nucleic acids, polypeptides, antibodies and other compositions herein may be utilized as reagents (e.g., in pre-packaged kits) for prognosis and diagnosis of susceptibility or resistance to breast cancer phenotypes. The methods can be practiced on subjects known to have one or more symptoms of a breast cancer phenotype as part of a differential diagnosis or prognosis of other diseases. The methods can also be practiced on subjects having a known susceptibility to a breast cancer phenotype. The polymorphic profile of such an individual can increase or decrease the assessment of susceptibility. For example, an individual having two siblings with breast cancer is known to be at increased susceptibility to the disease compared with the general population. A finding of additional factors favoring susceptibility increases the risk whereas finding factors favoring resistance decreases the risk.

The invention provides methods of determining the polymorphic profile of an individual at one or more of SNPs of the invention. The SNPs includes those shown in FIGS. 1 and 2. and those in linkage disequilibrium with them. Those in linkage disequilibrium with them usually occur in the same genes or within 100 or 50 or 20 kb of the same genes. SNPs in linkage disequilibrium with the SNPs in the Figures herein can be determined by haplotype mapping. Haplotypes can be determined by fusing diploid cells from different species. The resulting cells are partially haploid, allowing determination of haplotypes on haploid chromosomes (see, e.g., US 20030099964). Alternatively, SNPs in linkage disequilibrium with exemplified SNPs can be determined by similar association studies to those described in the examples below.

The polymorphic profile constitutes the polymorphic forms occupying the various polymorphic sites in an individual. In a diploid genome, two polymorphic forms, the same or different from each other, usually occupy each polymorphic site. Thus, the polymorphic profile at sites X and Y can be represented in the form X(x1, x1), and Y (y1, y2), wherein x1, x1 represents two copies of allele x1 occupying site X and y1, y2 represent heterozygous alleles occupying site Y.

The polymorphic profile of an individual can be scored by comparison with the polymorphic forms associated with resistance or susceptibility to breast cancer phenotypes occurring at each site as shown in the Figures herein. The comparison can be performed on at least, e.g., 1, 2, 5, 10, 25, 50, or all of the polymorphic sites, and optionally, others in linkage disequilibrium with them. The polymorphic sites can be analyzed in combination with other polymorphic sites. However, the total number of polymorphic sites analyzed is usually fewer than 10,000, 1000, 100, 50 or 25 and can be about 10 or less, about 5 or less, or about 2 or less.

The number of resistance or susceptibility alleles present in a particular individual can be combined additively or as ratio to provide an overall score for the individual's genetic propensity to breast cancer phenotypes (see U.S. Ser. No. 60/566,302, filed Apr. 28, 2004, U.S. Ser. No. 60/590,534, filed Jul. 22, 2004, U.S. Ser. No. 10/956,224 filed Sep. 30, 2004, and PCT US05/07375 filed Mar. 3, 2005). Resistance alleles can be arbitrarily each scored as +1 and susceptibility alleles as −1 (or vice versa). For example, if an individual is typed at 100 polymorphic sites of the invention and is homozygous for resistance at all of them, he could be assigned a score of 100% genetic propensity to resistance to breast cancer phenotypes or 0% propensity to susceptibility to breast cancer phenotypes. The reverse applies if the individual is homozygous for all susceptibility alleles. More typically, an individual is homozygous for resistance alleles at some loci, homozygous for susceptibility alleles at some loci, and heterozygous for resistance/susceptibility alleles at other loci. Such an individual's genetic propensity for breast cancer phenotypes can be scored by assigning all resistance alleles a score of +1, and all susceptibility alleles a score of −1 (or vice versa) and combining the scores. For example, if an individual has 102 resistance alleles and 204 susceptibility alleles, the individual can be scored as having a 33% genetic propensity to resistance and 67% genetic propensity to susceptibility. Alternatively, homozygous resistance alleles can be assigned a score of +1, heterozygous alleles a score of zero and homozygous susceptibility alleles a score of −1. The relative numbers of resistance alleles and susceptibility alleles can also be expressed as a percentage. Thus, an individual who is homozygous for resistance alleles at 30 polymorphic sites, homozygous for susceptibility alleles at 60 polymorphic sites, and heterozygous at the remaining 63 sites is assigned a genetic propensity of 33% for resistance. As a further alternative, homozygosity for susceptibility can be scored as +2, heterozygosity, as +1 and homozygosity for resistance as 0.

The individual's score, and the nature of the polymorphic profile are useful in prognosis or diagnosis of an individual's susceptibility to breast cancer phenotypes. Optionally, a patient can be informed of susceptibility to a breast cancer phenotype indicated by the genetic profile. Presence of a high genetic propensity to breast cancer phenotypes can be treated as a warning to commence prophylactic or therapeutic treatment. For example, individuals with elevated risk of developing a breast cancer phenotype may be monitored differently (e.g., more frequent mammography) or may be treated prophylactically (e.g., with one or more drugs). Presence of a high propensity to a breast cancer phenotype also indicates the utility of performing secondary testing, such as a biopsy.

Polymorphic profiling is useful, for example, in selecting agents to effect treatment or prophylaxis of breast cancer phenotypes in a given individual. Individuals having similar polymorphic profiles are likely to respond to agents in a similar way.

Polymorphic profiling is also useful for stratifying individuals in clinical trials of agents being tested for capacity to treat breast cancer phenotypes or related conditions. Such trials are performed on treated, or control populations having similar or identical polymorphic profiles (see EP99965095.5), for example, a polymorphic profile indicating an individual has an increased risk of developing a breast cancer phenotype. Use of genetically matched populations eliminates or reduces variation in treatment outcome due to genetic factors, leading to a more accurate assessment of the efficacy of a potential drug. Computer-implemented algorithms can be used to identify more genetically homogenous subpopulations in which treatment or prophylaxis has a significant effect notwithstanding that the treatment or prophylaxis is ineffective in more heterogeneous larger populations. In such methods, data are provided for a first population with a breast cancer phenotype treated with an agent, and a second population also with the breast cancer phenotype but treated with a placebo. The polymorphic profile of individuals in the two populations is determined in at least one polymorphic site in or within 100 kb or 50 kb or 20 kb of a gene selected from those shown in FIGS. 1 and/or 2. Data are also provided as to whether each patient in the populations reaches a desired endpoint indicative of successful treatment or prophylaxis. Subpopulations of each of the first and second populations are then selected such that the individuals in the subpopulations have greater similarity of polymorphic profiles with each other than do the individuals in the original first and second populations. There are many criteria by which similarity can be assessed. For example, one criterion is to require that individuals in the subpopulations have at least one susceptibility allele at each of at least ten of the above genes. Another criterion is that individuals in the subpopulations have at least 75% susceptibility alleles for each of the polymorphic sites at which the polymorphic profile is determined. Regardless of the criteria used to assess similarity, the endpoint data of the subpopulations are compared to determine whether treatment or prophylaxis has achieved a statistically significant result in the subpopulations. As a result of computer implementation, billions of criteria for similarity can be analyzed to identify one or a few subpopulations showing statistical significance.

Polymorphic profiling is also useful for excluding individuals with no predisposition to breast cancer phenotypes from clinical trials. Including such individuals in the trial increases the size of the population needed to achieve a statistically significant result. Individuals with no predisposition to breast cancer phenotypes can be identified by determining the numbers of resistances and susceptibility alleles in a polymorphic profile as described above. For example, if a subject is genotyped at ten sites in ten genes of the invention associated with breast cancer phenotypes, twenty alleles are determined in total. If over 50% and preferably over 60% or 75% percent of these are resistance genes, the individual is unlikely to develop a breast cancer phenotype and can be excluded from the trial.

In other embodiments, stratifying individuals in clinical trials may be accomplished using polymorphic profiling in combination with other stratification methods, including, but not limited to, family history, risk models (e.g., Gail Score, Claus model), clinical phenotypes (e.g., atypical lesions and breast density), and specific candidate biomarkers (e.g., IGF1, IFG2, IGFBP3, Ki-67, and estradiol). For example, stratification of higher risk in chemoprevention trials that includes stratification based on polymorphic profiles can improve outcomes. In particular, markers linked to FGFR2 can be used to stratify anti-VEGF or anti-angiogenesis therapy response, and markers linked to PKHD1 can be used to stratify anti-EGF therapy efficacy (anti-EGF therapies are active in patients with polycystic kidney and hepatic disease).

Polymorphic profiles can also be used after the completion of a clinical trial to elucidated differences in response to a given treatment. For example, the set of polymorphisms can be used to stratify the enrolled patients into disease sub-types or classes. It is also possible to use the polymorphisms to identify subsets of patients with similar polymorphic profiles who have unusual (high or low) response to treatment or who do not respond at all (non-responders). In this way, information about the underlying genetic factors influencing response to treatment can be used in many aspects of the development of treatment (these range from the identification of new targets, through the design of new trials to product labeling and patient targeting). Additionally, the polymorphisms can be used to identify the genetic factors involved in adverse response to treatment (adverse events). For example, patients who show adverse response may have more similar polymorphic profiles than would be expected by chance. This allows the early identification and exclusion of such individuals from treatment. It also provides information that can be used to understand the biological causes of adverse events and to modify the treatment to avoid such outcomes.

Polymorphic profiles can also be used for other purposes, including paternity testing and forensic analysis as described by U.S. Pat. No. 6,525,185. In forensic analysis, the polymorphic profile from a sample at the scene of a crime is compared with that of a suspect. A match between the two is evidence that the suspect in fact committed the crime, whereas lack of a match excludes the suspect. The present polymorphic sites can be used in such methods, as can other polymorphic sites in the human genome.

EXAMPLES

The following examples are offered to illustrate, but not to limit the claimed invention. One of skill will recognize a variety of non-critical parameters that can be altered within the scope of the invention.

Example 1: Strategies for Identification of Breast Cancer Markers

Introduction: Identifying Common Genetic Variants

There are important applications to public health in the identification of breast cancer marker alleles. Where genetic variation is due to many loci, risks to individuals vary widely, depending upon the number of high-risk alleles inherited at susceptibility loci. Our analyses based on the model of Antoniou et al[13] suggest that there may be as much as 40-fold difference in risk between the top and bottom 20% of the 10 population. Under the same model, half of all breast cancers occur in the 12% of women at greatest risk, and these women have risks of at least 1 in 8 by age 70. By contrast, the 50% of women at least risk have only 12% of the cancers, and individual risks of less than 1 in 30[14]. Genes that are identified as being correlated to breast cancer risk can be used for estimation of associated and individual risks. The practical consequences of this risk estimation are substantial.

Common genetic variants that confer modest degrees of risk have individually important effects at the population level. For example, a common variant, with frequency 20%, which increases individual risk by only 1.5-fold would account for 15% of the population burden of a cancer. The analogy is with moderate elevations of blood pressure, or of cholesterol, in cardiovascular disease. If the variant indicates a feasible mechanism for intervention, this also provides novel possibilities for targeted prevention.

In addition to these practical outcomes, the identification of cancer susceptibility genes helps to clarify mechanisms of carcinogenesis (as has already happened, for example, with BRCA1 and BRCA2). Extending beyond known candidates to a whole genome search has the great advantage that totally novel mechanisms emerge. These mechanisms also provide new therapeutic targets.

Finally, knowledge of susceptibility genes allows us to clarify the effects of lifestyle risk factors by studying the effects of genes and these risk factors in combination, using for example the EPIC cohort.

Breast Cancer

Although arguments may be made for association studies in many cancers, there are several reasons why it is particularly appropriate to can-y out a study in breast cancer. It is the commonest cancer in women, and its aetiology is still poorly understood. The genetic basis for the disease has been more thoroughly investigated than for any other common cancer. As a result, the evidence in favor of a polygenic basis is clearer than for other cancers. Long-term studies have assembled sufficiently large series of cases to identify susceptibility loci reliably. In addition, cases with a strong family history are available through cancer genetics clinics and can provide substantial gains in efficiency in the association study (see 'Research Proposal'). Finally, there are interventions that can be offered to women found to be at increased risk. For example, prophylactic oophorectomy can reduce substantially the subsequent risk of breast cancer[15]. Recent studies suggest that screening by MRI may provide much greater sensitivity than mammography but at significantly greater cost[16].

Study Design

Genotypes for 200,000 single nucleotide polymorphisms (SNPs) are determined in a set of 400 familial breast cancer cases and 400 controls from the EPIC cohort; 5% of these SNPs showing the strongest association are analyzed in further population-based series of 4,600 cases and 4,600 controls. Positive associations at this stage are confirmed in further large case-control series.

In addition to the breast cancer endpoint, many quantitative phenotypes are available in the control set and provide additional data for genetic analysis. These include phenotypes (e.g. mammographic patterns, hormone levels) that are related to cancer risk.

Yield

The scan evaluates single nucleotide polymorphisms of frequency 10% or greater (and some in the 5-10% range) across the entire genome outside repetitive sequences. It has approximately 80% power to detect any common variant within these regions that accounts for 2% or more of the overall inherited component of breast cancer.

The Design of Studies to Search for Common Susceptibility Variants

An efficient design to identify common low risk alleles is a case/control study. Variants that are associated with susceptibility are identified by their occurrence at a significantly higher frequency in cancer cases than in controls matched for genetic background. In this study, the variants are single nucleotide polymorphisms (SNPs). Most often, the active or functional variant that might be relevant to disease susceptibility is not known, and so the search relies on a set of 'tagging' SNPs that can report on the presumed (but unknown) active variants.

The case-control association study approach has already been used extensively in breast cancer on a "candidate gene" basis. Polymorphisms in the coding region and intrans of close to 100 genes have previously been studied in this way. These include, for example, genes involved in sex-steroid hormone metabolism, cell-cycle control and DNA repair. Although some associations have been suggested for common variants, none has been definitively established. The results to date suggest that the majority of the variation in breast cancer risk is not due to variants in the intragenic DNA of the genes that would be a first choice as breast cancer candidates. There are, moreover, serious limitations to a candidate gene approach. It is slow and relatively expensive, being dependent on developing assays on a SNP by SNP basis for each gene to be tested; it is incomplete in its coverage even of the candidate genes, in particular ignoring, in most cases, potential regulatory variation; and it is restricted by current knowledge of the biology of the disease. A genome-wide search, by contrast, has the potential to identify active common variants without any prior knowledge of function or location.

Genome Scanning SNPs

A requirement for a genome scan is to define a set of SNPs that provides the best compromise between completeness and cost in reporting on the set of all other SNPS across the genome. Perlegen Sciences (www(dot)perlegen(dot)com) have identified 1.1 million common SNP markers (a density of 1 SNP per 2 kb) by resequencing the nonrepetitive sequences of the human genome in 20 to 50 haploid genomes segregated in human/rodent somatic cell hybrids. This SNP search is based on a similar strategy to that reported in a study of chromosome 21 reported by Patil et al[17]. From this they have defined, using a dynamic programming algorithm[18], a set of 200,000 tagging SNPs that report unambiguously more than 80% of common haplotypes defined by the complete set of 1.1 million SNPs. It is this set of 200,000 tagging SNPs that were used in this example.

The SNPs are typed on high-density oligonucleotide arrays developed by Affymetrix, which have been extensively validated in routine use. Briefly, the array design uses 80 features (25-mer oligonucleotides) to query each SNP. The 80 features comprise 10 overlapping feature sets where each feature set includes 4 features specific for the reference allele (one perfect match and 3 mismatch features) and 4 similar features for the alternative allele. By comparing the fluorescence intensities of perfect match features for the reference allele with those that are perfect matches for the alternative allele, the three possible SNP genotypes (common homozygote, heterozygote and rare homozygote) can be distinguished. To carry out the genotyping assay, regions of the sample genome containing SNPs of interest are specifically amplified using multiplex (78-plex) short range PCR. The PCR products from each individual are pooled and labeled with biotin to create target DNA. The target DNA is hybridized to the SNP-typing high density oligonucleotide arrays. After overnight hybridization, the arrays are washed, stained and scanned for fluorescence intensities.

In this example, the features to genotype the 200,000 SNPs are arrayed onto a series of 6 high-density arrays, requiring that target DNA with a complexity of approximately 30,000 SNPs be used for hybridization. A target of this complexity gives a call rate of 97.3%. Comparison of the high density array genotyping technology with other technologies (real-time PCR and fluorescence polarization) shows a consistent concordance of greater than 99% in approximately 20,000 genotypings with up to 20 different SNPs. The technology has proven to be robust when used with DNA from a variety of collaborating clinical and research laboratories, and to work well with genome amplified DNA.

A property of the 200,000 tagging SNPs to be used in this study, is their ability to 'report' on all other SNP variants within the genome. For given power, the required sample size is proportional to $1/r^2$, where r is the coefficient of linkage disequilibrium between the functional variant which is being sought and the most closely linked tagging SNP[19].

The distribution of $r^2$ between non-tagging SNPs and their corresponding tagging SNP was determined empirically by genotyping 1608 SNPs, evenly spaced over a 4 Mb region of genomic DNA, in 28 unrelated individuals (56 chromosomes): see Table 1. The mean $r^2$ for all 988 tester SNPs, each with a minor allele frequency of >10%, was 67%, with 69% of SNPs having an $r^2$ greater than 0.5.

TABLE 1

Table 1 Distribution of $r^2$ values between 417 selected 'tagging' SNPs and 988 'tester' SNPs, determined in a 4 Mb segment of chromosome 21 in 28 individuals distinct from those used for SNP discovery. 15% of the total set of SNPs had minor allele frequencies 1-10%; 85% had frequencies greater than 10% with an even distribution between 10 and 50%. All tester SNPs had a minor allele frequency >10%. The average spacing of the 417 tagging SNP set was 1 per 10 kb, similar to that in the 200,000 SNP set to be used in the genome scan.

Table 1

| $r^2$ | % of tester SNPs |
|---|---|
| 0.9-1.0 | 34% |
| 0.8-0.89 | 10% |

TABLE 1-continued

Table 1 Distribution of r² values between 417 selected 'tagging' SNPs and 988 'tester' SNPs, determined in a 4 Mb segment of chromosome 21 in 28 individuals distinct from those used for SNP discovery. 15% of the total set of SNPs had minor allele frequencies 1-10%; 85% had frequencies greater than 10% with an even distribution between 10 and 50%. All tester SNPs had a minor allele frequency >10%. The average spacing of the 417 tagging SNP set was 1 per 10 kb, similar to that in the 200,000 SNP set to be used in the genome scan.

Table 1

| r² | % of tester SNPs |
|---|---|
| 0.7-0.79 | 9% |
| 0.6-0.69 | 9% |
| 0.5-0.59 | 8% |
| 0.4-0.49 | 6% |
| 0.3-0.39 | 7% |
| 0.2-0.29 | 7% |
| 0.1-0.19 | 8% |
| 0.0-0.09 | 2% |

Increasing the set of 200,000 tagging SNPs increases the proportion of SNPs in the total genome that are reported, but at increased cost. Even a set of 1.1 million SNPs would not provide complete coverage, since some bases could not be assayed and some common SNPs are missed due to the limited number of chromosomes surveyed. We conclude that the 200,000 tagging SNP set provides a good compromise between coverage and cost.

Previous studies focus on the genetics of cancer predisposition, including an increasing focus on low penetrance susceptibility[13,14,2-23]. Relevant topics for include: (1) assembly of case and control sets; (2) development of genetic models for breast cancer susceptibility; (3) establishment of laboratory facilities for association studies.

(1) Sample Sets

Breast Cancer Cases—Population Based Set.

We have assembled a population based set of (currently 4900) cases of invasive breast cancer diagnosed before the age of 70, ascertained through the local Anglian Cancer Registry. The median time 15 from diagnosis to completion of recruitment is 6 months (interquartile range 3 to 9 months). 65% of all eligible cases have provided a blood sample. This set provides some of the familial cases to be analyzed in stage 1 of our study, and the population based series of cases for stage 2. In addition to a blood sample, subjects complete a questionnaire which includes family history to second degree relatives, reproductive history, breast feeding, oral contraceptive and HRT use, benign breast disease, medical history including other cancers, smoking, alcohol, education and ethnic group. Registry data include clinical stage, pathological grade and stage, simple treatment data and follow-up for survival. Paraffin blocks of tumour are available from 800 cases currently, and can in principle be collected for the majority of the entire set if funding is available.

Breast Cancer Cases—Familial Set.

Through the familial breast cancer clinic in Cambridge and the population-based set described above, a set of over 200 cases with either a strong family history of breast cancer or bilateral primary breast cancers has been assembled, that have tested negative for BRCA1 and BRCA2 mutations. These cases, together with similar cases obtained by collaboration with other CR UK groups, forms the 'genetically enriched' case set for the first stage of the association study.

Controls.

Control DNAs for both stage 1 and stage 2 of the study are obtained from the EPIC-Norfolk cohort[24]. This is part of the Multicentre European Prospective Investigation of Cancer, a 450,000 strong population based cohort of men and women aged 45 to 70 at recruitment from whom blood, extensive epidemiological information and follow up are available. The 25,000 participants in EPIC-Norfolk are volunteers ascertained from family medical practices in Norfolk, which is within the same Anglian region from which the breast cancer cases are obtained. In addition to providing the controls for the gene discovery phase of this project, the larger EPIC cohort provides samples and data for confirmation of positive associations and for the investigation of gene/lifestyle interactions at the follow-up stage.

The study population is relatively homogeneous ethnically, with more than 95% of the population recorded as white and born in the U.K. Evidence for population stratification in this population has been evaluated by genotyping 1655 controls for SNPs in 23 unlinked genes. No significant association between unlinked loci was found, indicating no evidence of stratification[25].

Additional Phenotypic Information in the EPIC Control Set.

Of relevance to the study, extensive phenotypic information is either available (in subsets of individuals) or can readily be obtained, from the 400 EPIC controls who will be genotyped for 200,000 SNPs in stage 1. These quantitative or semi-quailtitative phenotypes are evaluated for genotype associations. Phenotypes relevant to breast cancer include: mammographic density, heel bone density, body mass index, and a range of measurements in serum, of which so far estrogen metabolites, SHBG, IGF-1, and some cytokines are already available in different sets of individuals. Other phenotypes include blood pressure, lipid profiles, C-reactive protein, fibrinogen, full blood count, glycated haemoglobin and thyroid function. In 2004 and 2005 limited recalls are planned for re-interview and further blood sampling, with the possibility of additional phenotyping and the collection of fresh serum and viable cells.

(2) Genetic Models for Breast Cancer Susceptibility.

We analysed the first 1500 breast cancers ascertained in the Anglian population-based study for mutations in BRCA1 and BRCA2, and found, consistent with Peto et al, that only 15% of the familial clustering of breast cancer is attributable to mutations in these genes. Our segregation analysis of the patterns of breast cancer in the families of cases in this study (subsequently tested on other series) led to the polygenic model summarised earlier[13]. This model in turn underlies the calculations of the increased power for association studies provided by using familial rather than unselected cases, which is the basis of the proposed two-stage design used in this example[26].

(3) Laboratory Set Up for Sample Processing and SNP Genotyping.

A moderate throughput genotyping laboratory based on the 384-well Taqman platform, is used for candidate gene association studies. Genotyping capacity is ~100,000 SNPs per week.

In brief, the laboratory set up is as follows. Study participants are given a code-number at recruitment which remains attached to all their data and their biological sample tubes as a bar-code. Within the laboratory, samples are tracked with a Laboratory Information Management System (Thermo, Altringham UK). DNA is extracted, in batches of 96 subjects, from whole blood in coded tubes by Whatman Ltd (Ely, UK) and returned in coded arrays with DNA nonnalised to 40 ng/µl. Pre-amplification of the whole genome is performed on the normalised arrays and the products stored in aliquots. 384-well working-stocks for genotyping are created from equal numbers of cases and controls interleaved with blank wells as negative controls. 3% of samples from a study are duplicated. Thus, the cases and controls (described above) are held in 13 plates—12 of unique samples and a $13^{th}$ of duplicates. Genotyping is carried out on all study-plates simultaneously—reagents are added by robot (Matrix, UK), thermal cycling on MJ Tetrads (GRI, UK) and end-point fluorescence detection by 7900 Sequence Detector (ABI, Warrington, UK). Genotypes are exported to a database and linked to the phenotypic data on each subject. Control genotypes are tested for departure from Hardy-Weinberg Equilibrium as a final quality control step.

Research Design

The study is organised in stages:

Stage 1.

The full set of 200,000 tagging SNPs is analysed in 400 unrelated breast cancer cases enriched for family history, and 400 female controls drawn from the EPIC study. The breast cancer cases will have been screened negative for BRCA1/2 mutations.

Stage 2.

SNPs that show a significant difference in frequency between the cancer series and the control series, at the p<0.05 level, are re-evaluated in a further 4600 breast cancer cases and 4600 matched controls.

Rationale for the Research Design

The staged design is chosen to minimise the amount of genotyping required, while retaining a high power to detect SNPs with a modest effect on risk. With the proposed thresholds, approximately 10,000 SNPs will go forward to stage 2, while substantially fewer (depending on the number of "true" associations) are expected to be put forward at the end of stage 2 for additional verification in other studies. Calculations have shown that such a staged design is very efficient compared with genotyping all samples for all SNPs[27].

Cases—Stage 1

Cases are women with invasive breast cancer with at least two first degree relatives with breast cancer, or equivalently strong family history (for example, one first and two second degree relatives affected). These women are selected from cancer genetics centres in the U.K. or from the Anglian Breast Cancer Study. Women whose ethnic group is not recorded as white will be excluded.

We have previously demonstrated that the power to detect associations is strongly related to the degree of family history of the cases[26]. The use of cases with two affected first degree relatives reduces the required sample size by at least fourfold, as compared with using unselected cases. From amongst all available cases, we will select the four hundred cases with the strongest family history. If more than one case is available from the same family we will choose the case with the strongest immediate family history, so that all cases in the set will be unrelated.

All cases are screened (and are negative) for mutations in BRCA1 and BRCA2. This screening includes, screening of all exons and splice junctions by a sensitive screening technique (e.g. CSGE). This is done because it is unknown whether low penetrance alleles that influence breast cancer risk in non-carriers of BRCA1 or BRCA2 mutations will also influence the risk in carriers. The analysis of Antoniou et al[13] suggests a similar "polygenic" component in carriers. However, it is possible that genes modifying the risk in BRCA1 and BRCA2 carriers may be different, particularly given the distinctive pathology of BRCA1 tumours. BRCA1 and BRCA2 mutations would be present in more than 20% of cases selected by the criteria used in stage 1. If a polymorphism of interest did not influence the disease risk in carriers, inclusion of carriers could reduce the power of the study. The study, thus, conservatively screens for and excludes known BRCA1 and BRCA2 mutation carriers. This approach is estimated to exclude approximately 70% of BRCA1 mutations and 90% of BRCA2 mutations, so that less than 5% of cases in the final set are likely to harbour unidentified mutations.

Cases—Stage 2

Cases at stage 2 consist of 4,600 cases drawn from the population-based Anglian Breast Cancer (ABC) Study.

While there is an argument for the use of "enriched" cases to maximize power and minimise costs at stage 1, the case is more finely balanced at stage 2. Use of familial cases increases power, but the gain is less marked because the main determinant of power is the efficiency of stage 1. At the same time, the population-based case-control sets are already in use for candidate gene association studies, and DNA samples are already arrayed from stage 1. Developing a new set of familial cases on this scale would entail considerable delay and expense. Secondly, the cases are closely matched geographically to the controls, providing more protection against false positive associations due to regional variation in allele frequencies. Thirdly, the population-based series provides a direct estimate of the relative risk associated with each SNP or haplotype. Fourthly, the ABC study has collected systematically information on lifestyle risk factors and clinical outcome of the cancers. This provides the potential for further analyses to study associations with survival and interactions with lifestyle risk factors. The same quality of information could not be obtained on familial cases.

In summary, by utilizing series of both enriched and population-based case series, we are optimizing the power to detect true associations, while at the same time gaining the added value of genotyping in a well-characterized population-based case control study.

Controls

Controls for both stages 1 and 2 will be women from EPIC study as described above. The age distribution of the controls is similar to that of the cases. Women who are known to have developed cancer, or who are non-white, will be excluded. Controls for stage 1 will be sampled from a sub cohort of 2,000 postmenopausal women for whom detailed analyses of sex steroid hormones and mammographic density have been conducted[28].

Ethical approvals that cover the use of both case and control samples for genetic association studies have been obtained. Both cases and controls have given informed consent for their DNA to be used for such genetic studies.

Statistical Considerations

Statistical Analysis

The primary analysis, at both stages 1 and 2, is to evaluate the association of each SNP individually with breast cancer. Epidemiological studies suggest little or no difference in the relative risk of breast cancer between mothers of and sisters of cases, except possibly at very young ages[1,12], indicating that most susceptibility alleles have little recessive component (as in the polygenic model of Antoniou et al[13]). The primary analyses are, therefore, based on a trend test for the difference in allele frequencies between cases and controls[29]. Cases are weighted by family history to improve the efficiency of the test.

In principle, haplotype analysis or joint genotype analysis can provide some improvement in power[30]. In the current design, however, haplotype analysis is largely redundant since only a small minority of SNPs will be taken through to stage 2, and the power calculations have therefore assumed single SNP analyses. The cost of taking all tagging SNPs in a block through to stage 2 to allow full haplotype analyses would outweigh any gain in power. Haplotype analysis is utilized in those cases where more than one linked SNP in the same LD block is typed at stage 2, and will be utilized extensively in follow-up studies.

Power Calculations

The power of the study has been derived on the basis of a significance level of $p=10^{-4}$ over both stages combined. Approximately 12 loci would be expected to be significant at this level by chance (given the staged design), leaving a manageable number of loci to retest in larger series and a favourable ratio of "true": "false" positives.

The power calculations assume that the cases in stage 1 have a family history of two affected first degree relatives. In practice, the power is somewhat greater since this is the minimum criterion and many of the cases will have a stronger family history. Examples of the power to detect a disease susceptibility allele are given in Table 2, for different values of the disease allele frequency and relative risk, assuming the estimated distribution of $r^2$ from the tagging set. (For polymorphisms with alleles of frequency 0.05, the power has been calculated by assuming that the polymorphism is in LD, at $D'=1$, with a randomly chosen common polymorphism from the set). For common alleles, the power is principally dependent on the contribution of the locus to the overall genetic variance, and is at least 50% for loci explaining 1% of the variance and approximately 80% for loci explaining 2% of the variance. In contrast, for alleles with frequency less than 5%, power is poor unless the effect size is very large.

TABLE 2

Estimated overall power to detect a dominant susceptibility locus with a given allele frequency conferring a given relative risk (P < .0001 after two stages) assuming the distribution of $r^2$ between the susceptibility locus and a tagging SNP based on previously reported data (Table 1). Percentage of overall genetic variance explained in brackets.

| | Allele frequency | | |
|---|---|---|---|
| Relative risk | .2 | .1 | .05 |
| 1.2 | 53% (0.9%) | 27% (0.6%) | <1% (0.3%) |
| 1.3 | 79% (2.0%) | 61% (1.2%) | <1% (0.7%) |
| 1.5 | 91% (5.2%) | 86% (3.2%) | 6% (1.8%) |
| 2.0 | 99% (17.8%) | 97% (11.5%) | 29% (6.7%) |

For quantitative traits measured in the controls, the power is approximately 50% to detect loci explaining at least 5% of the phenotypic variance, at the 5% significance level. These loci would be available for further evaluation in future large studies within the EPIC cohort.

Detailed Evaluation of Susceptibility Loci

Once a significant association is identified, further polymorphisms are evaluated in the region in an attempt to establish the most strongly associated variant or haplotype. The general procedure will be similar to that used for investigating candidate genes. The available databases are searched for known SNPs. Where no systematic search for all available SNPs has been conducted, in-house resequencing of a limited number of individuals (e.g., n=48) is used. After excluding SNPs that are in complete LD, informative SNPs are genotyped in the cases and controls used in stages 1 and 2. Multiple logistic regression is used to investigate the joint effect of multiple SNPs. Further investigations can be performed to identify functional variant(s).

Further Evaluation of Quantitative Trait Loci

SNPs that exhibit significant associations at stage 1 with quantitative traits are available for replication in further series. Since the number of quantitative traits is large, prioritization is performed on the basis of the strength of the association, the plausibility of the locus and the importance of the phenotype. For example, associations with serum sex steroid hormone levels and mammographic density are prioritized favorably, because these are related to breast cancer risk. SNPs associated with these phenotypes are typed in a further 1,600 samples from postmenopausal women in EPIC. If the associations are replicated, they are pursued as above.

REFERENCES

1. Collaborative Group in Hormonal Factors in Breast Cancer (2001) Familial breast cancer: collaborative reanalysis of individual data from 52 epidemiological studies including 58,209 women with breast cancer and 101,986 women without the disease. Lancet 358:1389-1399.
2. Lichtenstein P et al (2000) Environmental and heritable factors in the causation of cancer—analyses of cohorts of twins from Sweden, Denmark, and Finland. New Engl J Med 243:78-85.
3. Peto J, Mack T M (2000) High constant incidence in twins and other relatives of women with breast cancer. Nature Genet 26:411-414.
4. Antoniou A et al (2003) Average risks of breast and ovarian cancer associated with mutations in BRCA1 or BRCA2 detected in case series unselected for family history: a combined analysis of 22 studies. Am J Hum Genet 72:1117-1130.
5. Peto J e.t al (1989) The prevalence of BRCAJ and BRCA2 mutations amongst early onset breast cancer cases in the U.K. J Natl Cancer Inst 91:943-949.
6. The Anglian Breast Cancer Study Group (2000) Prevalence of BRCA1 and BRCA2 mutations in a large population based series of breast cancer cases. Br J Cancer 83:1301-1308.
7. Easton D F (1999) How many more breast cancer predisposition genes are there? Breast Cancer Res 1: 1-4.
8. Ford D et al (1998) Genetic heterogeneity and Penetrance analysis of the BRCA1 and BRCA2 genes in breast cancer families. Am J Hum Genet 62:334-345.
9. Thompson D et al (2002) Evaluation of linkage of breast cancer to the putative BRCA3 locus on chromosome 13q21 in 128 multiple case families from the Breast Cancer Linkage Consortium. Proc Natl Acad Sci USA 99:827-831.
10. Huusko P et al (2003) Genome-wide scanning for linkage in Finnish breast cancer families. Eur J Hum Genet, in press.
11. Antoniou A C et al (2001) Evidence for further breast cancer susceptibility genes in addition to BRCA1 and BRCA2 in a population based study. Genet Epidemiol 21: 1-18.
12. Cui J et al (2000) After BRCA1 and BRCA2—what next? Multifactorial segregation analysis of three-generational, population-based Australian female breast cancer families. Am J Hum Genet 68:420-431.
13. Antoniou A C et al (2002) A comprehensive model for familial breast cancer incorporating BRCA1, BRCA2 and other genes. Brit J Cancer 86:76-83.
14. Pharoah P D P et al (2002) Polygenic susceptibility to breast cancer and implications for prevention. Nature Genetics 31:33-36.
15. Titus-Emstoff L et al (1998) Menstrual factors in relation to breast cancer risk. Cancer Epidemiol Biomarkers Prev. 7: 783-9.
16. Kriege et al (2003) MRI screening for breast cancer in women with high familial and genetic risk: First results of the Dutch MRI screening study (MRISC). Proc Am Soc Clin Oncol 22:A5.
17. Patil N et al (2001) Blocks of limited haplotype diversity revealed by high-resolution scanning of human chromosome 21. Science 294:1719-1723.
18. Zhang K et al (2002) A dynamic programming algorithm for haplotype block partitioning. Proc Natl Acad Sci USA 99: 7335-7339.
19. Pritchard J K, Przeworski M (2001) Linkage disequilibrium in humans: models and data. Am J Hurn Genet 69: 1-14.
20. Dunning A M et al (1999). A systematic review of genetic polymorphisms and breast cancer risk. Cancer Epidemiol Biomarkers Prevention 8:843-854.
21. Healey C S et al (2000) A common variant in BRCA2 is associated with both breast cancer risk and prenatal viability. Nature Genet 26:362-364.
22. Kuschel B et al (2002) Variants in DNA double strand break repair genes and breast cancer susceptibility. Hum Mol Genet 11:1399-1407.
23. Dunning A M et al (2003) A TGF~-1 signal peptide variant increases secretion in vitro and is associated with increased incidence of invasive breast cancer. Cancer Res 63:2610-15.
24. Day N et al (1999) EPIC-Norfolk: study design and characteristics of the cohort. European Prospective Investigation of Cancer. Br J Cancer 80 Suppl 1:95-103.
25. Goode E L et al (2001) Assessment of population stratification in a large population based cohort. Genet Epidemiol 21:A126.
26. Antoniou A, Easton D F (2003) Polygenic inheritance of breast cancer: implications for design of association studies. Genet Epidemiol 25: 190-202.
27. Satagopan J M et al (2002) Two-staged designs for gene-disease association studies. Biometrics 58: 163-170.
28. Dunning A M et al (2004) Polymorphisms associated with circulating sex hormone levels in post-menopausal women. J Natl Cancer Inst, in press.
29. Sasieni P D (1997) From genotypes to genes: doubling the sample size. Biometrics 53:1253-1261.
30. Chapman J P et al (2003) Detecting disease associations due to linkage disequilibrium using haplotype tags: a class of tests and the determinants of statistical power. Hum Hered 56: 18-31.

Example 2: Marker Polymorphisms Associated with Breast Cancer Predisposition

SNPs identified as being associated with breast cancer risk (predisposition) are set forth in FIGS. 1 and 2. FIG. 1 provides the currently most preferred associations; FIG. 2 provides additional associations.

Sequences for given dbSNP rsID numbers (see, "REFSNP ID," column 2 from the Figures) are found at: www(dot) ncbi(dot)nlm(dot)nih(dot)gov/SNP/. In FIGS. 1 and 2, the second column is labeled "REFSNP ID". The values in this column are SNP identification numbers according to the dbSNP database established and maintained by NCBI of the US National Library of Medicine at the US National Institute of Health. The NCBI dbSNP database is publicly accessible and considerable additional information can be easily viewed by searching the database using the rsID numbers provided in the Figures by entering the number prefixed by "rs" in the database search window and clicking on "Search." The information provided can include, but is not limited to, alleles at the SNP locus, flanking nucleotide sequences, and submission information.

The SNP ID column numbers (See, column 1, FIGS. 1 and 2) reference publicly available Perlegen SNP identification numbers, which can be viewed with associated information at Perlegen(dot)com, using the company's available genome browser at genome(dot)perlegen(dot)com/browser/index (dot)html, following the instructions provided (Perlegen Sciences, Inc., Menlo Park, Calif.). As noted in the instructions provided, wild card characters (e.g., "*" symbols) can be added at the beginning of the SNP ID to identify pertinent information for all alleles
of the SNP. This database also links to the NCBI genomic database. In the figures, the first row on each page is a header row with the column names. The columns are as follows:

| Header | description of content |
|---|---|
| SNP_ID | Perlegen internal SNP identifier. |
| REFSNP_ID | The dbSNP RefSNP cluster ID (from NCBI) when available. Can be null. |
| SUBSNP_ID | The dbSNP submission ID for SNPs Perlegen submitted to dbSNP. Can be null. |
| ACCESSION_ID | The accession number from NCBI Build 35 of the contig to which the SNP aligns; may be null. |
| POSITION | Nucleotide position in NCBI build 35 contig of the reference base in the alignment; may be null. |
| ALLELE_1 | The nucleotide code for allele 1 (Perlegen ref allele). |
| ALLELE_2 | The nucleotide code for allele 2 (Perlegen alt allele). |
| Ptrend_weighted | The trend score p-value of the association, weighted by degree of family history for each sample |
| Gene_name | NCBI gene database symbol of a gene near SNP |
| geneDescription | NCBI gene database description of the gene |
| HIT_TYPE | The type of hit: exon, intron, up (within 10 kb upstream of transcription start site), down (within 10 kb downstream of the transcription stop). Numbers indicate distances greater than 10 kb, in addition to hit type. |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to he incorporated by reference for all purposes.

What is claimed is:

1. A method of determining the identity of the alleles of single nucleotide polymorphisms (SNPs) in a woman subject selected from the group of subjects consisting of women in need of screening for breast cancer susceptibility to produce a polymorphic profile of the selected woman subject in need of breast cancer screening, comprising
- (i) obtaining a biological sample comprising a genome from the selected woman subject in need of breast cancer screening;
- (ii) selecting for allelic identity analysis at least a SNP located at rs13281615 within the genome of the selected woman subject in need of breast cancer screening;
- (iii) assaying, with a probe or a primer, whether
  - a) the selected woman subject is homozygous or heterozygous for a guanine (G) allele, or a complement thereof, located at rs13281615 within the nucleotide sequence of the genome in the biological sample of step (i),
  - wherein
  - if the assaying is with a primer, then the assaying comprises
    - (1) hybridizing a primer capable of initiating nucleic acid polymerization by a polymerase with a nucleic acid, the nucleic acid having the SNP located at rs13281615, or
    - (2) hybridizing a primer capable of initiating nucleic acid polymerization by a polymerase with a nucleic acid having the sequence of an allele, or a complement thereof, located at rs13281615 within the nucleotide sequence of the genome of the woman subject, and
  - if the assaying is with a probe, then the assaying comprises hybridizing a probe to a nucleic acid having the sequence of the guanine (G) allele, or a complement thereof, located at rs13281615 within the nucleotide sequence of the genome of the woman subject, and
- (iv) producing the polymorphic profile of the selected woman subject in need of breast cancer screening based on the identity of the alleles assayed in step (iii).

2. The method of claim 1, wherein the selected woman subject in need of screening for breast cancer susceptibility has at least two first degree relatives who have had breast cancer.

3. The method of claim 2, wherein the two first degree relatives of the selected woman subject in need of screening for breast cancer susceptibility are siblings of the woman subject in need of screening for breast cancer susceptibility.

4. The method of claim 2, wherein one of the first degree relatives of the selected woman subject in need of screening for breast cancer susceptibility is the mother of the woman subject in need of screening for breast cancer susceptibility.

5. The method of claim 1, wherein the selected woman subject in need of screening for breast cancer susceptibility has one first and two second degree relatives who have had breast cancer.

6. The method of claim 5, wherein the first degree relative of the selected woman subject in need of screening for breast cancer susceptibility is the mother of the selected woman subject in need of screening for breast cancer susceptibility.

7. The method of claim 1, wherein the selected woman subject in need of screening for breast cancer susceptibility is not known to have developed cancer.

8. The method of claim 1, wherein the selected woman subject in need of screening for breast cancer susceptibility does not have a BRCA1/2 mutation.

9. The method of claim 1, wherein the selected woman subject in need of screening for breast cancer susceptibility is postmenopausal.

* * * * *